US012590139B2

(12) United States Patent
Hirano et al.

(10) Patent No.: US 12,590,139 B2
(45) Date of Patent: Mar. 31, 2026

(54) MHC CLASS II MOLECULES AND METHODS OF USE THEREOF

(71) Applicant: University Health Network, Toronto (CA)

(72) Inventors: Naoto Hirano, Toronto (CA); Kenji Sugata, Toronto (CA)

(73) Assignee: University Health Network, Toronto (CA)

( * ) Notice: Subject to any disclaimer, the term of this patent is extended or adjusted under 35 U.S.C. 154(b) by 696 days.

(21) Appl. No.: 17/631,821

(22) PCT Filed: Jul. 29, 2020

(86) PCT No.: PCT/IB2020/057173
§ 371 (c)(1),
(2) Date: Jan. 31, 2022

(87) PCT Pub. No.: WO2021/019473
PCT Pub. Date: Feb. 4, 2021

(65) Prior Publication Data
US 2022/0275051 A1    Sep. 1, 2022

Related U.S. Application Data

(60) Provisional application No. 63/029,114, filed on May 22, 2020, provisional application No. 62/880,501, filed on Jul. 30, 2019.

(51) Int. Cl.
*C07K 14/74*     (2006.01)
*A61K 38/00*     (2006.01)
*A61P 35/00*     (2006.01)

(52) U.S. Cl.
CPC ........ *C07K 14/70539* (2013.01); *A61P 35/00* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 2003/0064915 A1 | 4/2003 | Strominger et al. | |
| 2005/0042624 A1 | 2/2005 | Itoh et al. | |
| 2006/0084116 A1 | 4/2006 | Muchhal | |
| 2006/0228758 A1 | 10/2006 | Muchhal et al. | |
| 2013/0287748 A1 | 10/2013 | June et al. | |
| 2022/0281948 A1 | 9/2022 | Hirano et al. | |
| 2022/0281949 A1 | 9/2022 | Hirano et al. | |
| 2022/0291215 A1 | 9/2022 | Hirano et al. | |

FOREIGN PATENT DOCUMENTS

| | | |
|---|---|---|
| CA | 2995838 A1 | 2/2017 |
| CN | 1244804 A | 2/2000 |
| CN | 1902313 A | 1/2007 |
| CN | 101001868 A | 7/2007 |
| CN | 109476727 A | 3/2019 |
| WO | WO-02077030 A2 | 10/2002 |
| WO | WO-2008109075 A2 | 9/2008 |
| WO | WO-2016135363 A1 | 9/2016 |
| WO | WO-2019126818 A1 | 6/2019 |

OTHER PUBLICATIONS

National Library of Medicine (US), National Center for Biotechnology Information;—. Accession No. XP_012517264, Predicted: HLA class II histocompatibility antigen, DQ beta 1 chain-like [Propithecus coquereli]; [cited Jun. 1, 2015]. https://www.ncbi.nlm.nih.gov/protein/XP_012517264.1/ (Year: 2015).*

Gustafsson et al. Class II Genes of Miniature Swine. Journal of Immunology, vol. 145, 1946-1951, No. 6, Sep. 15, 1990 (Year: 1990).*

Anczurowski, M., et al., "Mechanisms underlying the lack of endogenous processing and CLIP-mediated binding of the invariant chain by HLA-DP84Gly," Sci. Rep. 8:4804, Springer, Germany (Mar. 2018).

Butler, M.O., et al., "Ex vivo expansion of human CD8+ T cells using autologous CD4+ T cell help," PloS One 7:e30229, PLOS, United States (Jan. 2012).

Butler, M.O., et al., "Long-lived antitumor CD8+ lymphocytes for adoptive therapy generated using an artificial antigen-presenting cell," Clin Cancer Res 13:1857-1867, American Association for Cancer Research, United States (Mar. 2007).

De Jong, W., and Borm, P., "Drug delivery and nanoparticles:applications and hazards," Int. J Nanomedicine 3(2):133-49, Dove Medical Press, United Kingdom (Jun. 2008).

Fleury, S., et al., "HLA-DR Polymorphism Affects the Interaction with CD4," J Exp Med 182(3):733-741, Rockefeller University Press, United States (Sep. 1995).

Genbank, "HLA class II histocompatibility antigen, DP beta 1 chain [*Cavia porcellus*]," Accession No. XP_003473759, accessed at https://www.ncbi.nlm.nih.gov/protein/XP_003473759.2/, Jan. 2018, accessed on Dec. 18, 2024, 2 pages.

(Continued)

*Primary Examiner* — Christina Bradley
(74) *Attorney, Agent, or Firm* — Sterne, Kessler, Goldstein & Fox P.L.L.C.

(57)     ABSTRACT

The present disclosure is directed to HLA class II molecules having a higher affinity for CD4 than naturally occurring HLA class II molecules. In certain aspects, the HLA class II molecule comprises a DQ beta chain having (i) an amino acid other than leucine at a position corresponding to amino acid residue 114 of SEQ ID NO: 1, (ii) an amino acid other than valine at a position corresponding to amino acid residue 143 of SEQ ID NO: 1, (iii) or both (i) and (ii). Certain aspects of the present disclosure are directed to nucleic acid molecules encoding the HLA class II molecules, vectors comprising the nucleic acid molecule, cells comprising the same, and methods of use thereof.

14 Claims, 7 Drawing Sheets
Specification includes a Sequence Listing.

(56) References Cited

OTHER PUBLICATIONS

Genbank, "HLA class II histocompatibility antigen, DP beta 1 chain-like," Accession No. XP_023576849, accessed at https://www.ncbi.nlm.nih.gov/protein/XP_023576849.1/, Jan. 2018, accessed on Dec. 18, 2024, 2 pages.

Genbank, "HLA class II histocompatibility antigen, DQ beta 1 chain," Accession No. XP_008260979, accessed at https://www.ncbi.nlm.nih.gov/protein/XP_008260979.2/, Jun. 23, 2016, accessed on Dec. 18, 2024, 2 pages.

Genbank, "MHC class II antigen [Homo sapiens]," Accession No. CQR91450, accessed at https://www.ncbi.nlm.nih.gov/protein/CQR91450.1/, Jul. 2017, accessed on Dec. 18, 2024, 2 pages.

Genbank, "MHC class II antigen, partial," Accession No. AUZ41832, accessed at https://www.ncbi.nlm.nih.gov/protein/AUZ41832.1/, Feb. 2018, accessed on Dec. 18, 2024, 2 pages.

Genbank, "Predicted: boLa class II histocompatibility antigen, DQB*0101 beta chain," Accession No. XP_005879777, accessed at https://www.ncbi.nlm.nih.gov/protein/XP_005879777.2/ Nov. 2015, accessed on Dec. 18, 2024, 2 pages.

Genbank, "Predicted: HLA class II histocompatibility antigen, DQ beta 1 chain-like [Propithecus coquereli]," Accession No. XP_012517264, accessed at https://www.ncbi.nlm.nih.gov/protein/XP_012517264.1/, Jun. 2015, accessed on Dec. 18, 2024, 2 pages.

GenBank, "T-cell surface glycoprotein CD4 isoform 1 precursor [Homo sapiens]," Accession No. NP_000607.1, accessed at https://www.ncbi.nlm.nih.gov/protein/NP_000607.1/, Aug. 2024, accessed on Dec. 18, 2024, 5 pages.

Hasan, A.N., et al., "Artificial Antigen Presenting Cells: An Off the Shelf Approach for Generation of Desirable T-Cell Populations for Broad Application of Adoptive Immunotherapy," Adv. Genet. Eng. 4(3):130, (Oct. 2015).

Heemskerk, M.H., et al., "Redirection of antileukemic reactivity of peripheral T lymphocytes using gene transfer of minor histocompatibility antigen HA-2-specific T-cell receptor complexes expressing a conserved alpha joining region," Blood 102:3530-3540, American Society of Hematology, United States (Nov. 2003).

Hirano, N., et al., "Efficient presentation of naturally processed HLA class I peptides by artificial antigen-presenting cells for the generation of effective antitumor responses," Clin Cancer Res 12:2967-2975, American Association for Cancer Research, United States (May 2006).

Hirano, N., et al., "Engagement of CD83 ligand induces prolonged expansion of CD8+ T cells and preferential enrichment for antigen specificity," Blood 107:1528-1536, American Society of Hematology, United States (Feb. 2006).

Hirano, N., et al., "Identification of an immunogenic CD8+ T-cell epitope derived from gamma-globin, a putative tumor-associated antigen for juvenile myelomonocytic leukemia," Blood 108:2662-2668, American Society of Hematology, United States (Oct. 2006).

Huang, B., et al., "Analysis of the contact sites on the CD4 molecule with class II MHC molecule: co-ligand versus co-receptor function," J Immunol 158(1):216-25, American Association of Immunologists, United States (Jan. 1997).

Huang, S., and Kamihira, M., "Development of hybrid viral vectors for gene therapy," Biotechnol. Adv. 31(2):208-23, Elsevier, Netherlands (May 2013).

International Search Report and Written Opinion for International Application No. PCT/IB2020/057176, Canadian Intellectual Property Office, Quebec, mailed on Nov. 10, 2020, 11 pages.

Janeway, C., et al., "Recognition of MHC Class II Antigens by the CD4: T Cell Receptor Complex," In: H-2 Antigens. NATO ASI Series (Series A: Life Sciences), David C.S., eds., pp. 441-449, Springer, United States (1987).

Nakatsugawa, M et al., "Specific roles of each TCR hemichain in generating functional chain-centric TCR," J Immunol 194:3487-3500, American Association of Immunologists, United States (Apr. 2015).

Nakatsugawa, M., et al., "CD4(+) and CD8(+) TCRβ repertoires possess different potentials to generate extraordinarily high-avidity T cells," Sci Rep 6:23821, Springer, Germany (Mar. 2016).

Ochi, T., et al., "Optimization of T-cell Reactivity by Exploiting TCR Chain Centricity for the Purpose of Safe and Effective Antitumor TCR Gene Therapy," Cancer Immunol Res 3:1070-1081, American Association for Cancer Research, United States (Sep. 2015).

Rhesus Macaque Genome Sequencing and Analysis Consortium, Gibbs, R., et al., "Evolutionary and biomedical insights from the rhesus macaque genome," Science 316(5822):222-34, American Association for the Advancement of Science, United States (Apr. 2007).

Su, L.F., et al., "Virus-specific CD4(+) memory-phenotype T cells are abundant in unexposed adults," Immunity 38:373-383, Cell Press, United Kingdom (Feb. 2013).

Umeshappa, C., et al., "Suppression of a broad spectrum of liver autoimmune pathologies by single peptide-MHC-based nanomedicines," Nat. Commun. 10(1):2150, Springer, Germany (May 2019).

Wang, X.X., et al., "Affinity Maturation of Human CD4 by Yeast Surface Display and Crystal Structure of a CD4-HLA-DR1 Complex," PNAS, 108(38):15960-15965, National Academy of Sciences, United States (Sep. 2011).

Weber, K.S., et al., "Class II-restricted T cell receptor engineered in vitro for higher affinity retains peptide specificity and function," PNAS 102(52):19033-19038, National Academy of Sciences, United States (Dec. 2005).

Wooldridge, L., et al., "Anti-coreceptor antibodies profoundly affect staining with peptide-MHC class I and class II tetramers," Eur J Immunol 36:1847-1855, Wiley-VCH, United States (Jun. 2006).

Yamashita, Y., et al., "HLA-DP84Gly constitutively presents endogenous peptides generated by the class I antigen processing pathway," Nat. Commun. 8:15244, Springer, Germany (May 2017).

Yao, X., et al., "Isolation and Characterization of an HLA-DPB1*04: 01-restricted MAGE-A3 T-Cell Receptor for Cancer Immunotherapy," J Immunother. 39:191-201, Lippincott Williams and Wilkins Ltd., United States (Jun. 2016).

Feng, S., et al., "QM/MM Molecular Dynamics Simulation for the MHC class I Molecule Interacting with Antigen Peptide," Acta Chimica Sinica 71(9):1313-1320, SIOC Journals, China (Jun. 2013).

Kremer, A.N., et al., "Natural T-cell ligands that are created by genetic variants can be transferred between cells by extracellular vesicles," Eur J Immunol 48(10):1621-1631, Wiley, United States (Oct. 2018).

Sugata, K., et al., "Affinity-matured HLA class II dimers for robust staining of antigen-specific CD4+ T cells," Nature biotechnology 39(8):958-967, Nature Portfolio, Germany (Aug. 2021).

UniProt, "MHC class II antigen," Accession No. XP_093087560, accessed at https://www.uniprot.org/uniprotkb/F8LFW2/entry, accessed on Dec. 18, 2024, 6 pages.

UniProt, "MHC class II antigen," Accession No. XP_093087727, accessed at https://www.uniprot.org/uniprotkb/Q7YPT7/entry, accessed on Dec. 18, 2024, 7 pages.

International Search Report and Written Opinion for International Application No. PCT/IB2020/057173, Canadian Intellectual Property Office, Canada, mailed on Nov. 10, 2020, 21 pages.

Marsh, S.G.E., et al., "Nomenclature for factors of the HLA system, 2010," Tissue Antigens, 75(4):291-455, John Wiley & Sons, United States (Apr. 2010).

* cited by examiner

FIG. 1E

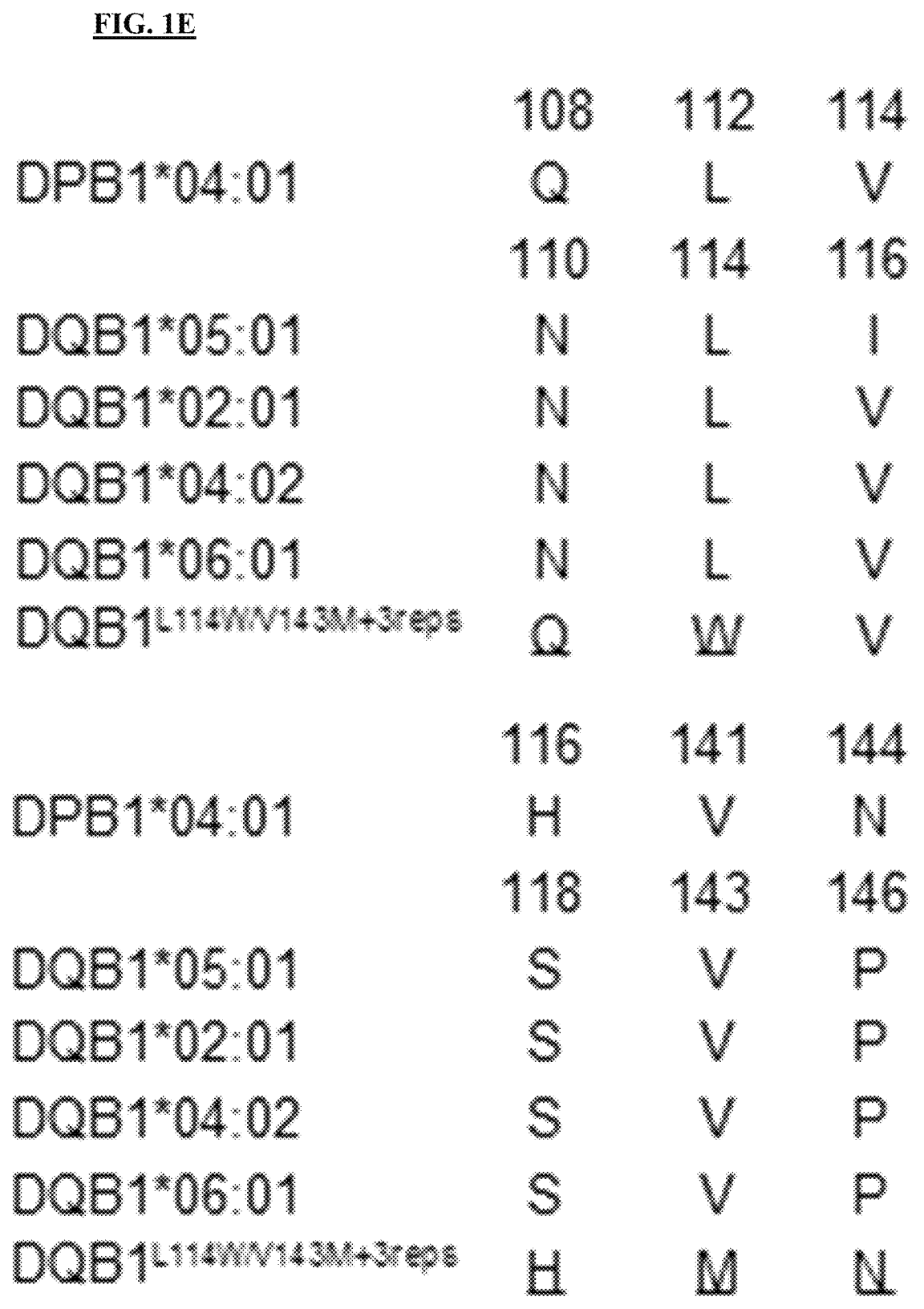

|  | 108 | 112 | 114 |
|---|---|---|---|
| DPB1*04:01 | Q | L | V |

|  | 110 | 114 | 116 |
|---|---|---|---|
| DQB1*05:01 | N | L | I |
| DQB1*02:01 | N | L | V |
| DQB1*04:02 | N | L | V |
| DQB1*06:01 | N | L | V |
| DQB1 L114W/V143M+3reps | Q | W | V |

|  | 116 | 141 | 144 |
|---|---|---|---|
| DPB1*04:01 | H | V | N |

|  | 118 | 143 | 146 |
|---|---|---|---|
| DQB1*05:01 | S | V | P |
| DQB1*02:01 | S | V | P |
| DQB1*04:02 | S | V | P |
| DQB1*06:01 | S | V | P |
| DQB1 L114W/V143M+3reps | H | M | N |

FIG. 1F

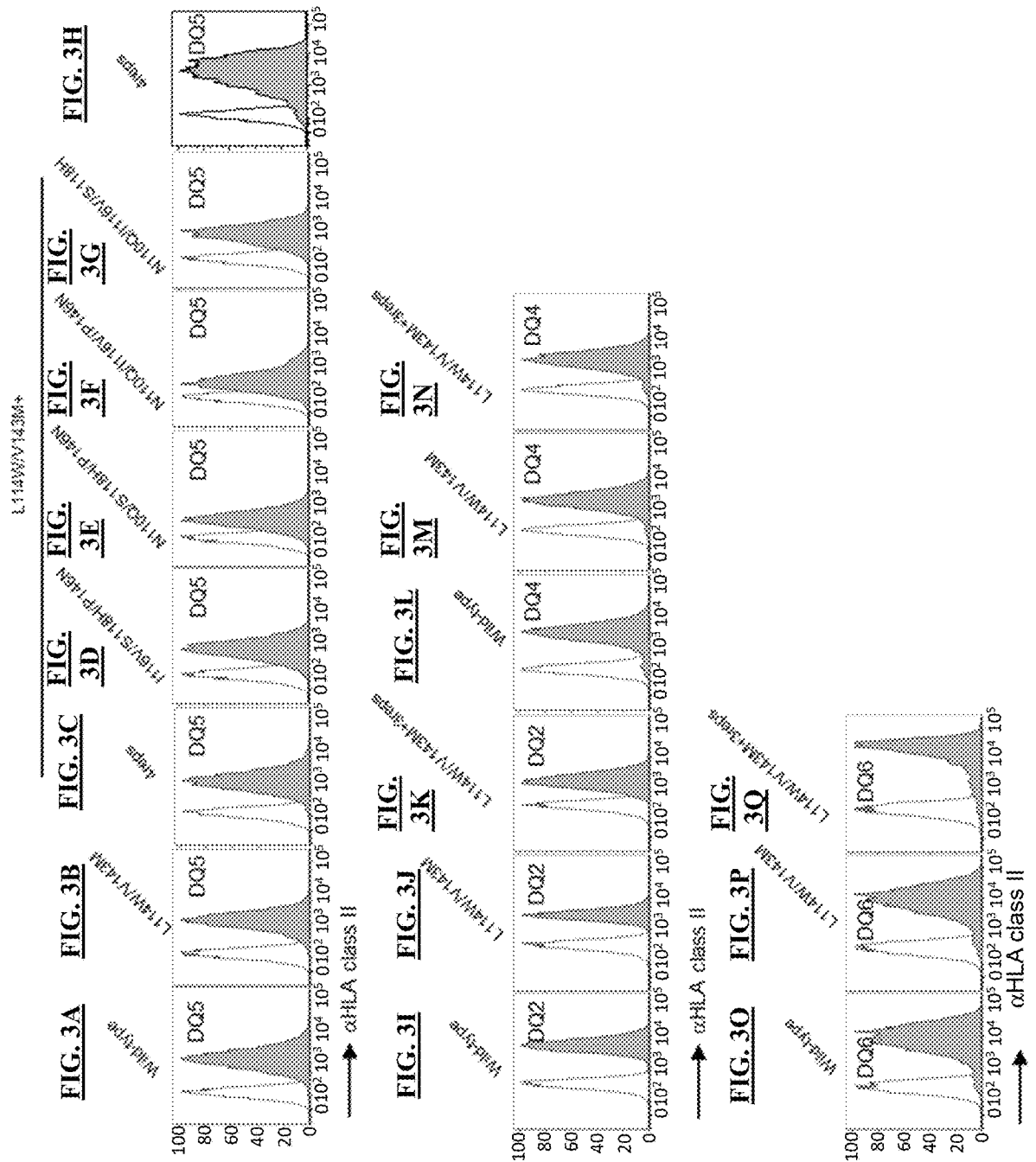

SEQUENCE LISTING

```
<160> NUMBER OF SEQ ID NOS: 15

<210> SEQ ID NO 1
<211> LENGTH: 198
<212> TYPE: PRT
<213> ORGANISM: Artificial Sequence
<220> FEATURE:
<223> OTHER INFORMATION: synthetic construct

<400> SEQUENCE: 1

Arg Asp Ser Pro Glu Asp Phe Val Tyr Gln Phe Lys Gly Leu Cys Tyr
1               5                   10                  15

Phe Thr Asn Gly Thr Glu Arg Val Arg Gly Val Thr Arg His Ile Tyr
            20                  25                  30

Asn Arg Glu Glu Tyr Val Arg Phe Asp Ser Asp Val Gly Val Tyr Arg
        35                  40                  45

Ala Val Thr Pro Gln Gly Arg Pro Val Ala Glu Tyr Trp Asn Ser Gln
    50                  55                  60

Lys Glu Val Leu Glu Gly Ala Arg Ala Ser Val Asp Arg Val Cys Arg
65                  70                  75                  80

His Asn Tyr Glu Val Ala Tyr Arg Gly Ile Leu Gln Arg Arg Val Glu
                85                  90                  95

Pro Thr Val Thr Ile Ser Pro Ser Arg Thr Glu Ala Leu Asn His His
            100                 105                 110

Asn Leu Leu Ile Cys Ser Val Thr Asp Phe Tyr Pro Ser Gln Ile Lys
        115                 120                 125

Val Arg Trp Phe Arg Asn Asp Gln Glu Glu Thr Ala Gly Val Val Ser
        130                 135                 140

Thr Pro Leu Ile Arg Asn Gly Asp Trp Thr Phe Gln Ile Leu Val Met
145                 150                 155                 160

Leu Glu Met Thr Pro Gln Arg Gly Asp Val Tyr Thr Cys His Val Glu
                165                 170                 175

His Pro Ser Leu Gln Ser Pro Ile Thr Val Glu Trp Arg Ala Gln Ser
            180                 185                 190

Glu Ser Ala Gln Ser Lys
            195

<210> SEQ ID NO 2
<211> LENGTH: 594
<212> TYPE: PRT
<213> ORGANISM: Artificial Sequence
<220> FEATURE:
<223> OTHER INFORMATION: synthetic construct

<400> SEQUENCE: 2

Ala Gly Ala Gly Ala Cys Thr Cys Thr Cys Cys Cys Gly Ala Gly Gly
1               5                   10                  15

Ala Thr Thr Thr Cys Gly Thr Gly Thr Ala Cys Cys Ala Gly Thr Thr
            20                  25                  30

Thr Ala Ala Gly Gly Gly Cys Cys Thr Gly Thr Gly Cys Thr Ala Cys
        35                  40                  45

Thr Thr Cys Ala Cys Cys Ala Ala Cys Gly Gly Gly Ala Cys Gly Gly
    50                  55                  60

Ala Gly Cys Gly Cys Gly Thr Gly Cys Gly Gly Gly Gly Thr Gly Thr
```

-continued

```
65                    70                    75                    80

Gly Ala Cys Cys Ala Gly Ala Cys Ala Cys Ala Thr Cys Thr Ala Thr
                85                    90                    95

Ala Ala Cys Cys Gly Ala Gly Ala Gly Gly Ala Gly Thr Ala Cys Gly
                100                   105                   110

Thr Gly Cys Gly Cys Thr Thr Cys Gly Ala Cys Ala Gly Cys Gly Ala
                115                   120                   125

Cys Gly Thr Gly Gly Gly Gly Thr Gly Thr Ala Cys Cys Gly Gly
                130                   135                   140

Gly Cys Ala Gly Thr Gly Ala Cys Gly Cys Cys Gly Cys Ala Gly Gly
145                   150                   155                   160

Gly Gly Cys Gly Gly Cys Cys Thr Gly Thr Thr Gly Cys Cys Gly Ala
                165                   170                   175

Gly Thr Ala Cys Thr Gly Gly Ala Ala Cys Ala Gly Cys Gly Ala Gly
                180                   185                   190

Ala Ala Gly Gly Ala Ala Gly Thr Cys Cys Thr Gly Gly Ala Gly Gly
                195                   200                   205

Gly Gly Gly Cys Cys Gly Gly Gly Cys Gly Thr Cys Gly Gly Thr
                210                   215                   220

Gly Gly Ala Cys Ala Gly Gly Thr Gly Thr Gly Cys Ala Gly Ala
225                   230                   235                   240

Cys Ala Cys Ala Ala Cys Thr Ala Cys Gly Ala Gly Gly Thr Gly Gly
                245                   250                   255

Cys Gly Thr Ala Cys Cys Gly Cys Gly Gly Gly Ala Thr Cys Cys Thr
                260                   265                   270

Gly Cys Ala Gly Ala Gly Gly Ala Gly Ala Gly Thr Gly Gly Ala Gly
                275                   280                   285

Cys Cys Cys Ala Cys Ala Gly Thr Gly Ala Cys Cys Ala Thr Cys Thr
                290                   295                   300

Cys Cys Cys Cys Ala Thr Cys Cys Ala Gly Gly Ala Cys Ala Gly Ala
305                   310                   315                   320

Gly Gly Cys Cys Cys Thr Cys Ala Ala Cys Cys Ala Cys Ala Cys
                325                   330                   335

Ala Ala Cys Cys Thr Gly Cys Thr Gly Ala Thr Cys Thr Gly Cys Thr
                340                   345                   350

Cys Gly Gly Thr Gly Ala Cys Ala Gly Ala Thr Thr Thr Cys Thr Ala
                355                   360                   365

Thr Cys Cys Ala Ala Gly Cys Cys Ala Gly Ala Thr Cys Ala Ala Ala
                370                   375                   380

Gly Thr Cys Cys Gly Gly Thr Gly Gly Thr Thr Thr Cys Gly Gly Ala
385                   390                   395                   400

Ala Thr Gly Ala Thr Cys Ala Gly Gly Ala Gly Gly Ala Gly Ala Cys
                405                   410                   415

Ala Gly Cys Cys Gly Gly Cys Gly Thr Thr Gly Thr Gly Thr Cys Cys
                420                   425                   430

Ala Cys Cys Cys Cys Cys Cys Thr Cys Ala Thr Thr Ala Gly Gly Ala
                435                   440                   445

Ala Cys Gly Gly Thr Gly Ala Cys Thr Gly Gly Ala Cys Cys Thr Thr
                450                   455                   460

Cys Cys Ala Gly Ala Thr Cys Cys Thr Gly Gly Thr Gly Ala Thr Gly
465                   470                   475                   480

Cys Thr Gly Gly Ala Ala Ala Thr Gly Ala Cys Thr Cys Cys Cys Cys
                485                   490                   495
```

```
Ala Gly Cys Gly Thr Gly Gly Ala Gly Ala Thr Gly Thr Cys Thr Ala
        500                 505                 510

Cys Ala Cys Cys Thr Gly Cys Cys Ala Cys Gly Thr Gly Gly Ala Gly
        515                 520                 525

Cys Ala Cys Cys Cys Cys Ala Gly Cys Cys Thr Cys Cys Ala Gly Ala
        530                 535                 540

Gly Cys Cys Cys Cys Ala Thr Cys Ala Cys Cys Gly Thr Gly Gly Ala
545                 550                 555                 560

Gly Thr Gly Gly Cys Gly Gly Gly Cys Thr Cys Ala Gly Thr Cys Thr
                565                 570                 575

Gly Ala Ala Thr Cys Thr Gly Cys Cys Cys Ala Gly Ala Gly Cys Ala
        580                 585                 590

Ala Gly

<210> SEQ ID NO 3
<211> LENGTH: 198
<212> TYPE: PRT
<213> ORGANISM: Artificial Sequence
<220> FEATURE:
<223> OTHER INFORMATION: synthetic construct

<400> SEQUENCE: 3

Arg Asp Ser Pro Glu Asp Phe Val Tyr Gln Phe Lys Gly Leu Cys Tyr
1               5                   10                  15

Phe Thr Asn Gly Thr Glu Arg Val Arg Gly Val Thr Arg His Ile Tyr
                20                  25                  30

Asn Arg Glu Glu Tyr Val Arg Phe Asp Ser Asp Val Gly Val Tyr Arg
        35                  40                  45

Ala Val Thr Pro Gln Gly Arg Pro Val Ala Glu Tyr Trp Asn Ser Gln
    50                  55                  60

Lys Glu Val Leu Glu Gly Ala Arg Ala Ser Val Asp Arg Val Cys Arg
65                  70                  75                  80

His Asn Tyr Glu Val Ala Tyr Arg Gly Ile Leu Gln Arg Arg Val Glu
                85                  90                  95

Pro Thr Val Thr Ile Ser Pro Ser Arg Thr Glu Ala Leu Gln His His
                100                 105                 110

Asn Trp Leu Val Cys His Val Thr Asp Phe Tyr Pro Ser Gln Ile Lys
        115                 120                 125

Val Arg Trp Phe Arg Asn Asp Gln Glu Glu Thr Ala Gly Val Met Ser
    130                 135                 140

Thr Asn Leu Ile Arg Asn Gly Asp Trp Thr Phe Gln Ile Leu Val Met
145                 150                 155                 160

Leu Glu Met Thr Pro Gln Arg Gly Asp Val Tyr Thr Cys His Val Glu
                165                 170                 175

His Pro Ser Leu Gln Ser Pro Ile Thr Val Glu Trp Arg Ala Gln Ser
                180                 185                 190

Glu Ser Ala Gln Ser Lys
        195

<210> SEQ ID NO 4
<211> LENGTH: 267
<212> TYPE: PRT
<213> ORGANISM: Artificial Sequence
<220> FEATURE:
<223> OTHER INFORMATION: synthetic construct

<400> SEQUENCE: 4
```

-continued

```
Met Met Arg Pro Ile Val Leu Val Leu Leu Phe Ala Thr Ser Ala Leu
1               5                   10                  15

Ala Arg Asp Ser Pro Glu Asp Phe Val Tyr Gln Phe Lys Gly Leu Cys
            20                  25                  30

Tyr Phe Thr Asn Gly Thr Glu Arg Val Arg Gly Val Thr Arg His Ile
        35                  40                  45

Tyr Asn Arg Glu Glu Tyr Val Arg Phe Asp Ser Asp Val Gly Val Tyr
    50                  55                  60

Arg Ala Val Thr Pro Gln Gly Arg Pro Val Ala Glu Tyr Trp Asn Ser
65                  70                  75                  80

Gln Lys Glu Val Leu Glu Gly Ala Arg Ala Ser Val Asp Arg Val Cys
                85                  90                  95

Arg His Asn Tyr Glu Val Ala Tyr Arg Gly Ile Leu Gln Arg Arg Val
            100                 105                 110

Glu Pro Thr Val Thr Ile Ser Pro Ser Arg Thr Glu Ala Leu Gln His
            115                 120                 125

His Asn Trp Leu Val Cys His Val Thr Asp Phe Tyr Pro Ser Gln Ile
    130                 135                 140

Lys Val Arg Trp Phe Arg Asn Asp Gln Glu Glu Thr Ala Gly Val Met
145                 150                 155                 160

Ser Thr Asn Leu Ile Arg Asn Gly Asp Trp Thr Phe Gln Ile Leu Val
            165                 170                 175

Met Leu Glu Met Thr Pro Gln Arg Gly Asp Val Tyr Thr Cys His Val
            180                 185                 190

Glu His Pro Ser Leu Gln Ser Pro Ile Thr Val Glu Trp Arg Ala Gln
            195                 200                 205

Ser Glu Ser Ala Gln Ser Lys Gly Gly Gly Ser Leu Glu Ile Glu
    210                 215                 220

Ala Ala Phe Leu Glu Arg Glu Asn Thr Ala Leu Glu Thr Arg Val Ala
225                 230                 235                 240

Glu Leu Arg Gln Arg Val Gln Arg Leu Arg Asn Arg Val Ser Gln Tyr
                245                 250                 255

Arg Thr Arg Tyr Gly Pro Leu Gly Gly Gly Lys
            260                 265
```

<210> SEQ ID NO 5
<211> LENGTH: 261
<212> TYPE: PRT
<213> ORGANISM: Artificial Sequence
<220> FEATURE:
<223> OTHER INFORMATION: synthetic construct

<400> SEQUENCE: 5

```
Met Ser Trp Lys Lys Ser Leu Arg Ile Pro Gly Asp Leu Arg Val Ala
1               5                   10                  15

Thr Val Thr Leu Met Leu Ala Ile Leu Ser Ser Ser Leu Ala Glu Gly
            20                  25                  30

Arg Asp Ser Pro Glu Asp Phe Val Tyr Gln Phe Lys Gly Leu Cys Tyr
            35                  40                  45

Phe Thr Asn Gly Thr Glu Arg Val Arg Gly Val Thr Arg His Ile Tyr
        50                  55                  60

Asn Arg Glu Glu Tyr Val Arg Phe Asp Ser Asp Val Gly Val Tyr Arg
65                  70                  75                  80

Ala Val Thr Pro Gln Gly Arg Pro Val Ala Glu Tyr Trp Asn Ser Gln
                85                  90                  95
```

-continued

```
Lys Glu Val Leu Glu Gly Ala Arg Ala Ser Val Asp Arg Val Cys Arg
            100                 105                 110

His Asn Tyr Glu Val Ala Tyr Arg Gly Ile Leu Gln Arg Arg Val Glu
            115                 120                 125

Pro Thr Val Thr Ile Ser Pro Ser Arg Thr Glu Ala Leu Asn His His
            130                 135                 140

Asn Leu Leu Ile Cys Ser Val Thr Asp Phe Tyr Pro Ser Gln Ile Lys
145                 150                 155                 160

Val Arg Trp Phe Arg Asn Asp Gln Glu Glu Thr Ala Gly Val Val Ser
                165                 170                 175

Thr Pro Leu Ile Arg Asn Gly Asp Trp Thr Phe Gln Ile Leu Val Met
            180                 185                 190

Leu Glu Met Thr Pro Gln Arg Gly Asp Val Tyr Thr Cys His Val Glu
            195                 200                 205

His Pro Ser Leu Gln Ser Pro Ile Thr Val Glu Trp Arg Ala Gln Ser
            210                 215                 220

Glu Ser Ala Gln Ser Lys Met Leu Ser Gly Val Gly Gly Phe Val Leu
225                 230                 235                 240

Gly Leu Ile Phe Leu Gly Leu Gly Leu Ile Ile Arg Gln Arg Ser Arg
                245                 250                 255

Lys Gly Leu Leu His
            260

<210> SEQ ID NO 6
<211> LENGTH: 195
<212> TYPE: PRT
<213> ORGANISM: Artificial Sequence
<220> FEATURE:
<223> OTHER INFORMATION: synthetic construct

<400> SEQUENCE: 6

Glu Asp Ile Val Ala Asp His Val Ala Ser Cys Gly Val Asn Leu Tyr
1               5                   10                  15

Gln Phe Tyr Gly Pro Ser Gly Gln Tyr Thr His Glu Phe Asp Gly Asp
            20                  25                  30

Glu Glu Phe Tyr Val Asp Leu Glu Arg Lys Glu Thr Ala Trp Arg Trp
            35                  40                  45

Pro Glu Phe Ser Lys Phe Gly Gly Phe Asp Pro Gln Gly Ala Leu Arg
            50                  55                  60

Asn Met Ala Val Ala Lys His Asn Leu Asn Ile Met Ile Lys Arg Tyr
65                  70                  75                  80

Asn Ser Thr Ala Ala Thr Asn Glu Val Pro Glu Val Thr Val Phe Ser
                85                  90                  95

Lys Ser Pro Val Thr Leu Gly Gln Pro Asn Thr Leu Ile Cys Leu Val
            100                 105                 110

Asp Asn Ile Phe Pro Pro Val Val Asn Ile Thr Trp Leu Ser Asn Gly
            115                 120                 125

Gln Ser Val Thr Glu Gly Val Ser Glu Thr Ser Phe Leu Ser Lys Ser
            130                 135                 140

Asp His Ser Phe Phe Lys Ile Ser Tyr Leu Thr Phe Leu Pro Ser Ala
145                 150                 155                 160

Asp Glu Ile Tyr Asp Cys Lys Val Glu His Trp Gly Leu Asp Gln Pro
                165                 170                 175

Leu Leu Lys His Trp Glu Pro Glu Ile Pro Ala Pro Met Ser Glu Leu
            180                 185                 190
```

Thr Glu Thr
        195

<210> SEQ ID NO 7
<211> LENGTH: 585
<212> TYPE: PRT
<213> ORGANISM: Artificial Sequence
<220> FEATURE:
<223> OTHER INFORMATION: synthetic construct

<400> SEQUENCE: 7

Gly Ala Gly Gly Ala Cys Ala Thr Cys Gly Thr Gly Gly Cys Cys Gly
1               5                   10                  15

Ala Thr Cys Ala Cys Gly Thr Gly Gly Cys Ala Ala Gly Cys Thr Gly
            20                  25                  30

Cys Gly Gly Cys Gly Thr Gly Ala Ala Cys Cys Thr Gly Thr Ala Cys
        35                  40                  45

Cys Ala Gly Thr Thr Cys Thr Ala Cys Gly Gly Cys Cys Cys Cys Thr
    50                  55                  60

Cys Thr Gly Gly Cys Cys Ala Gly Thr Ala Cys Ala Cys Cys Cys Ala
65                  70                  75                  80

Thr Gly Ala Ala Thr Thr Thr Gly Ala Thr Gly Gly Ala Gly Ala Thr
                85                  90                  95

Gly Ala Gly Gly Ala Gly Thr Thr Cys Thr Ala Cys Gly Thr Gly Gly
            100                 105                 110

Ala Cys Cys Thr Gly Gly Ala Gly Ala Gly Gly Ala Ala Gly Gly Ala
            115                 120                 125

Gly Ala Cys Thr Gly Cys Cys Thr Gly Gly Cys Gly Gly Thr Gly Gly
        130                 135                 140

Cys Cys Thr Gly Ala Gly Thr Thr Cys Ala Gly Cys Ala Ala Ala Thr
145                 150                 155                 160

Thr Thr Gly Gly Ala Gly Gly Thr Thr Thr Thr Gly Ala Cys Cys Cys
                165                 170                 175

Gly Cys Ala Gly Gly Gly Thr Gly Cys Ala Cys Thr Gly Ala Gly Ala
            180                 185                 190

Ala Ala Cys Ala Thr Gly Gly Cys Thr Gly Thr Gly Gly Cys Ala Ala
            195                 200                 205

Ala Ala Cys Ala Cys Ala Ala Cys Thr Thr Gly Ala Ala Cys Ala Thr
    210                 215                 220

Cys Ala Thr Gly Ala Thr Thr Ala Ala Ala Cys Gly Cys Thr Ala Cys
225                 230                 235                 240

Ala Ala Cys Thr Cys Thr Ala Cys Cys Gly Cys Thr Gly Cys Thr Ala
            245                 250                 255

Cys Cys Ala Ala Thr Gly Ala Gly Gly Thr Thr Cys Cys Thr Gly Ala
            260                 265                 270

Gly Gly Thr Cys Ala Cys Ala Gly Thr Gly Thr Thr Thr Thr Cys Cys
        275                 280                 285

Ala Ala Gly Thr Cys Thr Cys Cys Cys Gly Thr Gly Ala Cys Ala Cys
    290                 295                 300

Thr Gly Gly Gly Thr Cys Ala Gly Cys Cys Ala Ala Cys Ala Cys
305                 310                 315                 320

Cys Cys Thr Cys Ala Thr Thr Thr Gly Thr Cys Thr Thr Gly Thr Gly
            325                 330                 335

Gly Ala Cys Ala Ala Cys Ala Thr Cys Thr Thr Thr Cys Cys Thr Cys
        340                 345                 350

-continued

```
Cys Thr Gly Thr Gly Gly Thr Cys Ala Ala Cys Ala Thr Cys Ala Cys
        355                 360                 365

Ala Thr Gly Gly Cys Thr Gly Ala Gly Cys Ala Ala Thr Gly Gly Gly
    370                 375                 380

Cys Ala Gly Thr Cys Ala Gly Thr Cys Ala Cys Ala Gly Ala Ala Gly
385                 390                 395                 400

Gly Thr Gly Thr Thr Thr Cys Thr Gly Ala Gly Ala Cys Cys Ala Gly
                405                 410                 415

Cys Thr Thr Cys Cys Thr Cys Thr Cys Cys Ala Ala Gly Ala Gly Thr
                420                 425                 430

Gly Ala Thr Cys Ala Thr Thr Cys Cys Thr Thr Cys Thr Thr Cys Ala
        435                 440                 445

Ala Gly Ala Thr Cys Ala Gly Thr Thr Ala Cys Cys Thr Cys Ala Cys
    450                 455                 460

Cys Thr Thr Cys Cys Thr Cys Cys Cys Thr Thr Cys Thr Gly Cys Thr
465                 470                 475                 480

Gly Ala Thr Gly Ala Gly Ala Thr Thr Ala Thr Gly Ala Cys Thr
                485                 490                 495

Gly Cys Ala Ala Gly Gly Thr Gly Gly Ala Gly Cys Ala Cys Thr Gly
        500                 505                 510

Gly Gly Gly Cys Cys Thr Gly Gly Ala Cys Cys Ala Gly Cys Cys Thr
        515                 520                 525

Cys Thr Thr Cys Thr Gly Ala Ala Ala Cys Ala Cys Thr Gly Gly Gly
    530                 535                 540

Ala Gly Cys Cys Thr Gly Ala Gly Ala Thr Thr Cys Cys Ala Gly Cys
545                 550                 555                 560

Cys Cys Cys Thr Ala Thr Gly Thr Cys Ala Gly Ala Gly Cys Thr Cys
                565                 570                 575

Ala Cys Ala Gly Ala Gly Ala Cys Thr
                580                 585
```

```
<210> SEQ ID NO 8
<211> LENGTH: 272
<212> TYPE: PRT
<213> ORGANISM: Artificial Sequence
<220> FEATURE:
<223> OTHER INFORMATION: synthetic construct

<400> SEQUENCE: 8

Met Met Arg Pro Ile Val Leu Val Leu Leu Phe Ala Thr Ser Ala Leu
1               5                   10                  15

Ala Glu Asp Ile Val Ala Asp His Val Ala Ser Cys Gly Val Asn Leu
            20                  25                  30

Tyr Gln Phe Tyr Gly Pro Ser Gly Gln Tyr Thr His Glu Phe Asp Gly
        35                  40                  45

Asp Glu Glu Phe Tyr Val Asp Leu Glu Arg Lys Glu Thr Ala Trp Arg
    50                  55                  60

Trp Pro Glu Phe Ser Lys Phe Gly Gly Phe Asp Pro Gln Gly Ala Leu
65                  70                  75                  80

Arg Asn Met Ala Val Ala Lys His Asn Leu Asn Ile Met Ile Lys Arg
                85                  90                  95

Tyr Asn Ser Thr Ala Ala Thr Asn Glu Val Pro Glu Val Thr Val Phe
            100                 105                 110

Ser Lys Ser Pro Val Thr Leu Gly Gln Pro Asn Thr Leu Ile Cys Leu
        115                 120                 125
```

```
Val Asp Asn Ile Phe Pro Pro Val Val Asn Ile Thr Trp Leu Ser Asn
    130             135             140

Gly Gln Ser Val Thr Glu Gly Val Ser Glu Thr Ser Phe Leu Ser Lys
145             150             155             160

Ser Asp His Ser Phe Phe Lys Ile Ser Tyr Leu Thr Phe Leu Pro Ser
                165             170             175

Ala Asp Glu Ile Tyr Asp Cys Lys Val Glu His Trp Gly Leu Asp Gln
            180             185             190

Pro Leu Leu Lys His Trp Glu Pro Glu Ile Pro Ala Pro Met Ser Glu
        195             200             205

Leu Thr Glu Thr Gly Gly Gly Gly Ser Leu Glu Ile Arg Ala Ala Phe
    210             215             220

Leu Arg Gln Arg Asn Thr Ala Leu Arg Thr Glu Val Ala Glu Leu Glu
225             230             235             240

Gln Glu Val Gln Arg Leu Glu Asn Glu Val Ser Gln Tyr Glu Thr Arg
                245             250             255

Tyr Gly Pro Leu Gly Gly Gly Lys Gly Ser His His His His His His
            260             265             270
```

<210> SEQ ID NO 9
<211> LENGTH: 17
<212> TYPE: PRT
<213> ORGANISM: Artificial Sequence
<220> FEATURE:
<223> OTHER INFORMATION: synthetic construct

<400> SEQUENCE: 9

```
Met Met Arg Pro Ile Val Leu Val Leu Leu Phe Ala Thr Ser Ala Leu
1               5               10              15

Ala
```

<210> SEQ ID NO 10
<211> LENGTH: 458
<212> TYPE: PRT
<213> ORGANISM: Artificial Sequence
<220> FEATURE:
<223> OTHER INFORMATION: synthetic construct

<400> SEQUENCE: 10

```
Met Asn Arg Gly Val Pro Phe Arg His Leu Leu Leu Val Leu Gln Leu
1               5               10              15

Ala Leu Leu Pro Ala Ala Thr Gln Gly Lys Lys Val Val Leu Gly Lys
            20              25              30

Lys Gly Asp Thr Val Glu Leu Thr Cys Thr Ala Ser Gln Lys Lys Ser
        35              40              45

Ile Gln Phe His Trp Lys Asn Ser Asn Gln Ile Lys Ile Leu Gly Asn
    50              55              60

Gln Gly Ser Phe Leu Thr Lys Gly Pro Ser Lys Leu Asn Asp Arg Ala
65              70              75              80

Asp Ser Arg Arg Ser Leu Trp Asp Gln Gly Asn Phe Pro Leu Ile Ile
                85              90              95

Lys Asn Leu Lys Ile Glu Asp Ser Asp Thr Tyr Ile Cys Glu Val Glu
            100             105             110

Asp Gln Lys Glu Glu Val Gln Leu Leu Val Phe Gly Leu Thr Ala Asn
        115             120             125

Ser Asp Thr His Leu Leu Gln Gly Gln Ser Leu Thr Leu Thr Leu Glu
    130             135             140
```

-continued

```
Ser Pro Pro Gly Ser Ser Pro Ser Val Gln Cys Arg Ser Pro Arg Gly
145             150             155             160

Lys Asn Ile Gln Gly Gly Lys Thr Leu Ser Val Ser Gln Leu Glu Leu
            165             170             175

Gln Asp Ser Gly Thr Trp Thr Cys Thr Val Leu Gln Asn Gln Lys Lys
            180             185             190

Val Glu Phe Lys Ile Asp Ile Val Val Leu Ala Phe Gln Lys Ala Ser
            195             200             205

Ser Ile Val Tyr Lys Lys Glu Gly Glu Gln Val Glu Phe Ser Phe Pro
            210             215             220

Leu Ala Phe Thr Val Glu Lys Leu Thr Gly Ser Gly Glu Leu Trp Trp
225             230             235             240

Gln Ala Glu Arg Ala Ser Ser Ser Lys Ser Trp Ile Thr Phe Asp Leu
            245             250             255

Lys Asn Lys Glu Val Ser Val Lys Arg Val Thr Gln Asp Pro Lys Leu
            260             265             270

Gln Met Gly Lys Lys Leu Pro Leu His Leu Thr Leu Pro Gln Ala Leu
            275             280             285

Pro Gln Tyr Ala Gly Ser Gly Asn Leu Thr Leu Ala Leu Glu Ala Lys
            290             295             300

Thr Gly Lys Leu His Gln Glu Val Asn Leu Val Val Met Arg Ala Thr
305             310             315             320

Gln Leu Gln Lys Asn Leu Thr Cys Glu Val Trp Gly Pro Thr Ser Pro
            325             330             335

Lys Leu Met Leu Ser Leu Lys Leu Glu Asn Lys Glu Ala Lys Val Ser
            340             345             350

Lys Arg Glu Lys Ala Val Trp Val Leu Asn Pro Glu Ala Gly Met Trp
            355             360             365

Gln Cys Leu Leu Ser Asp Ser Gly Gln Val Leu Leu Glu Ser Asn Ile
            370             375             380

Lys Val Leu Pro Thr Trp Ser Thr Pro Val Gln Pro Met Ala Leu Ile
385             390             395             400

Val Leu Gly Gly Val Ala Gly Leu Leu Leu Phe Ile Gly Leu Gly Ile
            405             410             415

Phe Phe Cys Val Arg Cys Arg His Arg Arg Arg Gln Ala Glu Arg Met
            420             425             430

Ser Gln Ile Lys Arg Leu Leu Ser Glu Lys Lys Thr Cys Gln Cys Pro
            435             440             445

His Arg Phe Gln Lys Thr Cys Ser Pro Ile
    450             455
```

```
<210> SEQ ID NO 11
<211> LENGTH: 198
<212> TYPE: PRT
<213> ORGANISM: Artificial Sequence
<220> FEATURE:
<223> OTHER INFORMATION: synthetic construct

<400> SEQUENCE: 11
```

```
Arg Asp Ser Pro Glu Asp Phe Val Tyr Gln Phe Lys Gly Leu Cys Tyr
1               5               10              15

Phe Thr Asn Gly Thr Glu Arg Val Arg Gly Val Thr Arg His Ile Tyr
            20              25              30

Asn Arg Glu Glu Tyr Val Arg Phe Asp Ser Asp Val Gly Val Tyr Arg
            35              40              45
```

-continued

```
Ala Val Thr Pro Gln Gly Arg Pro Val Ala Glu Tyr Trp Asn Ser Gln
    50                  55                  60

Lys Glu Val Leu Glu Gly Ala Arg Ala Ser Val Asp Arg Val Cys Arg
65                  70                  75                  80

His Asn Tyr Glu Val Ala Tyr Arg Gly Ile Leu Gln Arg Arg Val Glu
                85                  90                  95

Pro Thr Val Thr Ile Ser Pro Ser Arg Thr Glu Ala Leu Asn His His
                100                 105                 110

Asn Trp Leu Ile Cys Ser Val Thr Asp Phe Tyr Pro Ser Gln Ile Lys
            115                 120                 125

Val Arg Trp Phe Arg Asn Asp Gln Glu Glu Thr Ala Gly Val Met Ser
    130                 135                 140

Thr Pro Leu Ile Arg Asn Gly Asp Trp Thr Phe Gln Ile Leu Val Met
145                 150                 155                 160

Leu Glu Met Thr Pro Gln Arg Gly Asp Val Tyr Thr Cys His Val Glu
                165                 170                 175

His Pro Ser Leu Gln Ser Pro Ile Thr Val Glu Trp Arg Ala Gln Ser
            180                 185                 190

Glu Ser Ala Gln Ser Lys
            195
```

<210> SEQ ID NO 12
<211> LENGTH: 267
<212> TYPE: PRT
<213> ORGANISM: Artificial Sequence
<220> FEATURE:
<223> OTHER INFORMATION: synthetic construct

<400> SEQUENCE: 12

```
Met Met Arg Pro Ile Val Leu Val Leu Leu Phe Ala Thr Ser Ala Leu
1               5                   10                  15

Ala Arg Asp Ser Pro Glu Asp Phe Val Tyr Gln Phe Lys Gly Leu Cys
                20                  25                  30

Tyr Phe Thr Asn Gly Thr Glu Arg Val Arg Gly Val Thr Arg His Ile
            35                  40                  45

Tyr Asn Arg Glu Glu Tyr Val Arg Phe Asp Ser Asp Val Gly Val Tyr
    50                  55                  60

Arg Ala Val Thr Pro Gln Gly Arg Pro Val Ala Glu Tyr Trp Asn Ser
65                  70                  75                  80

Gln Lys Glu Val Leu Glu Gly Ala Arg Ala Ser Val Asp Arg Val Cys
                85                  90                  95

Arg His Asn Tyr Glu Val Ala Tyr Arg Gly Ile Leu Gln Arg Arg Val
                100                 105                 110

Glu Pro Thr Val Thr Ile Ser Pro Ser Arg Thr Glu Ala Leu Asn His
            115                 120                 125

His Asn Leu Leu Ile Cys Ser Val Thr Asp Phe Tyr Pro Ser Gln Ile
    130                 135                 140

Lys Val Arg Trp Phe Arg Asn Asp Gln Glu Glu Thr Ala Gly Val Val
145                 150                 155                 160

Ser Thr Pro Leu Ile Arg Asn Gly Asp Trp Thr Phe Gln Ile Leu Val
                165                 170                 175

Met Leu Glu Met Thr Pro Gln Arg Gly Asp Val Tyr Thr Cys His Val
                180                 185                 190

Glu His Pro Ser Leu Gln Ser Pro Ile Thr Val Glu Trp Arg Ala Gln
            195                 200                 205
```

-continued

```
Ser Glu Ser Ala Gln Ser Lys Gly Gly Gly Gly Ser Leu Glu Ile Glu
    210                 215                 220

Ala Ala Phe Leu Glu Arg Glu Asn Thr Ala Leu Glu Thr Arg Val Ala
225                 230                 235                 240

Glu Leu Arg Gln Arg Val Gln Arg Leu Arg Asn Arg Val Ser Gln Tyr
                245                 250                 255

Arg Thr Arg Tyr Gly Pro Leu Gly Gly Gly Lys
            260                 265

<210> SEQ ID NO 13
<211> LENGTH: 267
<212> TYPE: PRT
<213> ORGANISM: Artificial Sequence
<220> FEATURE:
<223> OTHER INFORMATION: synthetic construct

<400> SEQUENCE: 13

Met Met Arg Pro Ile Val Leu Val Leu Leu Phe Ala Thr Ser Ala Leu
1               5                   10                  15

Ala Arg Asp Ser Pro Glu Asp Phe Val Tyr Gln Phe Lys Gly Leu Cys
                20                  25                  30

Tyr Phe Thr Asn Gly Thr Glu Arg Val Arg Gly Val Thr Arg His Ile
            35                  40                  45

Tyr Asn Arg Glu Glu Tyr Val Arg Phe Asp Ser Asp Val Gly Val Tyr
    50                  55                  60

Arg Ala Val Thr Pro Gln Gly Arg Pro Val Ala Glu Tyr Trp Asn Ser
65                  70                  75                  80

Gln Lys Glu Val Leu Glu Gly Ala Arg Ala Ser Val Asp Arg Val Cys
                85                  90                  95

Arg His Asn Tyr Glu Val Ala Tyr Arg Gly Ile Leu Gln Arg Arg Val
            100                 105                 110

Glu Pro Thr Val Thr Ile Ser Pro Ser Arg Thr Glu Ala Leu Asn His
            115                 120                 125

His Asn Trp Leu Ile Cys Ser Val Thr Asp Phe Tyr Pro Ser Gln Ile
    130                 135                 140

Lys Val Arg Trp Phe Arg Asn Asp Gln Glu Glu Thr Ala Gly Val Met
145                 150                 155                 160

Ser Thr Pro Leu Ile Arg Asn Gly Asp Trp Thr Phe Gln Ile Leu Val
                165                 170                 175

Met Leu Glu Met Thr Pro Gln Arg Gly Asp Val Tyr Thr Cys His Val
            180                 185                 190

Glu His Pro Ser Leu Gln Ser Pro Ile Thr Val Glu Trp Arg Ala Gln
            195                 200                 205

Ser Glu Ser Ala Gln Ser Lys Gly Gly Gly Gly Ser Leu Glu Ile Glu
    210                 215                 220

Ala Ala Phe Leu Glu Arg Glu Asn Thr Ala Leu Glu Thr Arg Val Ala
225                 230                 235                 240

Glu Leu Arg Gln Arg Val Gln Arg Leu Arg Asn Arg Val Ser Gln Tyr
                245                 250                 255

Arg Thr Arg Tyr Gly Pro Leu Gly Gly Gly Lys
            260                 265

<210> SEQ ID NO 14
<211> LENGTH: 12
<212> TYPE: PRT
<213> ORGANISM: Artificial Sequence
```

-continued

```
<220> FEATURE:
<223> OTHER INFORMATION: synthetic construct

<400> SEQUENCE: 14

Cys Ala Leu Tyr Thr Asn Ala Gly Lys Ser Thr Phe
1               5                   10

<210> SEQ ID NO 15
<211> LENGTH: 15
<212> TYPE: PRT
<213> ORGANISM: Artificial Sequence
<220> FEATURE:
<223> OTHER INFORMATION: synthetic construct

<400> SEQUENCE: 15

Cys Ala Thr Ser Arg Asp Val Ser Ser Thr Asp Thr Gln Tyr Phe
1               5                   10                  15
```

1

MHC CLASS II MOLECULES AND METHODS OF USE THEREOF

CROSS REFERENCE TO RELATED APPLICATIONS

This PCT application claims the priority benefit of U.S. Provisional Application Nos. 62/880,501, filed Jul. 30, 2019, and 63/029,114, filed May 22, 2020, each of which is incorporated herein by reference in its entirety.

REFERENCE TO SEQUENCE LISTING SUBMITTED ELECTRONICALLY VIA EFS-WEB

The content of the electronically submitted sequence listing (Name: 4285-011PC02_SL_ST25.txt, Size: 34,403 bytes; and Date of Creation: Jul. 28, 2020) is incorporated herein by reference in its entirety.

FIELD OF THE DISCLOSURE

The present disclosure provides major histocompatibility complex (MHC) class II molecules with increased affinity for CD4 and uses thereof.

BACKGROUND OF THE DISCLOSURE

Immunotherapy has emerged as a critical tool in the battle against a variety of diseases, including cancer. T cell therapies are at the forefront of immunotherapeutic development, and adoptive transfer of antitumor T cells has been shown to induce clinical responses in cancer patients.

Directed T cell therapy using T cells expression T cell receptors (TCRs) specific for a target epitope expressed by tumor cells is a promising form of T cell therapy. Antigen presenting cells display peptide fragments associated with the major histocompatibility complex (MHC) on their surface to induce an immune response. It has been demonstrated that the improved presentation of endogenous peptides via class II is correlated with improved survival of cancer patients. However, the development of novel TCRs capable of specifically targeting MHC class II presented peptides is hindered by the low affinity of MHC class II proteins for CD4 expressed by T cells.

The present disclosure provides MHC class II proteins with increased affinity for CD4 and methods of using the same for the identification and development of novel MHC class II-specific TCRs.

SUMMARY OF THE DISCLOSURE

Certain aspects of the present disclosure are directed to an HLA class II molecule comprising a DQ beta chain, wherein the DQ beta chain comprises an amino acid other than leucine at a position corresponding to amino acid residue 114 of SEQ ID NO: 1.

Certain aspects of the present disclosure are directed to an HLA class II molecule comprising a DQ beta chain, wherein the DQ beta chain comprises a substitution mutation at a position corresponding to amino acid residue 114 of SEQ ID NO: 1, wherein the substitution mutation is with an amino acid other than leucine.

In some aspects, the DQ beta chain further comprises an amino acid other than valine at a position corresponding to amino acid residue 143 of SEQ ID NO: 1.

Certain aspects of the present disclosure are directed to an HLA class II molecule comprising a DQ beta chain, wherein the DQ beta chain comprises an amino acid other than valine at a position corresponding to amino acid residue 143 of SEQ ID NO: 1.

Certain aspects of the present disclosure are directed to an HLA class II molecule comprising a DQ beta chain, wherein the DQ beta chain comprises a substitution mutation at a position corresponding to amino acid residue 143 of SEQ ID NO: 1, wherein the substitution mutation is with an amino acid other than valine.

In some aspects, the DQ beta chain further comprises an amino acid other than leucine at a position corresponding to amino acid residue 114 of SEQ ID NO: 1. In some aspects, the DQ beta chain further comprises an amino acid other than asparagine at a position corresponding to amino acid residue 110 of SEQ ID NO: 1. In some aspects, the DQ beta chain further comprises an amino acid other than isoleucine at a position corresponding to amino acid residue 116 of SEQ ID NO: 1. In some aspects, the DQ beta chain further comprises an amino acid other than serine at a position corresponding to amino acid residue 118 of SEQ ID NO: 1. In some aspects, the DQ beta chain further comprises an amino acid other than proline at a position corresponding to amino acid residue 146 of SEQ ID NO: 1.

In some aspects, the DQ beta chain further comprises at least three of: (i) an amino acid other than asparagine at a position corresponding to amino acid residue 110 of SEQ ID NO: 1, (ii) an amino acid other than isoleucine at a position corresponding to amino acid residue 116 of SEQ ID NO: 1, (iii) an amino acid other than serine at a position corresponding to amino acid residue 118 of SEQ ID NO: 1, and (iv) an amino acid other than proline at a position corresponding to amino acid residue 146 of SEQ ID NO: 1.

In some aspects, the DQ beta chain further comprises: (i) an amino acid other than asparagine at a position corresponding to amino acid residue 110 of SEQ ID NO: 1, (ii) an amino acid other than isoleucine at a position corresponding to amino acid residue 116 of SEQ ID NO: 1, (iii) an amino acid other than serine at a position corresponding to amino acid residue 118 of SEQ ID NO: 1, and (iv) an amino acid other than proline at a position corresponding to amino acid residue 146 of SEQ ID NO: 1.

In some aspects, the amino acid other than leucine at a position corresponding to amino acid residue 114 of SEQ ID NO: 1 comprises a hydrophobic side chain. In some aspects, the amino acid other than leucine at a position corresponding to amino acid residue 114 of SEQ ID NO: 1 is selected from the group consisting of an alanine, a valine, an isoleucine, a methionine, a phenylalanine, a tyrosine, and a tryptophan. In some aspects, the amino acid other than leucine at a position corresponding to amino acid residue 114 of SEQ ID NO: 1 is a tryptophan.

In some aspects, the amino acid other than valine at a position corresponding to amino acid residue 143 of SEQ ID NO: 1 comprises a hydrophobic side chain. In some aspects, the amino acid other than valine at a position corresponding to amino acid residue 143 of SEQ ID NO: 1 is selected from an alanine, an isoleucine, a leucine, a methionine, a phenylalanine, a tyrosine, and a tryptophan. In some aspects, the amino acid other than valine at a position corresponding to amino acid residue 143 of SEQ ID NO: 1 is a methionine.

In some aspects, the beta chain of the MHC class II molecule comprises an amino acid other than asparagine at a position corresponding to amino acid residue 110 of SEQ ID NO: 1. In some aspects, the amino acid other than asparagine at a position corresponding to amino acid residue 110 of SEQ ID NO: 1 is selected from a serine, a threonine, and a glutamine. In some aspects, the amino acid other than asparagine at a position corresponding to amino acid residue 110 of SEQ ID NO: 1 is a glutamine.

In some aspects, the beta chain of the MHC class II molecule comprises an amino acid other than isoleucine at a position corresponding to amino acid residue 116 of SEQ ID NO: 1. In some aspects, the amino acid other than isoleucine at a position corresponding to amino acid residue 116 of SEQ ID NO: 1 is selected from an alanine, a valine, a leucine, a methionine, a phenylalanine, a tyrosine, and a tryptophan. In some aspects, the amino acid other than isoleucine at a position corresponding to amino acid residue 116 of SEQ ID NO: 1 is valine.

In some aspects, the beta chain of the MHC class II molecule comprises an amino acid other than serine at a position corresponding to amino acid residue 118 of SEQ ID NO: 1. In some aspects, the amino acid other than serine at a position corresponding to amino acid residue 118 of SEQ ID NO: 1 is selected from an arginine, a histidine, and a lysine. In some aspects, the amino acid other than serine at a position corresponding to amino acid residue 118 of SEQ ID NO: 1 is a histidine.

In some aspects, the beta chain of the MHC class II molecule comprises an amino acid other than proline at a position corresponding to amino acid residue 146 of SEQ ID NO: 1. In some aspects, the amino acid other than proline at a position corresponding to amino acid residue 146 of SEQ ID NO: 1 is selected from a serine, a threonine, an asparagine, and a glutamine. In some aspects, the amino acid other than proline at a position corresponding to amino acid residue 146 of SEQ ID NO: 1 is a glutamine.

In some aspects, the DQ beta chain comprises an amino acid sequence having at least about 80%, at least about 85%, at least about 90%, at least about 95%, at least about 96%, at least about 97%, at least about 98%, or at least about 99% sequence identity to an amino acid sequence selected from SEQ ID NOs: 1, 3, 4, and 5.

In some aspects, the DQ beta chain comprises a tryptophan at a position corresponding to amino acid residue 114 of SEQ ID NO: 1 and a methionine at a position corresponding to amino acid residue 143 of SEQ ID NO: 1.

In some aspects, the beta chain of the MHC class II molecule comprises (a) a tryptophan at a position corresponding to amino acid residue 114 of SEQ ID NO: 1; (b) a methionine at a position corresponding to amino acid residue 143 of SEQ ID NO: 1; and (c) at least one of: (i) a glutamine at a position corresponding to amino acid residue 110 of SEQ ID NO: 1; (ii) a valine at a position corresponding to amino acid residue 116 of SEQ ID NO: 1, (iii) a histidine at a position corresponding to amino acid residue 118 of SEQ ID NO: 1, and (iv) a glutamine at a position corresponding to amino acid residue 146 of SEQ ID NO: 1.

In some aspects, the beta chain of the MHC class II molecule comprises (a) a tryptophan at a position corresponding to amino acid residue 114 of SEQ ID NO: 1; (b) a methionine at a position corresponding to amino acid residue 143 of SEQ ID NO: 1; and (c) at least two of: (i) a glutamine at a position corresponding to amino acid residue 110 of SEQ ID NO: 1; (ii) a valine at a position corresponding to amino acid residue 116 of SEQ ID NO: 1, (iii) a histidine at a position corresponding to amino acid residue 118 of SEQ ID NO: 1, and (iv) a glutamine at a position corresponding to amino acid residue 146 of SEQ ID NO: 1.

In some aspects, the beta chain of the MHC class II molecule comprises (a) a tryptophan at a position corresponding to amino acid residue 114 of SEQ ID NO: 1; (b)

a methionine at a position corresponding to amino acid residue 143 of SEQ ID NO: 1; and (c) at least three of: (i) a glutamine at a position corresponding to amino acid residue 110 of SEQ ID NO: 1; (ii) a valine at a position corresponding to amino acid residue 116 of SEQ ID NO: 1, (iii) a histidine at a position corresponding to amino acid residue 118 of SEQ ID NO: 1, and (iv) a glutamine at a position corresponding to amino acid residue 146 of SEQ ID NO: 1.

In some aspects, the beta chain of the MHC class II molecule comprises (a) a tryptophan at a position corresponding to amino acid residue 114 of SEQ ID NO: 1; (b) a methionine at a position corresponding to amino acid residue 143 of SEQ ID NO: 1; (c) a glutamine at a position corresponding to amino acid residue 110 of SEQ ID NO: 1; (d) a valine at a position corresponding to amino acid residue 116 of SEQ ID NO: 1, (e) a histidine at a position corresponding to amino acid residue 118 of SEQ ID NO: 1, and (f) a glutamine at a position corresponding to amino acid residue 146 of SEQ ID NO: 1.

In some aspects, the DQ beta chain comprises the amino acid sequence set forth in SEQ ID NO: 3. In some aspects, the DQ beta chain comprises the amino acid sequence set forth in SEQ ID NO: 4.

In some aspects, the beta chain of the HLA class II molecule comprises a DQ2, DQ3, DQ4, DQ5, or DQ6 allele. In some aspects, the beta chain of the MHC class II molecule comprises an HLA-DQB1*02, HLA-DQB1*03, HLA-DQB1*04, HLA-DQB1*05, or HLA-DQB1*06 allele.

In some aspects, the HLA class II molecule further comprises a DQ alpha chain. In some aspects, the alpha chain of the MHC class II molecule comprises an HLA-DQA1*01, HLA-DQA1*02, HLA-DQA1*03, HLA-DQA1*04, HLA-DQA1*05, or HLA-DQA1*06 allele.

In some aspects, the DQ alpha chain comprises an amino acid sequence having at least about 80%, at least about 85%, at least about 90%, at least about 95%, at least about 96%, at least about 97%, at least about 98%, or at least about 99% sequence identity to SEQ ID NO: 6 or 8. In some aspects, the DQ alpha chain comprises the amino acid sequence set forth in SEQ ID NO: 6 or 8.

In some aspects, the DQ beta chain has an increased affinity for a CD4 protein as compared to a reference HLA class II molecule, wherein the reference HLA class II molecule comprises a DQ beta chain comprising (i) a leucine at a position corresponding to amino acid residue 114 of SEQ ID NO: 1 and/or (ii) a valine at a position corresponding to amino acid residue 143 of SEQ ID NO: 1.

In some aspects, the increased affinity is at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, or at least about 1000.

In some aspects, the DQ beta chain is bound to a membrane of a cell. In some aspects, the DQ beta chain is not bound to a membrane of a cell. In some aspects, the DQ beta chain comprises an extracellular domain of a full length DQ alpha chain. In some aspects, the DQ beta chain does not comprise a transmembrane domain of a full length DQ beta chain.

In some aspects, the DQ alpha chain is bound to a membrane of a cell. In some aspects, the DQ alpha chain is not bound to a membrane of a cell. In some aspects, the DQ alpha chain comprises an extracellular domain of a full length DQ alpha chain. In some aspects, the DQ alpha chain does not comprise a transmembrane domain of a full length DQ alpha chain.

In some aspects, the DQ beta chain is linked to or associated with an inert particle. In some aspects, the inert particle is a bead. In some aspects, the inert particle is a nanoparticle. In some aspects, the nanoparticle is selected from a pegylated iron oxide, chitosan, dextrane, gelatin, alginate, liposome, starch, branched polymer, carbon-based carrier, polylactic acid, poly(cyano)acrylate, polyethyleinemine, block copolymer, ply caprolactone, SPIONS, USPIONS, Cd/Zn-selenide, or silica nanoparticle. In some aspects, the nanoparticle is a pegylated iron oxide nanoparticle.

In some aspects, the DQ beta chain comprises a signal peptide. In some aspects, the DQ alpha chain comprises a signal peptide. In some aspects, the signal peptide comprises the amino acid sequence set forth in SEQ ID NO: 9.

Certain aspects of the present disclosure are directed to a nucleic acid molecule encoding a DQ beta chain disclosed herein. In some aspects, the nucleic acid molecule further encodes a DQ alpha chain disclosed herein.

In some aspects, the nucleic acid molecule comprises a nucleotide sequence having at least about 70%, at least about 75%, at least about 80%, at least about 85%, at least about 90%, at least about 95%, at least about 96%, at least about 97%, at least about 98%, or at least about 99% sequence identity to SEQ ID NO: 2.

Certain aspects of the present disclosure are directed to a vector comprising a nucleic acid molecule disclosed herein.

Certain aspects of the present disclosure are directed to a cell comprising an HLA class II molecule disclosed herein, a nucleic acid molecule disclosed herein, or a vector disclosed herein. In some aspects, the cell is a mammalian cell or an insect cell. In some aspects, the cell is selected from a K562 cell, T2, HEK293, HEK293T, A375, SK-MEL-28, Me275, COS, a fibroblast cell, a tumor cell, or any combination thereof. In some aspects, the cell lacks endogenous MHC class II DQ beta chain expression. In some aspects, the cell lacks endogenous MHC class II DQ alpha chain expression.

Certain aspects of the present disclosure are directed to a method of identifying a T cell receptor capable of binding an epitope in an MHC class II complex, comprising pulsing a cell disclosed herein with one or more peptide comprising the epitope, and stimulating one or more CD4+ T cell with the APC.

Certain aspects of the present disclosure are directed to a method of treating a disease or condition in a subject in need thereof, comprising administering to the subject a MHC class II molecule disclosed herein. In some aspects, the disease or condition is cancer or an infection.

In some aspects, the cancer is selected from the group consisting of melanoma, bone cancer, pancreatic cancer, skin cancer, cancer of the head or neck, uterine cancer, ovarian cancer, rectal cancer, stomach cancer, uterine cancer, lung cancer, Hodgkin's Disease, non-Hodgkin's lymphoma (NHL), cancer of the esophagus, cancer of the small intestine, cancer of the urethra, chronic or acute leukemia, acute myeloid leukemia, chronic myeloid leukemia, acute lymphoblastic leukemia (ALL) (including non T cell ALL), chronic lymphocytic leukemia (CLL), cancer of the bladder, cancer of the kidney or ureter, carcinoma of the renal pelvis, glioma, squamous cell cancer, and combinations of said cancers.

In some aspects, the cancer is relapsed or refractory. In some aspects, the cancer is locally advanced. In some aspects, the cancer is advanced. In some aspects, the cancer is metastatic.

In some aspects, the HLA class II molecule binds CD4 with a $K_D$ of less than about 100 µM. In some aspects, the HLA class II molecule binds CD4 with a $K_D$ of less than about 10 µM. In some aspects, the HLA class II molecule binds CD4 with a $K_D$ of about 8.9 µM or less.

Certain aspects of the disclosure are directed to a complex comprising an HLA class II molecule disclosed herein and a peptide, wherein the peptide comprises $DDX3Y_{171-190}$, $HA_{255-270}$, $GPC3_{138-157}$, or any combination thereof.

BRIEF DESCRIPTION OF THE DRAWINGS

FIGS. 1A-1F provide data illustrating the enhanced CD4 binding ability of modified DQ molecules. FIG. 1A is a table comparing the amino acid sequences of DPB1*04:01, DQB1*05:01, and $DQB1*05:01^{L114W/V143M+4reps}$ with mutated amino acids underlined. FIGS. 1B and 1C are graphical representations of data of class II-deficient K562 cells stably expressing wild-type DQ5 (DQA1*01:01/DQB1*05:01), $DQ5^{L114W/V143M}DQ5^{L114W/V143M+4reps}$, wild-type DP4, or $DP4^{L112W/V141M}$ stained with sCD4, as shown in FIG. 1A. FIG. 1D shows the CD4 binding ability of a series of K562 derivatives individually expressing $DQ5^{L114W/V143M+4reps}$ mutants with a single amino acid reversal at one of the four positions, similarly stained with sCD4. FIG. 1E is a table listing the amino acid sequences of DPB1*04:01, DQB1*02:01, DQB1*04:02 and DQB1*06:01 with replaced amino acids underlined. Note that unlike DQB1*05:01, DQB1*02:01, DQB1*04:02 and DQB1*06:01 encode Val at position 116, similar to DPB1*04:01, which codes for Val at position 114. FIG. 1F provides graphical representations of data showing that the L114W/V143M+3reps replacements in the β chains enhanced the binding of DQ2, DQ4, and DQ6 to CD4. At least 2 independent experiments were performed. *, P<0.05 by Student's t-test. Bars and error bars represent the mean±SD of results in triplicate experiments.

FIGS. 3A-Q are graphical representations of histograms illustrating the comparable expression levels of HLA class II genes. HLA-DQ and their derivatives were reconstituted in K562 cells and stained with anti-HLA class II monoclonal antibodies. The surface expression of each DQ2, DQ5, and DQ6 allele was detected using the anti-HLA class II monoclonal antibody clone 9-49(I3) (DQ5 and DQ6) or the anti-class II monoclonal antibody clone T639 (DQ2 and DQ4). Open histograms represent the isotype control staining.

FIGS. 4A-4L are graphical representations showing that $DQ5^{L114W/V143M+4reps}$ dimers robustly stained E6-transduced CD4+ T cells. E6 was reconstituted in CD4⁺ T cells, which were then stained with wild-type DQ5 (FIGS. 4D and 4J), $DQ5^{L114W/V143M}$ (FIGS. 4E and 4K), and $DQ5^{L114W/V143M+4reps}$ (FIGS. 4F and 4L) CLIP control dimers (FIGS. 4D-4F) and dimers specific to $DDX3Y_{171-190}$(FIGS. 4J-4L). Control cells not transduced with a TCR are shown in FIGS. 4A-4C and 4G-4I.

FIGS. 5A-5G are graphical representations showing cloning of DQ5-restricted TCR using affinity matured dimer. Primary CD4$^+$ T cells were purified from a DQ5.1$^+$ melanoma patient and stimulated with irradiated $GPC3_{138-57}$-pulsed aAPCs expressing DQ5.1. Two weeks later, stimulated CD4$^+$ T cells were stained with cognate $GPC3_{138-157}$-$DQ5^{L114W/V143M+4reps}$ dimers (FIGS. 5A-5B). The GPC3 specific TCR was reconstituted in TCR-defective Jurkat 76/CD4 cells, and stained by the respective $DQ5^{L114W/V143M+4reps}$ dimers (FIG. 5C (E6/Control); FIG. 5D (E6/GPC3$_{138-157}$); FIG. 5E (DQ5-06-GPC3$_{138-157}$/Control); and FIG. 5F (DQ5-06-GPC3$_{138-157}$/GPC3$_{138-157}$)). Jurkat 76/CD4 cells expressing the GPC3 specific TCR were stimulated by DQ5-K562 cells pulsed with the respective peptides in IL-2 ELISPOT assays (FIG. 5G).

DETAILED DESCRIPTION OF THE DISCLOSURE

Figure 1A:
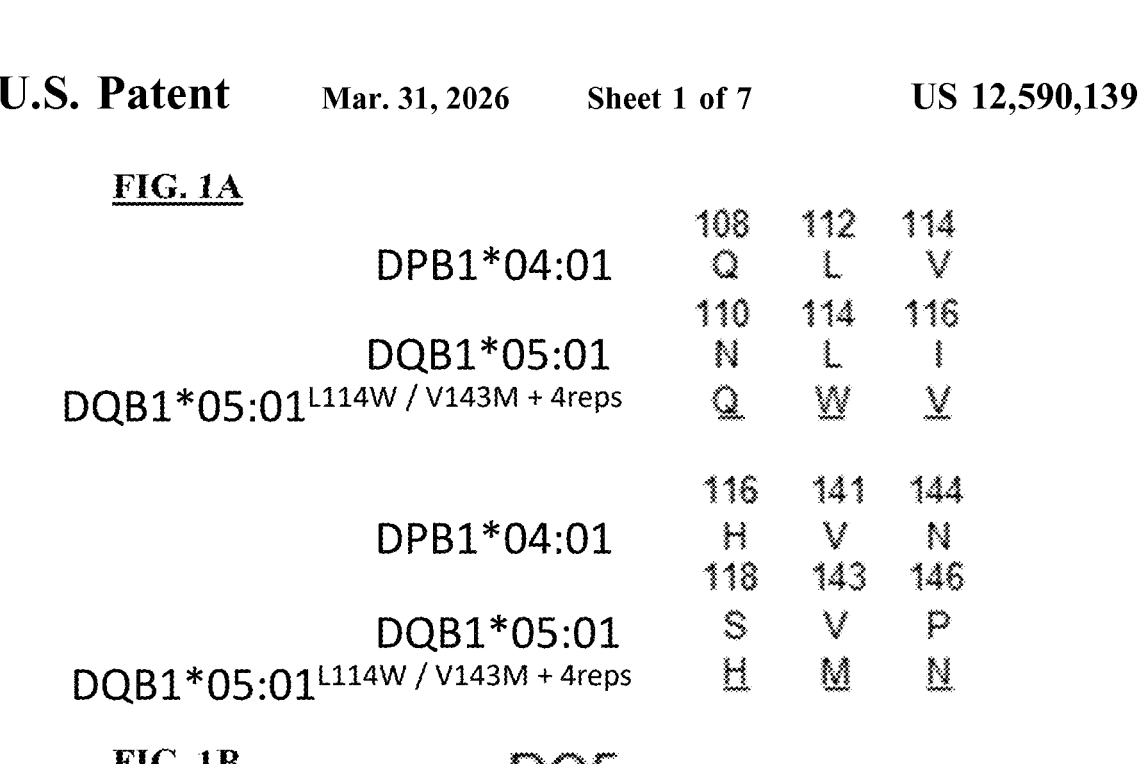

The present disclosure is directed to MHC class II molecules with increased affinity for CD4. In some aspects, the present disclosure is directed to MHC class II molecules comprising an HLA-DQ (DQ) beta chain, wherein the DQ beta chain has increased affinity for CD4.

The present disclosure is further directed to MHC class II molecules comprising a DQ beta chain, wherein the DQ beta chain comprises an amino acid other than leucine at a position corresponding to amino acid residue 114 of SEQ ID NO: 1. In some aspects, the DQ beta chain further comprises an amino acid other than valine at a position corresponding to amino acid residue 143 of SEQ ID NO: 1.

The present disclosure is further directed to MHC class II molecules comprising a DQ beta chain, wherein the DQ beta chain comprises an amino acid other than valine at a position corresponding to amino acid residue 143 of SEQ ID NO: 1. In some aspects, the DQ beta chain further comprises an amino acid other than leucine at a position corresponding to amino acid residue 114 of SEQ ID NO: 1.

In some aspects, the DQ beta chain further comprises at least three of: (i) an amino acid other than asparagine at a position corresponding to amino acid residue 110 of SEQ ID NO: 1, (ii) an amino acid other than isoleucine at a position corresponding to amino acid residue 116 of SEQ ID NO: 1, (iii) an amino acid other than serine at a position corresponding to amino acid residue 118 of SEQ ID NO: 1, and (iv) an amino acid other than proline at a position corresponding to amino acid residue 146 of SEQ ID NO: 1.

I. Terms

In order that the present disclosure can be more readily understood, certain terms are first defined. As used in this application, except as otherwise expressly provided herein, each of the following terms shall have the meaning set forth below. Additional definitions are set forth throughout the application.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some aspects, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "HLA," as used herein, refers to the human leukocyte antigen. HLA genes encode the major histocompatibility complex (MHC) proteins in humans. MHC proteins are expressed on the surface of cells, and are involved in activation of the immune response. HLA class II genes encode MHC class II proteins which are expressed on the surface of professional antigen presenting cells (APCs). Non-limiting examples of professional APCs include monocytes, macrophages, dendritic cells (DCs), and B lymphocytes. Some endothelial and epithelial cells can also express MHC class II molecules after inflammatory signals are activated. Humans lacking functional MHC class II molecules are extremely susceptible to an array of infectious diseases and typically die at a young age.

As used herein, an "HLA class II molecule" or "MHC class II molecule" refers to a protein product of a wild-type or variant HLA class II gene encoding an MHC class II molecule. Accordingly, "HLA class II molecule" and "MHC class II molecule" are used interchangeably herein. A typical MHC Class II molecule comprises two protein chains: an alpha chain and a beta chain. In general, naturally occurring alpha chains and beta chains each comprise a transmembrane domain, which anchors the alpha/beta chain to the cell surface, and an extracellular domain, which carries the antigen and interacts with a TCR and/or CD4 expressed on a T cell.

Both the MHC Class II alpha and beta chains are encoded by the HLA gene complex. The HLA complex is located within the 6p21.3 region on the short arm of human chromosome 6 and contains more than 220 genes of diverse function. The HLA gene complex is highly variant, with over 20,000 HLA alleles and related alleles, including over 250 MHC class II alpha chain alleles and 5,000 MHC class II beta chain alleles, known in the art, encoding thousands of MHC class II proteins (see, e.g., hla.alleles.org, last visited May 20, 2019, which is incorporated by reference herein in its entirety). For example one such HLA-DP allele, DP4 is the most frequently found allele in many ethnic groups. Each alpha chain and beta chain is typically expressed as a proprotein, which further comprises a signal peptide that is cleaved off. Any number of naturally occurring signal peptides can be used to facilitate expression and localization of the alpha chains and beta chains disclosed herein. One such example is SEQ TD NO: 9.

Three loci in the HLA complex encode MHC Class II proteins: HLA-DP, HLA-DQ, and HLA-DR. HLA-DO and HLA-DM encode proteins that associate with the MHC class II molecule and support its configuration and function. Representative HLA-DQ sequences are provided in Table 1.

TABLE 1

| DQ Beta chain and alpha chain amino acid and nucleotide sequences. |
| --- |

Beta Chain
DQB1*05:01 Extracellular Domain (SEQ ID NO: 1)
RDSPEDFVYQFKGLCYFTNGTERVRGVTRHIYNREEYVRFDSDVGVYRAVTPQGRPVAEYWNSQKEVLEGARAS
VDRVCRHNYEVAYRGILQRRVEPTVTISPSRTEALNHHNLLICSVTDFYPSQIKVRWFRNDQEETAGVVSTPLI
RNGDWTFQILVMLEMTPQRGDVYTCHVEHPSLQSPITVEWRAQSESAQSK DQB1*05:01 Extracellular Domain (SEQ ID NO: 2)
AGAGACTCTCCCGAGGATTTCGTGTACCAGTTTAAGGGCCTGTGCTACTTCACCAACGGGACGGAGCGCGTGCG
GGGTGTGACCAGACACATCTATAACCGAGAGGAGTACGTGCGCTTCGACAGCGACGTGGGGGTGTACCGGGCAG
TGACGCCGCAGGGGCGGCCTGTTGCCGAGTACTGGAACAGCCAGAAGGAAGTCCTGGAGGGGGCCCGGGCGTCG
GTGGACAGGGTGTGCAGACACAACTACGAGGTGGCGTACCGCGGGATCCTGCAGAGGAGAGTGGAGCCCACAGT
GACCATCTCCCCATCCAGGACAGAGGCCCTCAACCACCACAACCTGCTGATCTGCTCGGTGACAGATTTCTATC
CAAGCCAGATCAAAGTCCGGTGGTTTCGGAATGATCAGGAGGAGACAGCCGGCGTTGTGTCCACCCCCCTCATT
AGGAACGGTGACTGGACCTTCCAGATCCTGGTGATGCTGGAAATGACTCCCCAGCGTGGAGATGTCTACACCTG
CCACGTGGAGCACCCCAGCCTCCAGAGCCCCATCACCGTGGAGTGGCGGGCTCAGTCTGAATCTGCCCAGAGCA
AG DQB1*05:01 L114W/V143M Extracellular Domain (SEQ ID NO: 11)
RDSPEDFVYQFKGLCYFTNGTERVRGVTRHIYNREEYVRFDSDVGVYRAVTPQGRPVAEYWNSQKEVLEGARAS
VDRVCRHNYEVAYRGILQRRVEPTVTISPSRTEALNHHNWLICSVTDFYPSQIKVRWFRNDQEETAGVMSTPLI
RNGDWTFQILVMLEMTPQRGDVYTCHVEHPSLQSPITVEWRAQSESAQSK DQB1*05:01 L114W/V143M + 4 Reps Extracellular Domain (SEQ ID NO: 3)
RDSPEDFVYQFKGLCYFTNGTERVRGVTRHIYNREEYVRFDSDVGVYRAVTPQGRPVAEYWNSQKEVLEGARAS
VDRVCRHNYEVAYRGILQRRVEPTVTISPSRTEALQHHNWLVCHVTDFYPSQIKVRWFRNDQEETAGVMSTNLI
RNGDWTFQILVMLEMTPQRGDVYTCHVEHPSLQSPITVEWRAQSESAQSK Signal Peptide; DQB1*05:01 Domain; Gly/Ser Linker; Zip Sequences and His
tag sequences) (SEQ ID NO: 12)
MMRPIVLVLLFATSALARDSPEDFVYQFKGLCYFTNGTERVRGVTRHIYNREEYVRFDSDVGVYRAVTPQGRPV
AEYWNSQKEVLEGARASVDRVCRHNYEVAYRGILQRRVEPTVTISPSRTEALNHHNLLICSVTDFYPSQIKVRW
FRNDQEETAGVVSTPLIRNGDWTFQILVMLEMTPQRGDVYTCHVEHPSLQSPITVEWRAQSESAQSKGGGGSLE
IEAAFLERENTALETRVAELRQRVQRLRNRVSQYRTRYGPLGGGK Signal Peptide; DQB1*05:01 L114W/V143M Domain; Gly/Ser Linker; Zip
Sequences and His tag sequences) (SEQ ID NO: 13)
MMRPIVLVLLFATSALARDSPEDFVYQFKGLCYFTNGTERVRGVTRHIYNREEYVRFDSDVGVYRAVTPQGRPV
AEYWNSQKEVLEGARASVDRVCRHNYEVAYRGILQRRVEPTVTISPSRTEALNHHNWLICSVTDFYPSQIKVRW
FRNDQEETAGVMSTPLIRNGDWTFQILVMLEMTPQRGDVYTCHVEHPSLQSPITVEWRAQSESAQSKGGGGSLE
IEAAFLERENTALETRVAELRQRVQRLRNRVSQYRTRYGPLGGGK Signal Peptide; DQB1*05:01 L114W/V143M + 4 Reps Extracellular Domain;
Gly/Ser Linker; Zip Sequences and His tag sequences) (SEQ ID NO: 4)
MMRPIVLVLLFATSALARDSPEDEVYQFKGLCYFTNGTERVRGVTRHIYNREEYVREDSDVGVYRAVTPQGRPV
AEYWNSQKEVLEGARASVDRVCRHNYEVAYRGILQRRVEPTVTISPSRTEALQHHNWLVCHVTDFYPSQIKVRW TABLE 1-continued DQ Beta chain and alpha chain amino acid and nucleotide sequences.

*FRNDQEETAGVMSTNLIRNGDWTFQILVMLEMTPQRGDVYTCHVEHPSLQSPITVEWRAQSESAQSK*GGGGSLE
IEAAFLERENTALETRVAELRQRVQRLRNRVSQYRTRYGPLGGGK

Full-length wild-type DQB1*05:01 (SEQ ID NO: 5)
MSWKKSLRIPGDLRVATVTLMLAILSSSLAEGRDSPEDFVYQFKGLCYFTNGTERVRGVTRHIYNREEYVRFDS
DVGVYRAVTPQGRPVAEYWNSQKEVLEGARASVDRVCRHNYEVAYRGILQRRVEPTVTISPSRTEALNHHNLLI
CSVTDFYPSQIKVRWFRNDQEETAGVVSTPLIRNGDWTFQILVMLEMTPQRGDVYTCHVEHPSLQSPITVEWRA
QSESAQSKMLSGVGGFVLGLIFLGLGLIIRQRSRKGLLH Alpha Chain
DQA1*01:01 Extracellular Domain (SEQ ID NO: 6)
EDIVADHVASCGVNLYQFYGPSGQYTHEFDGDEEFYVDLERKETAWRWPEFSKFGGFDPQGALRNMAVAKHNLN
IMIKRYNSTAATNEVPEVTVFSKSPVTLGQPNTLICLVDNIFPPVVNITWLSNGQSVTEGVSETSFLSKSDHSF
FKISYLTFLPSADEIYDCKVEHWGLDQPLLKHWEPEIPAPMSELTET DQA1*01:01 Extracellular Domain (SEQ ID NO: 7)
GAGGACATCGTGGCCGATCACGTGGCAAGCTGCGGCGTGAACCTGTACCAGTTCTACGGCCCCTCTGGCCAGTA
CACCCATGAATTTGATGGAGATGAGGAGTTCTACGTGGACCTGGAGAGGAAGGAGACTGCCTGGCGGTGGCCTG
AGTTCAGCAAATTTGGAGGTTTTGACCCGCAGGGTGCACTGAGAAACATGGCTGTGGCAAAACACAACTTGAAC
ATCATGATTAAACGCTACAACTCTACCGCTGCTACCAATGAGGTTCCTGAGGTCACAGTGTTTTCCAAGTCTCC
CGTGACACTGGGTCAGCCOAACACCCTCATTTGTCTTGTGGACAACATCTTTCCTCCTGTGGTCAACATCACAT
GGCTGAGCAATGGGCAGTCAGTCACAGAAGGTGTTTCTGAGACCAGCTTCCTCTCCAAGAGTGATCATTCCTTC
TTCAAGATCAGTTACCTCACCTTCCTCCCTTCTGCTGATGAGATTTATGACTGCAAGGTGGAGCACTGGGGCCT
GGACCAGCCTCTTCTGAAACACTGGGAGCCTGAGATTCCAGCCCCTATGTCAGAGCTCACAGAGACT Signal Peptide; DQA1*01:01 Extracellular Domain; Gly/Ser Linker, Zip
Sequences and His tag sequences) (SEQ ID NO: 8)
MMRPIVLVLLFATSALA*EDIVADHVASCGVNLYQFYGPSGQYTHEFDGDEEFYVDLERKETAWRWPEFSKFGGF
DPQGALRNMAVAKHNLNIMIERYNSTAATNEVBEVTVESKSPVTLGQPNTLICLVDNIFPPVVNITWLSNGQSV
TEGVSETSFLSKSDHSFFKISYLTFLPSADEIYDCKVEHWGLDQPLLEHWEPEIPAPMSELTET*GGGGSLEIRA
AFLRQRNTALRTEVAELEQEVQRLENEVSQYETRYGPLGGGKGSHHHHHH Signal Peptide (Fibroin light chain-derived)
MMRPIVLVLLFATSALA (SEQ ID NO: 9)

When the MHRC class II molecule is complexed with an antigen peptide, the 10-30 amino acid long antigen peptide binds the peptide-binding groove and is presented extracellularly to CD4+ cells. Both the alpha- and beta-chains fold into two separate domains; alpha-1 and alpha-2 for the alpha polypeptide, and beta-1 and beta-2 for the beta polypeptide. The invariant residues at L114, V116, V143, L158, and M160 that are recognized and bound by CD4 are located in the beta-2 domain of the beta polypeptide. The open-ended peptide-binding groove which holds the presented antigen is found between the alpha-1 and beta-1 domains. Upon interaction with a CD4+ T cell, the MHC class II complex interacts with a T cell receptor (TCR) expressed on the surface of the T cell. In addition, the beta chain of the MHC class 11 molecule weakly interacts ($K_D$>2 mM) with CD4 expressed on the surface of the T cell. The canonical CD4 amino acid sequence (UniProt—P01730) is provided in Table 2 (SEQ ID NO: 10).

TABLE 2

Human CD4 Amino Acid Sequence

MNRGVPFRHLLLVLQLALLPAATQGKKVVLGKKGDTVELTCTASQKKSIQF
HWKNSNQIKILGNQGSFLTKGPSKLNDRADSRRSLWDQGNFPLIIKNLKIE
DSDTYICEVEDQKEEVQLLVFGLTANSDTHLLQGQSLTLTLESPPGSSPSV
QCRSPRGKNIQGGKTLSVSQLELQDSGTWTCTVLQNQKKVEFKIDIVVLAF
QKASSIVYKKEGEQVEFSFPLAFTVEKLTGSGELWWQAERASSSKSWITFD
LKNKEVSVKRVTQDPKLQMGKKLPLHLTLPQALPQYAGSGNLTLALEAKTG
KLHQEVNLVVMRATQLQKNLTCEVWGPTSPKLMLSLKLENKEAKVSKREKA
VWVLNPEAGMWQCLLSDSGQVLLESNIKVLPTWSTPVQPMALIVLGGVAGL
LLFIGLGIFFCVRCRHRRRQAERMSQIKRLLSEKKTCQCPHRFQKTCSPI
(SEQ ID NO: 10)

The term "T cell receptor" (TCR), as used herein, refers to a heteromeric cell-surface receptor capable of specifically interacting with a target antigen. As used herein, "TCR" includes but is not limited to naturally occurring and non-naturally occurring TCRs, full-length TCRs and antigen binding portions thereof, chimeric TCRs, TCR fusion constructs, and synthetic TCRs. In human, TCRs are expressed on the surface of T cells, and they are responsible for T cell recognition and targeting of antigen presenting cells. Antigen presenting cells (APCs) display fragments of foreign proteins (antigens) complexed with the major histocompatibility complex (MHC class I or MHC class II; also referred to herein as complexed with an HLA molecule, e.g., an HLA class II molecule). A TCR recognizes and binds to the peptide:HLA complex and recruits CD8 (for MHC Class I molecules) or CD4 (for MHC class II molecules) expressed by T cells, activating the TCR. The activated TCR initiates downstream signaling and an immune response, including the destruction of the APC.

In general, a TCR can comprise two chains, an alpha chain and a beta chain (or less commonly a gamma chain and a delta chain), interconnected by disulfide bonds. Each chain comprises a variable domain (alpha chain variable domain and beta chain variable domain) and a constant region (alpha chain constant region and beta chain constant region). The variable domain is located distal to the cell membrane, and the variable domain interacts with an antigen. The constant region is located proximal to the cell membrane. A TCR can further comprise a transmembrane region and a short cytoplasmic tail. As used herein, the term "constant region" encompasses the transmembrane region and the cytoplasmic tail, when present, as well as the traditional "constant region."

The variable domains can be further subdivided into regions of hypervariability, termed complementarity determining regions (CDRs), interspersed with regions that are more conserved, termed framework regions (FR). Each alpha chain variable domain and beta chain variable domain comprises three CDRs and four FRs: FR1, CDR1, FR2, CDR2, FR3, CDR3, FR4. Each variable domain contains a binding domain that interacts with an antigen. Though all three CDRs on each chain are involved in antigen binding, CDR3 is believed to be the primary antigen binding region, while CDR1 and CDR2 are believed to primarily recognize the HLA molecule.

Where not expressly stated, and unless the context indicates otherwise, the term "TCR" also includes an antigen-binding fragment or an antigen-binding portion of any TCR disclosed herein, and includes a monovalent and a divalent fragment or portion, and a single chain TCR. The term "TCR" is not limited to naturally occurring TCRs bound to the surface of a T cell. As used herein, the term "TCR" further refers to a TCR described herein that is expressed on the surface of a cell other than a T cell (e.g., a cell that naturally expresses or that is modified to express CD4, as described herein), or a TCR described herein that is free from a cell membrane (e.g., an isolated TCR or a soluble TCR).

An "antigen binding molecule," "portion of a TCR," or "TCR fragment" refers to any portion of an TCR less than the whole. An antigen binding molecule can include the antigenic CDRs.

An "antigen" refers to any molecule, e.g., a peptide, that provokes an immune response or is capable of being bound by a TCR. An "epitope," as used herein, refers to a portion of a polypeptide that provokes an immune response or is capable of being bound by a TCR. The immune response may involve either antibody production, or the activation of specific immunologically-competent cells, or both. A person of skill in the art would readily understand that any macromolecule, including virtually all proteins or peptides, can serve as an antigen. An antigen and/or an epitope can be endogenously expressed, i.e. expressed by genomic DNA, or can be recombinantly expressed. An antigen and/or an epitope can be specific to a certain tissue, such as a diseased cell, e.g., a cancer cell, or it can be broadly expressed. In addition, fragments of larger molecules can act as antigens. In one aspect, antigens are tumor antigens. An epitope can be present in a longer polypeptide (e.g., in a protein), or an epitope can be present as a fragment of a longer polypeptide. In some aspects, an epitope is complexed with a major histocompatibility complex (MHC; also referred to herein as complexed with an HLA molecule, e.g., an HLA class 1 molecule).

The term "autologous" refers to any material derived from the same individual to which it is later to be re-introduced. For example, an autologous T cell therapy comprises administering to a subject a T cell that was isolated from the same subject. The term "allogeneic" refers to any material derived from one individual which is then introduced to another individual of the same species. For example, an allogeneic T cell transplantation comprises administering to a subject a T cell that was obtained from a donor other than the subject.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. Examples of cancers that can be treated by the methods of the present invention include, but are not limited to, cancers of the immune system including lymphoma, leukemia, and other leukocyte malignancies. In some aspects, the methods of the present invention can be used to reduce the tumor size of a tumor derived from, for example, melanoma, bone cancer, pancreatic cancer, skin cancer, cancer of the head or neck, uterine cancer, ovarian cancer, rectal cancer, stomach cancer, uterine cancer, lung cancer, Hodgkin's Disease, non-Hodgkin's lymphoma (NHL), cancer of the esophagus, cancer of the small intestine, cancer of the urethra, chronic or acute leukemia, acute myeloid leukemia, chronic myeloid leukemia, acute lymphoblastic leukemia (ALL) (including non T cell ALL), chronic lymphocytic leukemia (CLL), cancer of the bladder, cancer of the kidney or ureter, carcinoma of the renal pelvis, glioma, squamous cell cancer, and combinations of said cancers. The particular cancer can be responsive to chemo- or radiation therapy or the cancer can be refractory. A refractory cancer refers to a cancer that is not amendable to surgical intervention, and the cancer is either initially unresponsive to chemo- or radiation therapy or the cancer becomes unresponsive over time.

The term "progression-free survival," which can be abbreviated as PFS, as used herein refers to the time from the treatment date to the date of disease progression per the revised IWG Response Criteria for Malignant Lymphoma or death from any cause.

The term "overall survival," which can be abbreviated as OS, is defined as the time from the date of treatment to the date of death.

The term "infection," as used herein refers to any type of invasion of one or more tissue of the body by a foreign agent. The term "infection" includes without limitation infection by a virus (including viroids and prions), a bacterium, a fungus, a parasite, and any combination thereof.

The term "lymphocyte" as used herein includes natural killer (NK) cells, T cells, or B cells. NK cells are a type of cytotoxic (cell toxic) lymphocyte that represents a major component of the inherent immune system. NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). T-cell receptors (TCR) differentiate T cells from other lymphocyte types. The thymus, a specialized organ of the immune system, is primarily responsible for the T cell's maturation. There are six types of T-cells, namely: Helper T-cells (e.g., CD4+ cells), Cytotoxic T-cells (also known as TC, cytotoxic T lymphocyte, CTL, T-killer cell, cytolytic T cell, CD8+ T-cells or killer T cell), Memory T-cells ((i) stem memory $TSC_M$ cells, like naive cells, are CD45RO−, CCR7+, CD45RA+, CD62L+(L-selectin), CD27+, CD28+ and IL-7Ra+, but they also express large amounts of CD95, IL-2Rβ, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory $T_{EM}$ cells, however, do not express L-selectin or CCR7 but produce effector cytokines like IFNγ and IL-4), Regulatory T-cells (Tregs, suppressor T cells, or CD4+CD25+ regulatory T cells), Natural Killer T-cells (NKT) and Gamma Delta T-cells. B-cells, on the other hand, play a principal role in humoral immunity (with antibody involvement). A B cell makes antibodies and antigens and performs the role of antigen-presenting cells (APCs) and turns into memory B-cells after activation by antigen interaction. In mammals, immature B-cells are formed in the bone marrow, where its name is derived from.

The terms "modified" and "mutated," when used herein to refer to a nucleotide or amino acid sequence, refers to a change in the sequence relative to a wild-type sequence or a specified reference sequence. The terms "modified" and "mutated" do not require a step in a process for making the modified or mutated sequence (e.g., the modified beta chain sequence), unless otherwise specified. Rather, these terms indicate that there is a variation in the modified or mutated sequence relative to a reference sequence, e.g., a wild-type sequence. For example, a DQ beta chain comprising a substitution mutation at a position corresponding to amino acid residue 114 of SEQ ID NO: 1 does not require that a wild-type DQ beta chain has been physically altered to arrive at the recited DQ beta chain; but rather that, when properly aligned, the recited DQ beta chain comprises an amino acid residue at the recited position (residue 114) that is different from the amino acid residue at the corresponding position in a wild-type or reference DQ beta chain.

The term "any amino acid," as used herein, means any known amino acid. Amino acids are organic compounds comprising (i) an amine (—NH$_2$) functional group, (ii) a carboxyl (—COOH) functional group, and (iii) a side chain (R group), wherein the side chain is specific to each amino acid. This includes but is not limited to any naturally occurring amino acid, as well as any modifications and variants thereof. There are about 500 naturally occurring amino acids, 20 of which are encoded by the genetic code. Amino acids with positively charged side chains include arginine (Arg; R), histidine (His, H), and lysine (Lys; K). Amino acids with a negatively charged side chain include aspartic acid (Asp; D) and glutamic acid (Glu; E). Amino acids with a polar uncharged side chain include serine (Ser; S), threonine (Thr; T), glutamine (Gln; Q), and asparagine (Asn; N). Amino acids with a hydrophobic side chain include alanine (Ala; A), isoleucine (Ile; I), leucine (Leu; L), methionine (Met; M), phenylalanine (Phe; F), valine (Val; V), Tryptophan (Trp; W), Tyrosine (Tyr; Y). Tryptophan (Trp; W), tyrosine (Tyr; Y), and methionine (Met; M) can also be classified as polar and/or amphipathic, in that these amino acids can often be found at the surface of proteins or lipid membranes. Additional amino acids include cysteine (Cys; C), selenocysteine (Sec; U), glycine (Gly; G) and proline (Pro; P).

As used herein "at a position corresponding to" is used as a means to identify a particular amino acid residue, e.g., a specific amino acid position, in a polynucleotide or a particular nucleic acid, e.g., a specific nucleic acid position, in a polypeptide. The position can be determined by properly aligning the sequence in question with the referenced sequence. A person of skill in the art would readily understand how to align to sequences to determine the relative position. For example, various alignment tools are available online, including, without limitation, "Clustal Omega Multiple Sequence Alignment," available at www.ebi.ac.uk (last visited May 25, 2019).

The term "genetically engineered" or "engineered" refers to a method of modifying the genome of a cell, including, but not limited to, deleting a coding or non-coding region or a portion thereof or inserting a coding region or a portion thereof. In some aspects, the cell that is modified is a lymphocyte, e.g., a T cell or a modified cell that expresses CD4, which can either be obtained from a patient or a donor. The cell can be modified to express an exogenous construct, such as, e.g., a T cell receptor (TCR) disclosed herein, which is incorporated into the cell's genome. In some aspects, the cell is modified to express CD4.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT), and allogeneic T cell transplantation.

Cells used in an immunotherapy described herein can come from any source known in the art. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety. An immunotherapy can also comprise administering a modified cell to a subject, wherein the modified cell expresses CD4 and a TCR disclosed herein. In some aspects, the modified cell is not a T cell.

A "patient" as used herein includes any human who is afflicted with a cancer (e.g., a lymphoma or a leukemia). The terms "subject" and "patient" are used interchangeably herein.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD4 complex, that specifically binds with a cognate stimulatory ligand present on an antigen present cell. A "stimulatory ligand" is a ligand that when present on an antigen presenting cell (e.g., an aAPC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an MHC Class II molecule loaded with a peptide, an anti-CD4 antibody, an anti-CD28 antibody, an anti-CD2 antibody, and an anti-CD3 antibody.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one aspect, "treatment" or "treating" includes a partial remission. In another aspect, "treatment" or "treating" includes a complete remission.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% (i.e., ±10%). For example, about 3 mg can include any number between 2.7 mg and 3.3 mg (for 10%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one-tenth and one-hundredth of an integer), unless otherwise indicated.

Various aspects of the invention are described in further detail in the following subsections.

II. Compositions of the Disclosure

The present disclosure is directed to HLA class II molecules with enhanced CD4 binding. Certain aspects of the present disclosure are directed to HLA class II molecules comprising a beta chain, wherein the beta chain comprises one or more mutations. In certain aspects, the one or more mutations in the beta chain increase the affinity of the beta chain for CD4. In certain aspects, the beta chain is an HLA-DQ ("DQ") beta chain.

II.A. MHC Class II Molecules

The human leukocyte antigen (HLA) system (the major histocompatibility complex [MHC] in humans) is an important part of the immune system and is controlled by genes located on chromosome 6. It encodes cell surface molecules specialized to present antigenic peptides to the T-cell receptor (TCR) on T cells. (See also Overview of the Immune System.) MHC molecules that present antigen (Ag) are divided into 2 main classes: Class I MHC molecules and Class II MHC molecules.

Class II MHC molecules are present as transmembrane glycoproteins on the surface of professional antigen presenting cells (APCs). Intact class II molecules consist of an alpha chain and a beta chain. Three loci in the HLA complex encode MHC class II proteins: HLA-DP, HLA-DQ, and HLA-DR. T cells that express CD4 molecules react with class II MHC molecules. These lymphocytes often have effector and helper functions and activate a response to eliminate self-cells infected with intracellular pathogens or to destroy extracellular parasites and help other T cells such as CD8 T cells. Because only professional APCs express class II MHC molecules, only these cells present antigen for CD4 T cells (CD4 binds to the nonpolymorphic part of the alpha-2 and beta-2 domains of the alpha and beta chains of an MHC class II molecule respectively).

In some aspects, the HLA class II alpha and beta chains are selected from an HLA-DP, HLA-DQ, and HLA-DR allele. In certain aspects, the HLA class II beta chain is an HLA-DQ allele. In certain aspects, the HLA class II alpha chain is an HLA-DQ allele.

Many HLA-DQ alleles are known in the art, and any of the known alleles can be used in the present disclosure. Examples of HLA-DQ alpha chain and beta chain alleles are shown in Table 1. An updated list of HLA alleles is available at hla.alleles.org/(last visited on Jul. 10, 2019).

II.A.1. MHC Class II Beta Chain

In certain aspects, the HLA class II molecule comprises a DQ beta chain, wherein the DQ beta chain comprises an amino acid other than leucine at a position corresponding to amino acid residue 114 of SEQ ID NO: 1. Any amino acid other than leucine can be present at the position corresponding to amino acid residue 114 of SEQ ID NO: 1. In some aspects, the amino acid other than leucine is an amino acid comprising a hydrophobic side chain. In certain aspects, the amino acid other than leucine at the position corresponding to amino acid residue 114 of SEQ ID NO: 1 is an amino acid selected from an alanine, a valine, an isoleucine, a methionine, a phenylalanine, a tyrosine, and a tryptophan. In certain aspects, the amino acid other than leucine at the position corresponding to amino acid residue 114 of SEQ ID NO: 1 is an alanine. In certain aspects, the amino acid other than leucine at the position corresponding to amino acid residue 114 of SEQ ID NO: 1 is a valine. In certain aspects, the amino acid other than leucine at the position corresponding to amino acid residue 114 of SEQ ID NO: 1 is an isoleucine. In certain aspects, the amino acid other than leucine at the position corresponding to amino acid residue 114 of SEQ ID NO: 1 is a methionine. In certain aspects, the amino acid other than leucine at the position corresponding to amino acid residue 114 of SEQ ID NO: 1 is a phenylalanine. In certain aspects, the amino acid other than leucine at the position corresponding to amino acid residue 114 of SEQ ID NO: 1 is a tyrosine. In certain aspects, the amino acid other than leucine at the position corresponding to amino acid residue 114 of SEQ ID NO: 1 is a tryptophan.

In some embodiments, the amino acid other than leucine at the position corresponding to amino acid residue 114 of SEQ ID NO: 1 consists of more than one amino acid, e.g., two amino acids, three amino acids, four amino acids, five amino acids, or more. In some aspects at least one of the more than one amino acids comprises a hydrophobic side chain. In certain aspects, the amino acid other than leucine at the position corresponding to amino acid residue 114 of SEQ ID NO: 1 consists of a series, e.g., at least 2, at least 3, at least 4, or at least 5, amino acids, wherein each of the series of amino acids comprises a hydrophobic side chain.

In certain aspects, the HLA class II molecule comprises a DQ beta chain, wherein the DQ beta chain comprises an amino acid other than valine at a position corresponding to amino acid residue 143 of SEQ ID NO: 1. Any amino acid other than valine can be present at the position corresponding to amino acid residue 143 of SEQ ID NO: 1. In some aspects, the amino acid other than valine is an amino acid comprising a hydrophobic side chain. In certain aspects, the amino acid other than valine at the position corresponding to amino acid residue 143 of SEQ ID NO: 1 is an amino acid selected from an alanine, an isoleucine, a leucine, a methionine, a phenylalanine, a tyrosine, and a tryptophan. In certain aspects, the amino acid other than valine at the position corresponding to amino acid residue 143 of SEQ ID NO: 1 is an alanine. In certain aspects, the amino acid other than valine at the position corresponding to amino acid residue 143 of SEQ ID NO: 1 is an isoleucine. In certain aspects, the amino acid other than valine at the position corresponding to amino acid residue 143 of SEQ ID NO: 1 is a leucine. In certain aspects, the amino acid other than valine at the position corresponding to amino acid residue 143 of SEQ ID NO: 1 is a methionine. In certain aspects, the amino acid other than valine at the position corresponding to amino acid residue 143 of SEQ ID NO: 1 is a phenylalanine. In certain aspects, the amino acid other than valine at the position corresponding to amino acid residue 143 of SEQ ID NO: 1 is a tyrosine. In certain aspects, the amino acid other than valine at the position corresponding to amino acid residue 143 of SEQ ID NO: 1 is a tryptophan.

In some aspects, the amino acid other than valine at the position corresponding to amino acid residue 143 of SEQ ID NO: 1 consists of more than one amino acid, e.g., two amino acids, three amino acids, four amino acids, five amino acids, or more. In some aspects at least one of the more than one amino acids comprises a hydrophobic side chain. In certain aspects, the amino acid other than valine at the position corresponding to amino acid residue 143 of SEQ ID NO: 1 consists of a series, e.g., at least 2, at least 3, at least 4, or at least 5, amino acids, wherein each of the series of amino acids comprises a hydrophobic side chain.

In certain aspects, the HLA class II molecule comprises a DQ beta chain, wherein the DQ beta chain comprises an amino acid other than asparagine at a position corresponding to amino acid residue 110 of SEQ ID NO: 1. Any amino acid other than asparagine can be present at the position corresponding to amino acid residue 110 of SEQ ID NO: 1. In some aspects, the amino acid other than asparagine is an amino acid comprising a polar uncharged side chain. In certain aspects, the amino acid other than asparagine at the position corresponding to amino acid residue 110 of SEQ ID NO: 1 is an amino acid selected from a serine, a threonine, and a glutamine. In certain aspects, the amino acid other than asparagine at the position corresponding to amino acid residue 110 of SEQ ID NO: 1 is a serine. In certain aspects, the amino acid other than asparagine at the position corresponding to amino acid residue 110 of SEQ ID NO: 1 is a threonine. In certain aspects, the amino acid other than asparagine at the position corresponding to amino acid residue 110 of SEQ ID NO: 1 is a glutamine.

In some aspects, the amino acid other than asparagine at the position corresponding to amino acid residue 110 of SEQ ID NO: 1 consists of more than one amino acid, e.g., two amino acids, three amino acids, four amino acids, five amino acids, or more. In some aspects at least one of the more than one amino acids comprises a polar uncharged side chain. In certain aspects, the amino acid other than asparagine at the position corresponding to amino acid residue 110 of SEQ ID NO: 1 consists of a series, e.g., at least 2, at least 3, at least 4, or at least 5, amino acids, wherein each of the series of amino acids comprises a polar uncharged side chain.

In certain aspects, the HLA class II molecule comprises a DQ beta chain, wherein the DQ beta chain comprises an amino acid other than isoleucine at a position corresponding to amino acid residue 116 of SEQ ID NO: 1. Any amino acid other than isoleucine can be present at the position corresponding to amino acid residue 116 of SEQ ID NO: 1. In some aspects, the amino acid other than isoleucine is an amino acid comprising a hydrophobic side chain. In certain aspects, the amino acid other than isoleucine at the position corresponding to amino acid residue 116 of SEQ ID NO: 1 is an amino acid selected from an alanine, a valine, a leucine, a methionine, a phenylalanine, a tyrosine, and a tryptophan. In certain aspects, the amino acid other than isoleucine at the position corresponding to amino acid residue 116 of SEQ ID NO: 1 is an alanine. In certain aspects, the amino acid other than isoleucine at the position corresponding to amino acid residue 116 of SEQ ID NO: 1 is a valine. In certain aspects, the amino acid other than isoleucine at the position corresponding to amino acid residue 116 of SEQ ID NO: 1 is a leucine. In certain aspects, the amino acid other than isoleucine at the position corresponding to amino acid residue 116 of SEQ ID NO: 1 is a methionine. In certain aspects, the amino acid other than isoleucine at the position corresponding to amino acid residue 116 of SEQ ID NO: 1 is a phenylalanine. In certain aspects, the amino acid other than isoleucine at the position corresponding to amino acid residue 116 of SEQ ID NO: 1 is a tyrosine. In certain aspects, the amino acid other than isoleucine at the position corresponding to amino acid residue 116 of SEQ ID NO: 1 is a tryptophan.

In some aspects, the amino acid other than isoleucine at the position corresponding to amino acid residue 116 of SEQ ID NO: 1 consists of more than one amino acid, e.g., two amino acids, three amino acids, four amino acids, five amino acids, or more. In some aspects at least one of the more than one amino acids comprises a hydrophobic side chain. In certain aspects, the amino acid other than isoleucine at the position corresponding to amino acid residue 116 of SEQ ID NO: 1 consists of a series, e.g., at least 2, at least 3, at least 4, or at least 5, amino acids, wherein each of the series of amino acids comprises a hydrophobic side chain.

In certain aspects, the HLA class II molecule comprises a DQ beta chain, wherein the DQ beta chain comprises an amino acid other than serine at a position corresponding to amino acid residue 118 of SEQ ID NO: 1. Any amino acid other than serine can be present at the position corresponding to amino acid residue 118 of SEQ ID NO: 1. In some aspects, the amino acid other than serine is an amino acid comprising an electrically charged side chain. In certain aspects, the amino acid other than serine at the position corresponding to amino acid residue 118 of SEQ ID NO: 1 is an amino acid selected from an arginine, a histidine, and a lysine. In certain aspects, the amino acid other than serine at the position corresponding to amino acid residue 118 of SEQ ID NO: 1 is an arginine. In certain aspects, the amino acid other than serine at the position corresponding to amino acid residue 118 of SEQ ID NO: 1 is a histidine. In certain aspects, the amino acid other than serine at the position corresponding to amino acid residue 118 of SEQ ID NO: 1 is a lysine.

In some aspects, the amino acid other than serine at the position corresponding to amino acid residue 118 of SEQ ID NO: 1 consists of more than one amino acid, e.g., two amino acids, three amino acids, four amino acids, five amino acids, or more. In some aspects at least one of the more than one amino acids comprises an electrically charged side chain. In certain aspects, the amino acid other than serine at the position corresponding to amino acid residue 118 of SEQ ID NO: 1 consists of a series, e.g., at least 2, at least 3, at least 4, or at least 5, amino acids, wherein each of the series of amino acids comprises an electrically charged side chain.

In certain aspects, the HLA class II molecule comprises a DQ beta chain, wherein the DQ beta chain comprises an amino acid other than proline at a position corresponding to amino acid residue 146 of SEQ ID NO: 1. Any amino acid other than proline can be present at the position corresponding to amino acid residue 146 of SEQ ID NO: 1. In some aspects, the amino acid other than proline is an amino acid comprising a polar uncharged side chain. In certain aspects, the amino acid other than proline at the position corresponding to amino acid residue 146 of SEQ ID NO: 1 is an amino acid selected from a serine, a threonine, an asparagine, and a glutamine. In certain aspects, the amino acid other than proline at the position corresponding to amino acid residue 146 of SEQ ID NO: 1 is a serine. In certain aspects, the amino acid other than proline at the position corresponding to amino acid residue 146 of SEQ ID NO: 1 is a threonine. In certain aspects, the amino acid other than proline at the position corresponding to amino acid residue 146 of SEQ ID NO: 1 is an asparagine. In certain aspects, the amino acid other than proline at the position corresponding to amino acid residue 146 of SEQ ID NO: 1 is a glutamine.

In some aspects, the amino acid other than proline at the position corresponding to amino acid residue 146 of SEQ ID NO: 1 consists of more than one amino acid, e.g., two amino acids, three amino acids, four amino acids, five amino acids, or more. In some aspects at least one of the more than one amino acids comprises a polar uncharged side chain. In certain aspects, the amino acid other than proline at the position corresponding to amino acid residue 146 of SEQ ID NO: 1 consists of a series, e.g., at least 2, at least 3, at least 4, or at least 5, amino acids, wherein each of the series of amino acids comprises a polar uncharged side chain.

In certain aspects of the present disclosure, the MHC class II molecule comprises a DQ beta chain comprising more than one substitution mutation relative to the wild-type DQ beta chain. In certain aspects, the DQ beta chain comprises at least two mutations, at least three mutations, at least four mutations, at least five mutations, at least six mutations, at least seven mutations, at least eight mutations, at least nine mutations, or at least ten mutations relative to the wild-type DQ beta chain.

In certain aspects, the DQ beta chain comprises an amino acid other than leucine at a position corresponding to amino acid residue 114 of SEQ ID NO: 1 and an amino acid other than valine at a position corresponding to amino acid residue 143 of SEQ ID NO: 1. In certain aspects, the DQ beta chain comprises an amino acid other than leucine at a position corresponding to amino acid residue 114 of SEQ ID NO: 1; an amino acid other than valine at a position corresponding to amino acid residue 143 of SEQ ID NO: 1; and at least three of: (i) an amino acid other than asparagine at a position corresponding to amino acid residue 110 of SEQ ID NO: 1, (ii) an amino acid other than isoleucine at a position corresponding to amino acid residue 116 of SEQ ID NO: 1, (iii) an amino acid other than serine at a position corresponding to amino acid residue 118 of SEQ ID NO: 1, and (iv) an amino acid other than proline at a position corresponding to amino acid residue 146 of SEQ ID NO: 1.

In some aspects, the DQ beta chain comprises (i) an amino acid other than leucine at a position corresponding to amino acid residue 114 of SEQ ID NO: 1; (ii) an amino acid other than valine at a position corresponding to amino acid residue 143 of SEQ ID NO: 1; (iii) an amino acid other than asparagine at a position corresponding to amino acid residue 110 of SEQ ID NO: 1; (iv) an amino acid other than isoleucine at a position corresponding to amino acid residue 116 of SEQ ID NO: 1; (v) an amino acid other than serine at a position corresponding to amino acid residue 118 of SEQ ID NO: 1; and (vi) an amino acid other than proline at a position corresponding to amino acid residue 146 of SEQ ID NO: 1.

In some aspects, (i) the amino acid other than leucine at the position corresponding to amino acid residue 114 of SEQ ID NO: 1, (ii) the amino acid other than valine at a position corresponding to amino acid residue 143 of SEQ ID NO: 1, or each of the amino acid other than leucine at the position corresponding to amino acid residue 114 of SEQ ID NO: 1 and the amino acid other than valine at a position corresponding to amino acid residue 143 of SEQ ID NO: 1 is an amino acid comprising a hydrophobic side chain.

In some aspects, (i) the amino acid other than leucine at the position corresponding to amino acid residue 114 of SEQ ID NO: 1 is selected from an alanine, a valine, an isoleucine, a methionine, a phenylalanine, a tyrosine, and a tryptophan; (ii) the amino acid other than valine at a position corresponding to amino acid residue 143 of SEQ ID NO: 1 is selected from an alanine, an isoleucine, a leucine, a methionine, a phenylalanine, a tyrosine, and a tryptophan; (iii) the amino acid other than asparagine at a position corresponding to amino acid residue 110 of SEQ ID NO: 1 is selected from a serine, a threonine, and a glutamine; (iv) the amino acid other than isoleucine at a position corresponding to amino acid residue 116 of SEQ ID NO: 1 is selected from an alanine, a valine, a leucine, a methionine, a phenylalanine, a tyrosine, and a tryptophan; (v) the amino acid other than serine at a position corresponding to amino acid residue 118 of SEQ ID NO: 1 is selected from an arginine, a histidine, and a lysine; and (vi) the amino acid other than proline at a position corresponding to amino acid residue 146 of SEQ ID NO: 1 is selected from a serine, a threonine, an asparagine, and a glutamine.

In some aspects, (i) the amino acid other than leucine at the position corresponding to amino acid residue 114 of SEQ ID NO: 1 is a tryptophan; (ii) the amino acid other than valine at a position corresponding to amino acid residue 143 of SEQ ID NO: 1 is selected from an alanine, an isoleucine, a leucine, a methionine, a phenylalanine, a tyrosine, and a tryptophan. In some aspects, (i) the amino acid other than leucine at the position corresponding to amino acid residue 114 of SEQ ID NO: 1 is selected from an alanine, a valine, an isoleucine, a methionine, a phenylalanine, a tyrosine, and a tryptophan; and (ii) the amino acid other than valine at a position corresponding to amino acid residue 143 of SEQ ID NO: 1 is a methionine. In some aspects, (i) the amino acid other than leucine at the position corresponding to amino acid residue 114 of SEQ ID NO: 1 is a tryptophan; and (ii) the amino acid other than valine at a position corresponding to amino acid residue 143 of SEQ ID NO: 1 is a methionine. In some aspects, (i) the amino acid other than leucine at the position corresponding to amino acid residue 114 of SEQ ID NO: 1 is a tryptophan; (ii) the amino acid other than valine at a position corresponding to amino acid residue 143 of SEQ ID NO: 1 is a methionine; (iii) the amino acid other than asparagine at a position corresponding to amino acid residue 110 of SEQ ID NO: 1 is a glutamine; (iv) the amino acid other than isoleucine at a position corresponding to amino acid residue 116 of SEQ ID NO: 1 is a valine; (v) the amino acid other than serine at a position corresponding to amino acid residue 118 of SEQ ID NO: 1 is a histidine; and (vi) the amino acid other than proline at a position corresponding to amino acid residue 146 of SEQ ID NO: 1 is a glutamine.

In certain aspects, a DQ beta chain described herein has an increased affinity for a CD4 protein as compared to a reference HLA class II molecule. In some aspects, the reference HLA class II molecule is an HLA class II molecule having a wild-type DQ beta chain. In some aspects, the reference HLA class II molecule is an HLA class II molecule having a DQ beta chain comprising (i) a leucine at a position corresponding to amino acid residue 114 of SEQ ID NO: 1 and/or (ii) a valine at a position corresponding to amino acid residue 143 of SEQ ID NO: 1. In some aspects, the reference HLA class II molecule is an HLA class II molecule having a DQ beta chain comprising (i) a leucine at a position corresponding to amino acid residue 114 of SEQ ID NO: 1, (ii) a valine at a position corresponding to amino acid residue 143 of SEQ ID NO: 1, (iii) an asparagine at a position corresponding to amino acid residue 110 of SEQ ID NO: 1, (iv) an isoleucine at a position corresponding to amino acid residue 116 of SEQ ID NO: 1, (iii) a serine at a position corresponding to amino acid residue 118 of SEQ ID NO: 1, and/or (iv) a proline at a position corresponding to amino acid residue 146 of SEQ ID NO: 1.

In some aspects, the increased affinity for CD4 is at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 1000-fold, at least about 1500-fold, at least about 2000-fold, at least about 2500-fold, at least about 3000-fold, at least about 3500-fold, at least about 4000-fold, at least about 4500-fold, or at least about 4000-fold greater than the affinity of the reference HLA class II molecule for CD4.

In some aspects, the increased affinity for CD4 is at least about 1.5-fold to at least about 5000-fold, 1.5-fold to at least about 4000-fold, 1.5-fold to at least about 3000-fold, 1.5-fold to at least about 2000-fold, 1.5-fold to at least about 1000-fold, 10-fold to at least about 5000-fold, 10-fold to at least about 4000-fold, 10-fold to at least about 3000-fold, 10-fold to at least about 2000-fold, 10-fold to at least about 1000-fold, 10-fold to at least about 900-fold, 10-fold to at least about 800-fold, 10-fold to at least about 700-fold, 10-fold to at least about 600-fold, 10-fold to at least about 500-fold, 10-fold to at least about 400-fold, 10-fold to at least about 300-fold, 10-fold to at least about 200-fold, 10-fold to at least about 100-fold, 100-fold to at least about 5000-fold, 100-fold to at least about 4000-fold, 100-fold to at least about 3000-fold, 100-fold to at least about 2000-fold, 100-fold to at least about 1000-fold, 100-fold to at least about 900-fold, 100-fold to at least about 800-fold, 100-fold to at least about 700-fold, 100-fold to at least about 600-fold, 100-fold to at least about 500-fold, 100-fold to at least about 400-fold, 100-fold to at least about 300-fold, or 100-fold to at least about 200-fold greater than the affinity of the reference HLA class II molecule for CD4.

In certain aspects, the DQ beta chain comprises an allele selected from an HLA-DQB1*02, an HLA-DQB1*03, an HLA-DQB1*04, an HLA-DQB1*05, and an HLA-DQB1*06 allele. In certain aspects, the DQ beta chain comprises an HLA-DQB1*05 allele. In particular aspects, the DQ beta chain comprises an HLA-DQB1*05:01 allele.

In certain aspects, the DQ beta chain comprises an allele selected from DQB1*02:01:01, DQB1*02:01:02, DQB1*02:01:03, DQB1*02:01:04, DQB1*02:01:05, DQB1*02:01:06, DQB1*02:01:07, DQB1*02:01:08, DQB1*02:01:09, DQB1*02:01:10, DQB1*02:01:11, DQB1*02:01:12, DQB1*02:01:13, DQB1*02:01:14, DQB1*02:01:15, DQB1*02:01:16, DQB1*02:01:17, DQB1*02:01:18, DQB1*02:01:19, DQB1*02:01:20, DQB1*02:01:21, DQB1*02:01:22, DQB1*02:01:23, DQB1*02:01:24, DQB1*02:01:25, DQB1*02:01:26, DQB1*02:01:27, DQB1*02:01:28, DQB1*02:01:29, DQB1*02:01:30, DQB1*02:01:31, DQB1*02:02:01:01, DQB1*02:02:01:02, DQB1*02:02:01:03, DQB1*02:02:01:04, DQB1*02:02:02, DQB1*02:02:03, DQB1*02:02:04, DQB1*02:02:05, DQB1*02:02:06, DQB1*02:02:07, DQB1*02:02:08, DQB1*02:02:09, DQB1*02:03:01, DQB1*02:03:02, DQB1*02:04, DQB1*02:05, DQB1*02:06, DQB1*02:07:01, DQB1*02:07:02, DQB1*02:08, DQB1*02:09, DQB1*02:10, DQB1*02:100, DQB1*02:101, DQB1*02:102, DQB1*02:103, DQB1*02:104, DQB1*02:105, DQB1*02:106, DQB1*02:107, DQB1*02:108, DQB1*02:109, DQB1*02:11, DQB1*02:110, DQB1*02:111, DQB1*02:112, DQB1*02:113, DQB1*02:114, DQB1*02:115, DQB1*02:116, DQB1*02:117, DQB1*02:118, DQB1*02:119, DQB1*02:12, DQB1*02:120, DQB1*02:121, DQB1*02:122, DQB1*02:123, DQB1*02:124, DQB1*02:125, DQB1*02:126, DQB1*02:127, DQB1*02:128, DQB1*02:129N, DQB1*02:13, DQB1*02:130, DQB1*02:131, DQB1*02:132N, DQB1*02:133, DQB1*02:134N, DQB1*02:135, DQB1*02:136, DQB1*02:137, DQB1*02:138, DQB1*02:139, DQB1*02:140, DQB1*02:141, DQB1*02:142, DQB1*02:14:01, DQB1*02:14:02, DQB1*02:15, DQB1*02:16, DQB1*02:17, DQB1*02:18N, DQB1*02:19, DQB1*02:20N, DQB1*02:21, DQB1*02:22, DQB1*02:23, DQB1*02:24, DQB1*02:25, DQB1*02:26, DQB1*02:27, DQB1*02:28, DQB1*02:29, DQB1*02:30, DQB1*02:31, DQB1*02:32, DQB1*02:33, DQB1*02:34, DQB1*02:35, DQB1*02:36, DQB1*02:37, DQB1*02:38, DQB1*02:39, DQB1*02:40, DQB1*02:41, DQB1*02:42, DQB1*02:43, DQB1*02:44, DQB1*02:45, DQB1*02:46, DQB1*02:47, DQB1*02:48, DQB1*02:49, DQB1*02:50, DQB1*02:51, DQB1*02:52, DQB1*02:53Q, DQB1*02:54, DQB1*02:55, DQB1*02:56, DQB1*02:57, DQB1*02:58N, DQB1*02:59, DQB1*02:60, DQB1*02:61, DQB1*02:62, DQB1*02:63, DQB1*02:64, DQB1*02:65, DQB1*02:66, DQB1*02:67NX, DQB1*02:68, DQB1*02:69, DQB1*02:70, DQB1*02:71, DQB1*02:72, DQB1*02:73, DQB1*02:74, DQB1*02:75, DQB1*02:76, DQB1*02:77, DQB1*02:78, DQB1*02:79, DQB1*02:80, DQB1*02:81, DQB1*02:82, DQB1*02:83, DQB1*02:84, DQB1*02:85, DQB1*02:86, DQB1*02:87, DQB1*02:88, DQB1*02:89:01, DQB1*02:89:02, DQB1*02:90, DQB1*02:91, DQB1*02:92, DQB1*02:93, DQB1*02:94, DQB1*02:95, DQB1*02:96N, DQB1*02:97, DQB1*02:98, DQB1*02:99, DQB1*03:01:01, DQB1*03:01:01:02, DQB1*03:01:01:03, DQB1*03:01:01:04, DQB1*03:01:01:05, DQB1*03:01:01:06, DQB1*03:01:01:07, DQB1*03:01:01:08, DQB1*03:01:01:

09, DQB1*03:01:01:10, DQB1*03:01:01:11, DQB1*03:01:01:12, DQB1*03:01:01:14, DQB1*03:01:01:15, DQB1*03:01:01:16, DQB1*03:01:01:17, DQB1*03:01:01:18, DQB1*03:01:01:19, DQB1*03:01:01:20, DQB1*03:01:02, DQB1*03:01:03, DQB1*03:01:04, DQB1*03:01:05, DQB1*03:01:06, DQB1*03:01:07, DQB1*03:01:08, DQB1*03:01:09, DQB1*03:01:10, DQB1*03:01:11, DQB1*03:01:12, DQB1*03:01:13, DQB1*03:01:14, DQB1*03:01:15, DQB1*03:01:16, DQB1*03:01:17, DQB1*03:01:18, DQB1*03:01:19, DQB1*03:01:20, DQB1*03:01:21, DQB1*03:01:22, DQB1*03:01:23, DQB1*03:01:24, DQB1*03:01:25, DQB1*03:01:26, DQB1*03:01:27, DQB1*03:01:28, DQB1*03:01:29, DQB1*03:01:30, DQB1*03:01:31, DQB1*03:01:32, DQB1*03:01:33, DQB1*03:01:34, DQB1*03:01:35, DQB1*03:01:36, DQB1*03:01:37, DQB1*03:01:38, DQB1*03:01:39, DQB1*03:01:40, DQB1*03:01:41, DQB1*03:01:42, DQB1*03:01:43, DQB1*03:01:44, DQB1*03:01:45, DQB1*03:01:46, DQB1*03:02:01:01, DQB1*03:02:01:02, DQB1*03:02:01:03, DQB1*03:02:01:04, DQB1*03:02:01:05, DQB1*03:02:01:06, DQB1*03:02:01:07, DQB1*03:02:01:08, DQB1*03:02:02, DQB1*03:02:03, DQB1*03:02:04, DQB1*03:02:05, DQB1*03:02:06, DQB1*03:02:07, DQB1*03:02:08, DQB1*03:02:09, DQB1*03:02:10, DQB1*03:02:11, DQB1*03:02:12, DQB1*03:02:13, DQB1*03:02:14, DQB1*03:02:15, DQB1*03:02:16, DQB1*03:02:17, DQB1*03:02:18, DQB1*03:02:19, DQB1*03:02:20, DQB1*03:02:21, DQB1*03:02:22, DQB1*03:02:23, DQB1*03:02:24, DQB1*03:02:25, DQB1*03:02:26, DQB1*03:02:27, DQB1*03:02:28, DQB1*03:02:29, DQB1*03:02:30, DQB1*03:03:02:01, DQB1*03:03:02:02, DQB1*03:03:02:03, DQB1*03:03:02:04, DQB1*03:03:02:05, DQB1*03:03:03, DQB1*03:03:04, DQB1*03:03:05, DQB1*03:03:06, DQB1*03:03:07, DQB1*03:03:08, DQB1*03:03:09, DQB1*03:03:10, DQB1*03:03:11, DQB1*03:03:12, DQB1*03:03:13, DQB1*03:03:14, DQB1*03:03:15, DQB1*03:03:16, DQB1*03:03:17, DQB1*03:03:18, DQB1*03:03:19, DQB1*03:03:20, DQB1*03:03:21, DQB1*03:04:01, DQB1*03:04:02, DQB1*03:04:03, DQB1*03:04:04, DQB1*03:05:01, DQB1*03:05:02, DQB1*03:05:03, DQB1*03:05:04, DQB1*03:06, DQB1*03:07, DQB1*03:08, DQB1*03:09, DQB1*03:100, DQB1*03:101, DQB1*03:102, DQB1*03:103, DQB1*03:104, DQB1*03:105, DQB1*03:106, DQB1*03:107, DQB1*03:108, DQB1*03:109, DQB1*03:10:01, DQB1*03:10:02:01, DQB1*03:10:02:02, DQB1*03:11, DQB1*03:110, DQB1*03:111, DQB1*03:112, DQB1*03:113, DQB1*03:114, DQB1*03:115, DQB1*03:116, DQB1*03:117, DQB1*03:118N, DQB1*03:119, DQB1*03:12, DQB1*03:120, DQB1*03:121, DQB1*03:122, DQB1*03:123, DQB1*03:124, DQB1*03:125, DQB1*03:126, DQB1*03:127, DQB1*03:128, DQB1*03:129, DQB1*03:13, DQB1*03:130, DQB1*03:131, DQB1*03:132, DQB1*03:133, DQB1*03:134, DQB1*03:135, DQB1*03:136, DQB1*03:137, DQB1*03:138, DQB1*03:139, DQB1*03:140, DQB1*03:141, DQB1*03:142, DQB1*03:143, DQB1*03:144, DQB1*03:145, DQB1*03:146, DQB1*03:147, DQB1*03:148, DQB1*03:149, DQB1*03:14:01, DQB1*03:14:02, DQB1*03:15, DQB1*03:150, DQB1*03:151, DQB1*03:152, DQB1*03:153, DQB1*03:154, DQB1*03:155, DQB1*03:156, DQB1*03:157, DQB1*03:158, DQB1*03:159, DQB1*03:16, DQB1*03:160, DQB1*03:161, DQB1*03:162, DQB1*03:163, DQB1*03:164, DQB1*03:165, DQB1*03:166, DQB1*03:167, DQB1*03:168, DQB1*03:169, DQB1*03:170, DQB1*03:171, DQB1*03:172, DQB1*03:

173, DQB1*03:174, DQB1*03:175, DQB1*03:176, DQB1*03:177, DQB1*03:178, DQB1*03:179, DQB1*03:17:01, DQB1*03:17:02, DQB1*03:18, DQB1*03:180, DQB1*03:181, DQB1*03:182, DQB1*03:183, DQB1*03:184, DQB1*03:185, DQB1*03:186, DQB1*03:187, DQB1*03:188, DQB1*03:189, DQB1*03:190, DQB1*03:191, DQB1*03:192, DQB1*03:193, DQB1*03:194, DQB1*03:195, DQB1*03:196, DQB1*03:197Q, DQB1*03:198:01, DQB1*03:198:02, DQB1*03:199, DQB1*03:19:01, DQB1*03:19:02, DQB1*03:19:03, DQB1*03:19:04, DQB1*03:20, DQB1*03:200, DQB1*03:201, DQB1*03:202, DQB1*03:203, DQB1*03:204, DQB1*03:205, DQB1*03:206, DQB1*03:207, DQB1*03:208, DQB1*03:209, DQB1*03:21, DQB1*03:210, DQB1*03:211, DQB1*03:212, DQB1*03:213NX, DQB1*03:214, DQB1*03:215, DQB1*03:216, DQB1*03:217, DQB1*03:218, DQB1*03:219, DQB1*03:220, DQB1*03:221, DQB1*03:222, DQB1*03:223, DQB1*03:224, DQB1*03:225, DQB1*03:226, DQB1*03:227, DQB1*03:228, DQB1*03:229, DQB1*03:22:01, DQB1*03:22:02, DQB1*03:230, DQB1*03:231, DQB1*03:232, DQB1*03:233, DQB1*03:234, DQB1*03:235, DQB1*03:236, DQB1*03:237N, DQB1*03:238, DQB1*03:239, DQB1*03:23:01, DQB1*03:23:02, DQB1*03:23:03, DQB1*03:24, DQB1*03:240, DQB1*03:241, DQB1*03:242, DQB1*03:243, DQB1*03:244, DQB1*03:245, DQB1*03:246, DQB1*03:247, DQB1*03:248, DQB1*03:249, DQB1*03:250, DQB1*03:251, DQB1*03:252, DQB1*03:253, DQB1*03:254, DQB1*03:255, DQB1*03:256, DQB1*03:257, DQB1*03:258, DQB1*03:259, DQB1*03:25:01, DQB1*03:25:02, DQB1*03:26, DQB1*03:260, DQB1*03:261, DQB1*03:262, DQB1*03:263, DQB1*03:264, DQB1*03:265, DQB1*03:266, DQB1*03:267, DQB1*03:268, DQB1*03:269N, DQB1*03:27, DQB1*03:270, DQB1*03:271, DQB1*03:272, DQB1*03:273, DQB1*03:274, DQB1*03:275, DQB1*03:277, DQB1*03:278, DQB1*03:279, DQB1*03:28, DQB1*03:280, DQB1*03:281, DQB1*03:282N, DQB1*03:283, DQB1*03:284, DQB1*03:285, DQB1*03:286, DQB1*03:287, DQB1*03:288, DQB1*03:289, DQB1*03:29, DQB1*03:290, DQB1*03:291, DQB1*03:292, DQB1*03:293, DQB1*03:294, DQB1*03:295, DQB1*03:296, DQB1*03:297, DQB1*03:298, DQB1*03:299, DQB1*03:30, DQB1*03:300, DQB1*03:301, DQB1*03:302, DQB1*03:303N, DQB1*03:304, DQB1*03:305, DQB1*03:306, DQB1*03:307, DQB1*03:308, DQB1*03:309, DQB1*03:31, DQB1*03:310N, DQB1*03:311, DQB1*03:312, DQB1*03:313, DQB1*03:314, DQB1*03:315, DQB1*03:316, DQB1*03:317:01, DQB1*03:317:02, DQB1*03:318, DQB1*03:319, DQB1*03:32, DQB1*03:320, DQB1*03:321, DQB1*03:322, DQB1*03:323, DQB1*03:324, DQB1*03:326, DQB1*03:327, DQB1*03:328, DQB1*03:329, DQB1*03:33, DQB1*03:330, DQB1*03:331, DQB1*03:332, DQB1*03:333, DQB1*03:334N4 bp, DQB1*03:335, DQB1*03:336, DQB1*03:337, DQB1*03:338N, DQB1*03:339N, DQB1*03:34, DQB1*03:340N, DQB1*03:341, DQB1*03:342, DQB1*03:343, DQB1*03:344, DQB1*03:345, DQB1*03:346, DQB1*03:347, DQB1*03:348, DQB1*03:349, DQB1*03:35, DQB1*03:350, DQB1*03:351, DQB1*03:352, DQB1*03:353, DQB1*03:354N, DQB1*03:355, DQB1*03:356NX, DQB1*03:357N, DQB1*03:358N, DQB1*03:36, DQB1*03:37, DQB1*03:38:01, DQB1*03:38:02, DQB1*03:39, DQB1*03:40, DQB1*03:41, DQB1*03:42, DQB1*03:43, DQB1*03:44, DQB1*03:45, DQB1*03:46, DQB1*03:47, DQB1*03:48, DQB1*03:49, DQB1*03:50,

DQB1*03:51, DQB1*03:52, DQB1*03:53, DQB1*03:54, DQB1*03:55, DQB1*03:56, DQB1*03:57, DQB1*03:58, DQB1*03:59, DQB1*03:60, DQB1*03:61, DQB1*03:62, DQB1*03:63, DQB1*03:64, DQB1*03:65, DQB1*03:66N, DQB1*03:67, DQB1*03:68, DQB1*03:69, DQB1*03:70, DQB1*03:71, DQB1*03:72, DQB1*03:73, DQB1*03:74, DQB1*03:75, DQB1*03:76, DQB1*03:77, DQB1*03:78, DQB1*03:79, DQB1*03:80, DQB1*03:81, DQB1*03:82, DQB1*03:83, DQB1*03:84N, DQB1*03:85, DQB1*03:86, DQB1*03:87, DQB1*03:88, DQB1*03:89, DQB1*03:90N, DQB1*03:91Q, DQB1*03:92, DQB1*03:93, DQB1*03:94, DQB1*03:95N, DQB1*03:96, DQB1*03:97, DQB1*03:98, DQB1*03:99Q, DQB1*04:01:01:01, DQB1*04:01:01:02, DQB1*04:01:02, DQB1*04:01:03, DQB1*04:01:04, DQB1*04:01:05, DQB1*04:02:01:01, DQB1*04:02:01:04, DQB1*04:02:01:05, DQB1*04:02:01:06, DQB1*04:02:01: 07, DQB1*04:02:01:08, DQB1*04:02:01:09, DQB1*04:02: 01:10, DQB1*04:02:02, DQB1*04:02:03, DQB1*04:02:04, DQB1*04:02:05, DQB1*04:02:06, DQB1*04:02:07, DQB1*04:02:08, DQB1*04:02:09, DQB1*04:02:10, DQB1*04:02:11, DQB1*04:02:12, DQB1*04:02:13, DQB1*04:02:14, DQB1*04:02:15, DQB1*04:02:16, DQB1*04:02:17, DQB1*04:02:18, DQB1*04:03:01, DQB1*04:03:02, DQB1*04:03:03, DQB1*04:04, DQB1*04:05, DQB1*04:06, DQB1*04:07, DQB1*04:08, DQB1*04:09, DQB1*04:10, DQB1*04:11, DQB1*04:12, DQB1*04:13, DQB1*04:14, DQB1*04:15, DQB1*04:16, DQB1*04:17, DQB1*04:18, DQB1*04:19, DQB1*04:20, DQB1*04:21, DQB1*04:22, DQB1*04:23, DQB1*04:24, DQB1*04:25N, DQB1*04:26, DQB1*04:27, DQB1*04:28, DQB1*04:29, DQB1*04:30, DQB1*04:31, DQB1*04:32, DQB1*04:33, DQB1*04:34, DQB1*04:35, DQB1*04:36N, DQB1*04:37, DQB1*04:38, DQB1*04:39, DQB1*04:40, DQB1*04:41N, DQB1*04:42, DQB1*04:43, DQB1*04:44, DQB1*04:45, DQB1*04:46N, DQB1*04:47, DQB1*04:48, DQB1*04:49, DQB1*04:50, DQB1*04:51, DQB1*04:52, DQB1*04:53, DQB1*04:54, DQB1*04:55, DQB1*04:56, DQB1*04:57, DQB1*04:58, DQB1*04:59N, DQB1*04:60, DQB1*04:61, DQB1*04:62, DQB1*05:01:01:01, DQB1*05:01:01:02, DQB1*05:01:01:03, DQB1*05:01:01: 04, DQB1*05:01:01:05, DQB1*05:01:02, DQB1*05:01:03, DQB1*05:01:04, DQB1*05:01:05, DQB1*05:01:06, DQB1*05:01:07, DQB1*05:01:08, DQB1*05:01:09, DQB1*05:01:10, DQB1*05:01:11, DQB1*05:01:12, DQB1*05:01:13, DQB1*05:01:14, DQB1*05:01:15, DQB1*05:01:16, DQB1*05:01:17, DQB1*05:01:18, DQB1*05:01:19, DQB1*05:01:20, DQB1*05:01:21, DQB1*05:01:22, DQB1*05:01:23, DQB1*05:01:24:01, DQB1*05:01:24:02, DQB1*05:01:25, DQB1*05:01:26, DQB1*05:01:27, DQB1*05:01:28, DQB1*05:01:29, DQB1*05:01:30, DQB1*05:01:31, DQB1*05:01:32, DQB1*05:01:33, DQB1*05:01:34, DQB1*05:02:01:01, DQB1*05:02:01:02, DQB1*05:02:01:03, DQB1*05:02:01: 04, DQB1*05:02:01:05, DQB1*05:02:01:06, DQB1*05:02: 02, DQB1*05:02:03, DQB1*05:02:04, DQB1*05:02:05, DQB1*05:02:06, DQB1*05:02:07, DQB1*05:02:08, DQB1*05:02:09, DQB1*05:02:10, DQB1*05:02:11, DQB1*05:02:12, DQB1*05:02:13, DQB1*05:02:14, DQB1*05:02:15, DQB1*05:02:16, DQB1*05:02:17, DQB1*05:02:18, DQB1*05:02:19, DQB1*05:03:01:01, DQB1*05:03:01:02, DQB1*05:03:01:03, DQB1*05:03:02, DQB1*05:03:03, DQB1*05:03:04, DQB1*05:03:05, DQB1*05:03:06, DQB1*05:03:07, DQB1*05:03:08, DQB1*05:03:09, DQB1*05:03:10, DQB1*05:03:11, DQB1*05:03:12, DQB1*05:03:13, DQB1*05:03:14, DQB1*05:03:15, DQB1*05:03:16, DQB1*05:03:17, DQB1*05:03:18, DQB1*05:03:19, DQB1*05:03:20,

DQB1*05:04, DQB1*05:05:01, DQB1*05:05:02, DQB1*05:06:01, DQB1*05:06:02, DQB1*05:07, DQB1*05:08, DQB1*05:09, DQB1*05:10, DQB1*05:100, DQB1*05:101, DQB1*05:102, DQB1*05:103, DQB1*05: 104, DQB1*05:105, DQB1*05:106, DQB1*05:107, DQB1*05:108, DQB1*05:109, DQB1*05:110N, DQB1*05:111, DQB1*05:112, DQB1*05:113, DQB1*05: 114, DQB1*05:115, DQB1*05:116, DQB1*05:117, DQB1*05:118, DQB1*05:119, DQB1*05:11:01, DQB1*05:11:02, DQB1*05:12, DQB1*05:120, DQB1*05: 121, DQB1*05:122, DQB1*05:123, DQB1*05:124, DQB1*05:125, DQB1*05:126, DQB1*05:127, DQB1*05: 128N, DQB1*05:129, DQB1*05:13, DQB1*05:130, DQB1*05:131, DQB1*05:132Q, DQB1*05:133, DQB1*05:134, DQB1*05:135, DQB1*05:136, DQB1*05: 137, DQB1*05:138, DQB1*05:139, DQB1*05:14, DQB1*05:140, DQB1*05:141, DQB1*05:142, DQB1*05: 143, DQB1*05:144, DQB1*05:145, DQB1*05:146, DQB1*05:147, DQB1*05:148, DQB1*05:149, DQB1*05: 15, DQB1*05:150, DQB1*05:151, DQB1*05:152, DQB1*05:153, DQB1*05:154, DQB1*05:155, DQB1*05: 156, DQB1*05:157, DQB1*05:158, DQB1*05:159, DQB1*05:16, DQB1*05:160, DQB1*05:161, DQB1*05: 162, DQB1*05:163, DQB1*05:164, DQB1*05:165, DQB1*05:166, DQB1*05:167, DQB1*05:168, DQB1*05: 169, DQB1*05:17, DQB1*05:170, DQB1*05:171, DQB1*05:172, DQB1*05:173, DQB1*05:174, DQB1*05: 175, DQB1*05:176, DQB1*05:177, DQB1*05:178, DQB1*05:179, DQB1*05:18, DQB1*05:180, DQB1*05: 181, DQB1*05:182, DQB1*05:183, DQB1*05:184, DQB1*05:185N, DQB1*05:186, DQB1*05:187, DQB1*05:188, DQB1*05:189, DQB1*05:19, DQB1*05: 190, DQB1*05:191, DQB1*05:192, DQB1*05:193, DQB1*05:194, DQB1*05:195, DQB1*05:196, DQB1*05: 197, DQB1*05:198, DQB1*05:199, DQB1*05:20, DQB1*05:200, DQB1*05:201, DQB1*05:202, DQB1*05: 203, DQB1*05:204, DQB1*05:205, DQB1*05:206N, DQB1*05:207, DQB1*05:208N5 bp, DQB1*05:209, DQB1*05:21, DQB1*05:210, DQB1*05:211, DQB1*05: 212, DQB1*05:213, DQB1*05:214, DQB1*05:215N, DQB1*05:216, DQB1*05:217, DQB1*05:22, DQB1*05: 23, DQB1*05:24, DQB1*05:25, DQB1*05:26, DQB1*05: 27, DQB1*05:28, DQB1*05:29, DQB1*05:30, DQB1*05: 31, DQB1*05:32, DQB1*05:33, DQB1*05:34, DQB1*05: 35, DQB1*05:36, DQB1*05:37, DQB1*05:38, DQB1*05: 39, DQB1*05:40, DQB1*05:41N, DQB1*05:42, DQB1*05:43:01, DQB1*05:43:02, DQB1*05:44, DQB1*05:45, DQB1*05:46, DQB1*05:47, DQB1*05:48, DQB1*05:49, DQB1*05:50, DQB1*05:51, DQB1*05:52, DQB1*05:53, DQB1*05:54, DQB1*05:55, DQB1*05:56, DQB1*05:57, DQB1*05:58, DQB1*05:59, DQB1*05:60, DQB1*05:61, DQB1*05:62, DQB1*05:63, DQB1*05:64, DQB1*05:65, DQB1*05:66:01, DQB1*05:66:02, DQB1*05:67, DQB1*05:68, DQB1*05:69, DQB1*05:70, DQB1*05:71, DQB1*05:72, DQB1*05:73, DQB1*05:74, DQB1*05:75, DQB1*05:76, DQB1*05:77, DQB1*05:78, DQB1*05:79, DQB1*05:80, DQB1*05:81, DQB1*05:82, DQB1*05:83, DQB1*05:84, DQB1*05:85, DQB1*05:86, DQB1*05:87Q, DQB1*05:88, DQB1*05:89:01, DQB1*05: 89:02, DQB1*05:90N, DQB1*05:91, DQB1*05:92, DQB1*05:93, DQB1*05:94, DQB1*05:95, DQB1*05:96, DQB1*05:97, DQB1*05:98, DQB1*05:99, DQB1*06:01: 01:01, DQB1*06:01:01:02, DQB1*06:01:02, DQB1*06:01: 03, DQB1*06:01:04, DQB1*06:01:05, DQB1*06:01:06, DQB1*06:01:07, DQB1*06:01:08, DQB1*06:01:09, DQB1*06:01:10, DQB1*06:01:11, DQB1*06:01:12, DQB1*06:01:13, DQB1*06:01:14, DQB1*06:01:15,

DQB1*06:01:16, DQB1*06:01:17, DQB1*06:01:18, DQB1*06:01:19, DQB1*06:01:20, DQB1*06:01:21, DQB1*06:02:01:01, DQB1*06:02:01:02, DQB1*06:02:01: 03, DQB1*06:02:01:04, DQB1*06:02:02, DQB1*06:02:03, DQB1*06:02:04, DQB1*06:02:05, DQB1*06:02:06, DQB1*06:02:07, DQB1*06:02:08, DQB1*06:02:09, DQB1*06:02:10, DQB1*06:02:11, DQB1*06:02:12, DQB1*06:02:13, DQB1*06:02:14, DQB1*06:02:15, DQB1*06:02:16, DQB1*06:02:17, DQB1*06:02:18, DQB1*06:02:19, DQB1*06:02:20, DQB1*06:02:21, DQB1*06:02:22, DQB1*06:02:23, DQB1*06:02:24, DQB1*06:02:25, DQB1*06:02:26, DQB1*06:02:27, DQB1*06:02:28, DQB1*06:02:29, DQB1*06:02:30, DQB1*06:02:31, DQB1*06:02:32, DQB1*06:02:33, DQB1*06:02:34, DQB1*06:02:35, DQB1*06:02:36, DQB1*06:02:37, DQB1*06:02:38, DQB1*06:03:01:01, DQB1*06:03:01:02, DQB1*06:03:01:03, DQB1*06:03:02, DQB1*06:03:03, DQB1*06:03:04, DQB1*06:03:05, DQB1*06:03:06, DQB1*06:03:07, DQB1*06:03:08, DQB1*06:03:09, DQB1*06:03:10, DQB1*06:03:11, DQB1*06:03:12, DQB1*06:03:13, DQB1*06:03:14, DQB1*06:03:15, DQB1*06:03:16, DQB1*06:03:17, DQB1*06:03:18, DQB1*06:03:19, DQB1*06:03:20, DQB1*06:03:21, DQB1*06:03:22, DQB1*06:03:23, DQB1*06:03:24, DQB1*06:03:25, DQB1*06:03:26, DQB1*06:03:27, DQB1*06:03:28, DQB1*06:03:29, DQB1*06:03:30, DQB1*06:03:31, DQB1*06:03:32, DQB1*06:03:33, DQB1*06:03:34, DQB1*06:03:35, DQB1*06:04:01, DQB1*06:04:02, DQB1*06:04:03, DQB1*06:04:04, DQB1*06:04:05, DQB1*06:04:06, DQB1*06:04:07, DQB1*06:04:08, DQB1*06:04:09, DQB1*06:04:10, DQB1*06:04:11, DQB1*06:04:12, DQB1*06:05:01, DQB1*06:05:02, DQB1*06:06, DQB1*06:07:01, DQB1*06:07:02, DQB1*06:08:01, DQB1*06:08:02, DQB1*06:08:03, DQB1*06:09:01:01, DQB1*06:09:01:02, DQB1*06:09:02, DQB1*06:09:03, DQB1*06:09:04, DQB1*06:09:05, DQB1*06:09:06, DQB1*06:09:07, DQB1*06:09:08, DQB1*06:09:09, DQB1*06:09:10, DQB1*06:10, DQB1*06:100, DQB1*06: 101, DQB1*06:102N, DQB1*06:103, DQB1*06:104, DQB1*06:105, DQB1*06:106, DQB1*06:107, DQB1*06: 108, DQB1*06:109, DQB1*06:110, DQB1*06:111, DQB1*06:112N, DQB1*06:113, DQB1*06:114, DQB1*06:115, DQB1*06:116, DQB1*06:117, DQB1*06: 118:01, DQB1*06:118:02, DQB1*06:118:03, DQB1*06: 119, DQB1*06:11:01, DQB1*06:11:02, DQB1*06:11:03, DQB1*06:11:04, DQB1*06:12, DQB1*06:120, DQB1*06: 121, DQB1*06:122, DQB1*06:123, DQB1*06:124, DQB1*06:125, DQB1*06:126, DQB1*06:127, DQB1*06: 128, DQB1*06:129, DQB1*06:130, DQB1*06:131, DQB1*06:132, DQB1*06:133, DQB1*06:134, DQB1*06: 135, DQB1*06:136, DQB1*06:137, DQB1*06:138, DQB1*06:139, DQB1*06:13:01, DQB1*06:13:02, DQB1*06:13:03, DQB1*06:140, DQB1*06:141, DQB1*06:142, DQB1*06:143, DQB1*06:144N, DQB1*06:145, DQB1*06:146:01, DQB1*06:146:02, DQB1*06:147, DQB1*06:148, DQB1*06:149, DQB1*06: 14:01, DQB1*06:14:02, DQB1*06:14:03, DQB1*06:150, DQB1*06:151, DQB1*06:152, DQB1*06:153:01, DQB1*06:153:02, DQB1*06:154, DQB1*06:155, DQB1*06:156, DQB1*06:157, DQB1*06:158N, DQB1*06:159, DQB1*06:15:01, DQB1*06:15:02, DQB1*06:16, DQB1*06:160, DQB1*06:161, DQB1*06: 162, DQB1*06:163, DQB1*06:164, DQB1*06:165, DQB1*06:166, DQB1*06:167, DQB1*06:168, DQB1*06: 169, DQB1*06:17, DQB1*06:170, DQB1*06:171, DQB1*06:172, DQB1*06:173, DQB1*06:174, DQB1*06:

175, DQB1*06:176, DQB1*06:177, DQB1*06:178, DQB1*06:179N, DQB1*06:180, DQB1*06:181, DQB1*06:182, DQB1*06:183, DQB1*06:184, DQB1*06: 185, DQB1*06:186, DQB1*06:187, DQB1*06:188, DQB1*06:189, DQB1*06:18:01, DQB1*06:18:02, DQB1*06:190:01, DQB1*06:190:02, DQB1*06:191, DQB1*06:192, DQB1*06:193N, DQB1*06:194, DQB1*06:195, DQB1*06:196, DQB1*06:197, DQB1*06: 198, DQB1*06:199, DQB1*06:19:01, DQB1*06:19:02, DQB1*06:20, DQB1*06:200, DQB1*06:201, DQB1*06: 202, DQB1*06:203, DQB1*06:204, DQB1*06:205, DQB1*06:206:01, DQB1*06:206:02, DQB1*06:207, DQB1*06:208, DQB1*06:209, DQB1*06:21, DQB1*06: 210, DQB1*06:211, DQB1*06:212, DQB1*06:213, DQB1*06:214, DQB1*06:215, DQB1*06:216N, DQB1*06:217, DQB1*06:218, DQB1*06:219, DQB1*06: 221, DQB1*06:222, DQB1*06:223, DQB1*06:224, DQB1*06:225, DQB1*06:226, DQB1*06:227, DQB1*06: 228, DQB1*06:229, DQB1*06:22:01, DQB1*06:22:02, DQB1*06:22:03, DQB1*06:23, DQB1*06:230, DQB1*06: 231, DQB1*06:232, DQB1*06:233, DQB1*06:234, DQB1*06:235, DQB1*06:236, DQB1*06:237, DQB1*06: 238, DQB1*06:239, DQB1*06:24, DQB1*06:240, DQB1*06:241, DQB1*06:242, DQB1*06:243, DQB1*06: 244, DQB1*06:245, DQB1*06:246, DQB1*06:247, DQB1*06:248, DQB1*06:249, DQB1*06:25, DQB1*06: 250, DQB1*06:251, DQB1*06:252N, DQB1*06:253, DQB1*06:254, DQB1*06:255, DQB1*06:256, DQB1*06: 257, DQB1*06:258, DQB1*06:259, DQB1*06:260, DQB1*06:261, DQB1*06:262, DQB1*06:263, DQB1*06: 264, DQB1*06:265, DQB1*06:266, DQB1*06:267, DQB1*06:268, DQB1*06:269, DQB1*06:26N, DQB1*06: 270:01, DQB1*06:270:02, DQB1*06:271, DQB1*06:272, DQB1*06:273, DQB1*06:274, DQB1*06:275, DQB1*06: 276, DQB1*06:277, DQB1*06:278, DQB1*06:279, DQB1*06:27:01, DQB1*06:27:02, DQB1*06:28, DQB1*06:280, DQB1*06:281, DQB1*06:282, DQB1*06: 283, DQB1*06:284, DQB1*06:285, DQB1*06:286, DQB1*06:287, DQB1*06:288, DQB1*06:289, DQB1*06: 29, DQB1*06:290, DQB1*06:291, DQB1*06:292, DQB1*06:293, DQB1*06:294, DQB1*06:295, DQB1*06: 296, DQB1*06:297, DQB1*06:298, DQB1*06:299, DQB1*06:30, DQB1*06:300, DQB1*06:301, DQB1*06: 302, DQB1*06:303N, DQB1*06:304N, DQB1*06:305, DQB1*06:306N, DQB1*06:307, DQB1*06:308N, DQB1*06:309, DQB1*06:31, DQB1*06:310, DQB1*06: 311, DQB1*06:312, DQB1*06:313, DQB1*06:314, DQB1*06:315, DQB1*06:316, DQB1*06:317N, DQB1*06:318, DQB1*06:319, DQB1*06:320, DQB1*06: 321, DQB1*06:322, DQB1*06:323, DQB1*06:324, DQB1*06:325, DQB1*06:326, DQB1*06:32:01, DQB1*06:32:02, DQB1*06:33, DQB1*06:34, DQB1*06: 35, DQB1*06:36, DQB1*06:37, DQB1*06:38, DQB1*06: 39, DQB1*06:40, DQB1*06:41, DQB1*06:42, DQB1*06: 43, DQB1*06:44, DQB1*06:45, DQB1*06:46, DQB1*06: 47, DQB1*06:48:01, DQB1*06:48:02, DQB1*06:49, DQB1*06:50, DQB1*06:51:01, DQB1*06:51:02, DQB1*06:52, DQB1*06:53:01, DQB1*06:53:02, DQB1*06:54N, DQB1*06:55, DQB1*06:56, DQB1*06:57, DQB1*06:58, DQB1*06:59, DQB1*06:60, DQB1*06:61, DQB1*06:62, DQB1*06:63, DQB1*06:64, DQB1*06:65, DQB1*06:66, DQB1*06:67, DQB1*06:68, DQB1*06:69: 01, DQB1*06:69:02, DQB1*06:70, DQB1*06:71, DQB1*06:72, DQB1*06:73, DQB1*06:74, DQB1*06: 75NX, DQB1*06:76, DQB1*06:77N, DQB1*06:78, DQB1*06:79:01, DQB1*06:79:02, DQB1*06:80, DQB1*06:81, DQB1*06:82, DQB1*06:83, DQB1*06:84,

DQB1*06:85, DQB1*06:86, DQB1*06:87, DQB1*06:88, DQB1*06:89, DQB1*06:90, DQB1*06:91, DQB1*06:92: 01, DQB1*06:92:02, DQB1*06:93, DQB1*06:94, DQB1*06:95, DQB1*06:96:01, DQB1*06:96:02, DQB1*06:97, DQB1*06:98, DQB1*06:99:01, DQB1*06: 99:02, and any combination thereof.

In certain aspects, the MHC class II molecule comprises a DQ beta chain comprising an amino acid sequence having at least about 70%, at least about 75%, at least about 80%, at least about 85%, at least about 90%, at least about 95%, at least about 96%, at least about 97%, at least about 98%, at least about 99%, or about 100% sequence identity to SEQ ID NO: 3, wherein the DQ beta chain comprises a trypto-phan at a position corresponding to amino acid residue 114 of SEQ ID NO: 1, and wherein the DQ beta chain comprises a methionine at a position corresponding to amino acid residue 143 of SEQ ID NO: 1. In certain aspects, the MHC class II molecule comprises a DQ beta chain comprising an amino acid sequence having at least about 70%, at least about 75%, at least about 80%, at least about 85%, at least about 90%, at least about 95%, at least about 96%, at least about 97%, at least about 98%, at least about 99%, or about 100% sequence identity to SEQ ID NO: 3, wherein the DQ beta chain comprises (i) a tryptophan at a position corre-sponding to amino acid residue 114 of SEQ ID NO: 1, (ii) a methionine at a position corresponding to amino acid residue 143 of SEQ ID NO: 1, (iii) a glutamine at a position corresponding to amino acid residue 110 of SEQ ID NO: 1; (iv) a valine at a position corresponding to amino acid residue 116 of SEQ ID NO: 1; (v) a histidine at a position corresponding to amino acid residue 118 of SEQ ID NO: 1; and (vi) a glutamine at a position corresponding to amino acid residue 146 of SEQ ID NO: 1. In certain aspects, the MHC class II molecule comprises a DQ beta chain com-prising an amino acid sequence set forth in SEQ ID NO: 3.

II.A.2. MHC Class II Alpha Chain

In some aspects of the present disclosure, the MHC class II molecule further comprises an alpha chain. In some aspects, the alpha chain is a wild-type alpha chain. In some aspects, the alpha chain is a DQ alpha chain. Any DQ alpha chain can be used in the compositions and methods of the present disclosure. In some aspects, the DQ alpha chain comprises an HLA-DQA1*01, HLA-DQA1*02, HLA-DQA1*03, HLA-DQA1*04, HLA-DQA1*05, or HLA-DQA1*06 allele. In certain aspects, the DQ alpha chain comprises an HLA-DQA1*01 allele. In certain aspects, the DQ alpha chain comprises an HLA-DQA1*02 allele. In certain aspects, the DQ alpha chain comprises an HLA-DQA1*03 allele. In certain aspects, the DQ alpha chain comprises an HLA-DQA1*04 allele. In certain aspects, the DQ alpha chain comprises an HLA-DQA1*05 allele. In certain aspects, the DQ alpha chain comprises an HLA-DQA1*06 allele.

In certain aspects, the DQ alpha chain is selected from DQA1*01:01:01:01, DQA1*01:01:01:02, DQA1*01:01:01: 03, DQA1*01:01:01:05, DQA1*01:01:01:06, DQA1*01: 01:02, DQA1*01:01:03, DQA1*01:01:04, DQA1*01:01: 05, DQA1*01:02:01:01, DQA1*01:02:01:02, DQA1*01: 02:01:03, DQA1*01:02:01:04, DQA1*01:02:01:05, DQA1*01:02:01:06, DQA1*01:02:01:07, DQA1*01:02:01: 08, DQA1*01:02:01:09, DQA1*01:02:01:10, DQA1*01: 02:01:11, DQA1*01:02:01:12, DQA1*01:02:02:01, DQA1*01:02:02:02, DQA1*01:02:02:03, DQA1*01:02:02: 04, DQA1*01:02:03, DQA1*01:02:04, DQA1*01:03:01: 01, DQA1*01:03:01:02, DQA1*01:03:01:03, DQA1*01: 03:01:04, DQA1*01:03:01:05, DQA1*01:03:01:06, DQA1*01:03:01:07, DQA1*01:03:01:08, DQA1*01:03:01:

09, DQA1*01:04:01:01, DQA1*01:04:01:02, DQA1*01: 04:01:03, DQA1*01:04:01:04, DQA1*01:04:02, DQA1*01:05:01, DQA1*01:05:02, DQA1*01:06, DQA1*01:07Q, DQA1*01:08, DQA1*01:09, DQA1*01: 10, DQA1*01:11, DQA1*01:12, DQA1*01:13, DQA1*01: 14, DQA1*01:15N, DQA1*01:16N, DQA1*01:17, DQA1*01:18, DQA1*01:19, DQA1*01:20, DQA1*01:21, DQA1*01:22, DQA1*01:23, DQA1*01:24, DQA1*01:25, DQA1*01:26, DQA1*02:01:01:01, DQA1*02:01:01:02, DQA1*02:01:02, DQA1*02:02N, DQA1*02:03, DQA1*03:01:01, DQA1*03:01:03, DQA1*03:02:01:01, DQA1*03:02:01:02, DQA1*03:03:01:01, DQA1*03:03:01: 02, DQA1*03:03:01:03, DQA1*03:03:01:04, DQA1*03: 03:01:05, DQA1*03:03:01:06, DQA1*03:03:01:07, DQA1*03:03:02, DQA1*03:04, DQA1*03:05, DQA1*03: 06, DQA1*03:07, DQA1*04:01:01:01, DQA1*04:01:01: 02, DQA1*04:01:01:03, DQA1*04:01:01:04, DQA1*04: 01:01:05, DQA1*04:01:01:06, DQA1*04:01:01:07, DQA1*04:01:01:08, DQA1*04:01:02:01, DQA1*04:01:02: 02, DQA1*04:01:03, DQA1*04:02, DQA1*04:03N, DQA1*04:04, DQA1*04:05, DQA1*05:01:01:01, DQA1*05:01:01:02, DQA1*05:01:01:03, DQA1*05:01:01: 04, DQA1*05:01:02, DQA1*05:01:04, DQA1*05:01:05, DQA1*05:01:06, DQA1*05:02, DQA1*05:03:01:01, DQA1*05:03:01:02, DQA1*05:04, DQA1*05:05:01:01, DQA1*05:05:01:02, DQA1*05:05:01:03, DQA1*05:05:01: 04, DQA1*05:05:01:05, DQA1*05:05:01:06, DQA1*05: 05:01:07, DQA1*05:05:01:08, DQA1*05:05:01:09, DQA1*05:05:01:10, DQA1*05:05:01:11, DQA1*05:05:01: 12, DQA1*05:05:01:13, DQA1*05:05:01:14, DQA1*05: 05:01:15, DQA1*05:05:01:16, DQA1*05:05:01:17, DQA1*05:05:01:18, DQA1*05:05:01:19, DQA1*05:05:01: 20, DQA1*05:06:01:01, DQA1*05:06:01:02, DQA1*05: 07, DQA1*05:08, DQA1*05:09, DQA1*05:10, DQA1*05: 11, DQA1*05:12, DQA1*05:13, DQA1*05:14, DQA1*05: 15N, DQA1*06:01:01:01, DQA1*06:01:01:02, DQA1*06: 01:01:03, DQA1*06:01:01:04, DQA1*06:01:02, DQA1*06:02, and any combination thereof.

II.A.3. Signal Peptide

In some aspects, the DQ beta chain and/or the DQ alpha chain further comprises a signal peptide. Any signal peptide known in the art can be used in the compositions and methods disclosed herein. In some aspects the DQ beta chain signal peptide is the same as the DQ alpha signal peptide. In some aspects the DQ beta chain signal peptide is different from the DQ alpha signal peptide.

In some aspects, the signal peptide is derived from a native signal peptide. In some aspects, the signal peptide is derived from a naturally occurring DQ beta chain signal peptide. In some aspects, the signal peptide comprises a naturally occurring DQ beta chain signal peptide. In some aspects, the signal peptide is derived from a naturally occurring DQ alpha chain signal peptide. In some aspects, the signal peptide comprises a naturally occurring DQ alpha chain signal peptide. In some aspects, the signal peptide is derived from a fibroin light chain (FibL) signal peptide. In some aspects, the signal peptide comprises SEQ ID NO: 9. In some aspects, the signal peptide is synthetic.

II.A.4. Transmembrane Domain

In some aspects, the DQ beta chain and/or the DQ alpha chain further comprises a transmembrane domain. The transmembrane domain can be any length and of any origin. In some aspects, the transmembrane domain is at least about 1 to at least about 50 amino acid in length. In some aspects, the transmembrane domain is derived from a naturally occurring transmembrane domain. In some aspects, the transmembrane domain comprises a naturally occurring transmembrane domain. In some aspects, the transmembrane domain is derived from a naturally occurring HLA transmembrane domain. In some aspects, the transmembrane domain comprises a naturally occurring HLA transmembrane domain. In some aspects, the transmembrane domain is derived from a naturally occurring DQ beta chain transmembrane domain. In some aspects, the transmembrane domain comprises a naturally occurring DQ beta chain transmembrane domain. In some aspects, the transmembrane domain is derived from a naturally occurring DQ alpha chain transmembrane domain. In some aspects, the transmembrane domain comprises a naturally occurring DQ alpha chain transmembrane domain.

II.A.5. Leucine Zipper

In some aspects, the DQ beta chain and/or the DQ alpha chain further comprises one or more leucine zipper (LZip) sequences. Any LZip sequence known in the art can be used in the compositions and methods disclosed herein. In some aspects, the DQ beta chain and/or the DQ alpha chain comprises an acidic LZip (aLZip), a basic LZip (PLZip), or both. In some aspects, the one or more LZip sequences are derived from a naturally occurring LZip sequence. In some aspects, the one or more LZip sequences comprise a naturally occurring LZip sequence. In some aspects, the one or more LZip sequences are synthetic. In certain aspects, the one or more LZip sequences comprise the LZip sequences set forth in SEQ ID NO: 4 (Table 1).

II.A.6. Linker

In some aspects, the DQ beta chain and/or the DQ alpha chain useful for the disclosure further comprises a linker. Any linker known in the art can be used in the compositions and methods disclosed herein. In certain aspects, the linker comprises a Gly/Ser linker. In some aspects, the linker comprises an amino acid sequence selected from GlySer, $Gly_2Ser$, $Gly_3Ser$, and $Gly_4Ser$. In some aspects, the linker is positioned at the N-terminus of the extracellular domain of the DQ alpha chain or the DQ beta chain. In some aspects, the linker is positioned at the C-terminus of the extracellular domain of the DQ alpha chain or the DQ beta chain. In some aspects, the linker is positioned between the extracellular domain of the DQ alpha chain or the DQ beta chain and the transmembrane domain. In some aspects, the linker is positioned between the extracellular domain of the DQ alpha chain or the DQ beta chain and the one or more LZip sequences. In some aspects, the linker is positioned between the extracellular domain of the DQ alpha chain or the DQ beta chain and the signal peptide.

A linker of any length can be used in the compositions and methods disclosed herein. In some aspects, the linker is at least one amino acid in length. In some aspects, the linker is at least about 1 to at least about 100, at least about 1 to at least about 90, at least about 1 to at least about 80, at least about 1 to at least about 70, at least about 1 to at least about 60, at least about 1 to at least about 50, at least about 1 to at least about 40, at least about 1 to at least about 30, at least about 1 to at least about 20, at least about 1 to at least about 15, at least about 1 to at least about 14, at least about 1 to at least about 13, at least about 1 to at least about 12, at least about 1 to at least about 11, at least about 1 to at least about 10, at least about 1 to at least about 9, at least about 1 to at least about 8, at least about 1 to at least about 7, at least about 1 to at least about 6, at least about 1 to at least about 5, at least about 1 to at least about 4, at least about 1 to at least about 3 amino acids in length.

In some aspects, the linker is at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 30, at least about 40, at least about 50, at least about 60, at least about 70, at least about 80, at least about 90, at least about 100 amino acids in length. In certain aspects, the linker is about 3 amino acids in length. In certain aspects, the linker is about 4 amino acids in length. In certain aspects, the linker is about 5 amino acids in length.

II.B. Cells

In certain aspects of the present disclosure, the MHC class II molecule of the present disclosure is linked to or associated with a membrane of a cell. In certain aspects, the beta chain of the MHC class II molecule is linked or associated with a membrane of a cell. In certain aspects, the alpha chain of the MHC class II molecule is linked or associated with a membrane of a cell. In certain aspects, the alpha chain and the beta chain of the MHC class II molecule are linked or associated with a membrane of a cell.

Certain aspects of the present disclosure are directed to cells comprising an MHC class II molecule disclosed herein. Any cell can be used in the compositions described herein. In certain aspects the cell is a mammalian cell. In some aspects, the cell is an insect cell. In some aspects, the cell is derived from a healthy cell, e.g., a health fibroblast cell. In some aspects the cell is derived from a tumor cell. Non-limiting examples of cells that are useful in the present disclosure include K562 cells, T2 cells, HEK293 cells, HEK293T cells, A375 cells, SK-MEL-28 cells, Me275 cells, COS cells, fibroblast cells, tumor cells, or any combination thereof. In certain aspects, the cell is any cell disclosed in Hasan et al., *Adv. Genet. Eng.* 4(3):130 (2015), which is incorporated by reference herein in its entirety.

In certain aspects, the cell is a professional APC. In certain aspects, the cell is a macrophage, a B cell, a dendritic cell, or any combination thereof.

In certain aspects, the cell lacks endogenous expression of one or more MHC class II allele. In some aspects the cell lacks endogenous expression of an HLA-DQ allele. In some aspects the cell lacks endogenous expression of an HLA-DQ alpha chain allele. In some aspects the cell lacks endogenous expression of an HLA-DQ beta chain allele.

II.C. Soluble MHC Class II Molecules

In certain aspects, the MHC class II molecule is not associated with a membrane of a cell, e.g., the MHC class II molecule is in a soluble form. As used herein, a soluble MHC class II molecule includes any MHC class II molecule or a portion thereof, described herein, that is not associated with a cell membrane. In certain aspects, the MHC class II molecule or portion thereof is unbound to any membrane. In some aspects, the MHC class II molecule or portion thereof is bound to an inert particle. In some aspects, the MHC class II molecule or portion thereof is bound to the membrane of an extracellular vesicle. In some aspects, the MHC class II molecule is bound to an artificial membrane or an artificial surface, e.g., the surface of an array plate.

Any inert particle known in the art can be used in the compositions and methods of the present disclosure. In some aspects, the inert particle is a bead. In some aspects, the bead is a glass bead, a latex bead, a metal bead, or any combination thereof. In some aspects, the inert particle is a nanoparticle (NP). Any NP known in the art can be used in the compositions and methods of the present disclosure. In certain aspects, the nanoparticle is selected from a pegylated iron oxide, chitosan, dextrane, gelatin, alginate, liposome, starch, branched polymer, carbon-based carrier, polylactic acid, poly(cyano)acrylate, polyethyleinemine, block copolymer, polycaprolactone, SPIONS, USPIONS, Cd/Zn-selenide, or silica nanoparticle. In particular aspects, the nanoparticle is a pegylated iron oxide nanoparticle. Nonlimiting examples of nanoparticles useful in the compositions and methods disclosed herein include those set forth in De Jong and Borm, *Int. J. Nanomedicine* 3(2):133-49 (2008) and Umeshappa et al., *Nat. Commun.* 10(1):2150 (May 14, 2019), each of which is incorporated by reference herein in its entirety.

In some aspects, the MHC class II molecule comprises a fragment of a full length MHC class II molecule, wherein one or more amino acids of the transmembrane domain of the alpha chain and/or the transmembrane domain of the beta chain are deleted. In some aspects, the MHC class II molecule comprises the extracellular domain of the alpha chain (e.g., as set forth in SEQ ID NO: 6) and/or the extracellular domain of the beta chain (e.g., as set forth in SEQ ID NO: 1 or 3). In certain aspects, the MHC class II molecule comprises a DQ alpha chain comprising an amino acid sequence having at least about 80%, at least about 85%, at least about 90%, at least about 95%, at least about 96%, at least about 97%, at least about 98%, or at least about 99% sequence identity to SEQ ID NO: 6. In some aspects, the MHC class II molecule comprises a DQ alpha chain comprising an amino acid sequence set forth in SEQ ID NO: 6.

In certain aspects, the MHC class II molecule comprises a DQ beta chain comprising an amino acid sequence having at least about 80%, at least about 85%, at least about 90%, at least about 95%, at least about 96%, at least about 97%, at least about 98%, or at least about 99% sequence identity to SEQ ID NO: 1. In some aspects, the MHC class II molecule comprises a DQ beta chain comprising an amino acid sequence set forth in SEQ ID NO: 1. In certain aspects, the MHC class II molecule comprises a DQ beta chain comprising an amino acid sequence having at least about 80%, at least about 85%, at least about 90%, at least about 95%, at least about 96%, at least about 97%, at least about 98%, or at least about 99% sequence identity to SEQ ID NO: 3. In some aspects, the MHC class II molecule comprises a DQ beta chain comprising an amino acid sequence set forth in SEQ ID NO: 3. In certain aspects, the MHC class II molecule comprises a DQ beta chain comprising an amino acid sequence having at least about 80%, at least about 85%, at least about 90%, at least about 95%, at least about 96%, at least about 97%, at least about 98%, or at least about 99% sequence identity to SEQ ID NO: 4. In some aspects, the MHC class II molecule comprises a DQ beta chain comprising an amino acid sequence set forth in SEQ ID NO: 4. In certain aspects, the MHC class II molecule comprises a DQ beta chain comprising an amino acid sequence having at least about 80%, at least about 85%, at least about 90%, at least about 95%, at least about 96%, at least about 97%, at least about 98%, or at least about 99% sequence identity to SEQ ID NO: 5. In some aspects, the MHC class II molecule comprises a DQ beta chain comprising an amino acid sequence set forth in SEQ ID NO: 5.

II.D. Nucleic Acid Molecules and Vectors

Certain aspects of the present disclosure are directed to a nucleic acid molecule encoding an MHC class II molecule disclosed herein. In some aspects the nucleic acid molecule encodes an MHC class II beta chain disclosed herein. In certain aspects, the nucleic acid molecule encoding the MHC class II beta chain comprises a nucleotide sequence having at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% sequence identity with the sequence set forth in SEQ ID NO: 2.

In some aspects the nucleic acid molecule encodes an MHC class II alpha chain disclosed herein. In certain aspects, the nucleic acid molecule encoding the MHC class II alpha chain comprises a nucleotide sequence having at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% sequence identity with the sequence set forth in SEQ ID NO: 7.

In some aspects, the nucleic acid molecule encodes both an MHC class II alpha chain disclosed herein and an MHC class II beta chain disclosed herein. In some aspects, the sequence encoding the MHC class II alpha chain is under the control of the same promoter as the sequence encoding the MHC class II beta chain. In some aspects, the sequence encoding the MHC class II alpha chain is under the control of a first promoter, and the sequence encoding the MHC class II beta chain is under the control of a second promoter.

In some aspects, the present disclosure is directed to a first nucleic acid molecule encoding an MHC class II beta chain disclosed herein and a second nucleic acid molecule encoding an MHC class II alpha chain disclosed herein.

Certain aspects of the present disclosure are directed to a vector or a set of vectors comprising a nucleic acid molecule disclosed herein. In some aspects, the vector is a viral vector. In some aspects, the vector is a viral particle or a virus. In some aspects, the vector is a mammalian vector. In some aspects, the vector is a bacterial vector.

In certain aspects, the vector is a retroviral vector. In some aspects, the vector is an adenoviral vector, a lentivirus, a Sendai virus, a baculoviral vector, an Epstein Barr viral vector, a papovaviral vector, a vaccinia viral vector, a herpes simplex viral vector, or an adeno associated virus (AAV) vector. In particular aspects, the vector is an AAV vector. In some aspects, the vector is a lentivirus. In particular aspects, the vector is an adenoviral vector. In some aspects, the vector is a Sendai virus. In some aspects, the vector is a hybrid vector. Examples of hybrid vectors that can be used in the present disclosure can be found in Huang and Kamihira, *Biotechnol. Adv.* 31(2):208-23 (2103), which is incorporated by reference herein in its entirety.

III. Methods of the Disclosure

Certain aspects of the present disclosure are directed to methods of treating a disease or condition in a subject. In some aspects, the disclosure is directed to methods of enhancing an immune response in a subject in need thereof.

III.A. Methods of Treating a Tumor

Certain aspects of the present disclosure are directed to methods of treating a cancer in a subject in need thereof, comprising administering to the subject an HLA class II molecule disclosed herein, a nucleic acid molecule disclosed herein, a vector disclosed herein, or a cell disclosed herein.

In some aspects, the cancer is selected from melanoma, bone cancer, renal cancer, prostate cancer, breast cancer, colon cancer, lung cancer, cutaneous or intraocular malignant melanoma, pancreatic cancer, skin cancer, cancer of the head or neck, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia (AML), chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of the cancers. In some aspects, the cancer is melanoma.

In some aspects, the cancer is relapsed. In some aspects, the cancer is refractory. In some aspects, the cancer is advanced. In some aspects, the cancer is metastatic.

In some aspects, the methods disclosed herein treat a cancer in a subject. In some aspects, the methods disclosed herein reduce the severity of one or more symptom of the cancer. In some aspects, the methods disclosed herein reduce the size or number of a tumor derived from the cancer. In some aspects, the methods disclosed herein increase the overall survival of the subject, relative to a subject not provided the methods disclosed herein. In some aspects, the methods disclosed herein increase the progressive-free survival of the subject, relative to a subject not provided the methods disclosed herein. In some aspects, the methods disclosed herein lead to a partial response in the subject. In some aspects, the methods disclosed herein lead to a complete response in the subject.

Certain aspects of the present disclosure are directed to methods of treating an infection in a subject in need thereof, comprising administering to the subject an HLA class II molecule disclosed herein, a nucleic acid molecule disclosed herein, a vector disclosed herein, or a cell disclosed herein. Non-limiting examples of infections that can be treated using the compositions and methods disclosed herein include infection by a virus (including viroids and prions), a bacterium, a fungus, a parasite, or any combination thereof. In some aspects, the virus is herpesvirus, HIV, papvavirus, measles virus, rubella virus, human papillomavirus (HPV), human T-lymphotropic virus 1, Epstein-Barr virus, hepatitis A virus, hepatitis B virus, hepatitis C virus, influenza virus, norovirus, and any combination thereof. In some aspects, the bacterium is selected from *Streptococcus, Staphylococcus*, and *E. coli*. In some aspects, the bacterial infection is selected from Brucellosis, *Campylobacter* infections, Cat-scratch disease, Cholera, *Escherichia coli*, Gonorrhea, *Klebsiella, Enterobacter, Serratia, Legionella* infections, Meningococcal infection, Pertussis, Plague, *Pseudomonas* infection, *Salmonella* infection, Shigellosis, Typhoid fever, Tularemia, Anthrax, Diphtheria, Enterococcal infection, Erysipelothricosis, Listeriosis, Nocardiosis, Pneumococcal infection, Staphylococcal infection, Streptococcal infection, and any combination thereof. In some embodiments, the parasite infection is selected from pinworm, trichomononiasis, toxoplasmosis, giardiasis, cryptosporidiosis, malaria, hookwork, ringworm, tapeworm, fluke, and any combination thereof. In some aspects, the fungal infection is selected from *Candida, Malassezia fur-*

*fur*, dermatophytes (e.g., *Epidermophyton, Microsporum*, and *Trichophyton*), or any combination thereof.

In some aspects, the methods disclosed herein comprise treating a cancer or an infection in a subject in need thereof, comprising administering to the subject a cell described herein, wherein the cell comprises an MHC class II molecule disclosed herein, a nucleic acid molecule disclosed herein, a vector disclosed herein, or any combination thereof.

In some aspects, the cell is obtained from the subject. In some aspects, the cell is obtained from a donor other than the subject.

III.B. Methods of Enriching a Target Population of T Cells

Certain aspects of the present disclosure are directed to methods of enriching a target population of T cells obtained from a human subject. In some aspects, the method comprises contacting the T cells with an HLA class II molecule disclosed herein. In some aspects, the method comprises contacting the T cells with a cell, e.g., an APC, disclosed herein. In some aspects, following the contacting, the enriched population of T cells comprises a higher number of T cells capable of binding the HLA class II molecule relative to the number of T cells capable of binding the HLA class II molecule prior to the contacting.

Some aspects of the present disclosure are directed to a method of selecting a T cell capable of targeting a diseased cell, e.g., a tumor cell. In some aspects, the method comprises contacting a population of isolated T cells in vitro with a complex comprising an MHC class II molecule disclosed herein and a fragment of a polypeptide, e.g. an antigen expressed by a diseased cell, e.g., a tumor-expressed polypeptide, e.g., an epitope. In some aspects, the T cells are obtained from a human subject.

The T cells obtained from the human subject can be any T cells disclosed herein. In some aspects, the T cells obtained from the human subject are tumor infiltrating lymphocytes (TIL).

In some aspects, the method further comprises administering to the human subject the enriched T cells. In some aspects, the subject is preconditioned prior to receiving the T cells, as described herein.

All of the various aspects, aspects, and options described herein can be combined in any and all variations.

All publications, patents, and patent applications mentioned in this specification are herein incorporated by reference to the same extent as if each individual publication, patent, or patent application was specifically and individually indicated to be incorporated by reference.

Having generally described this disclosure, a further understanding can be obtained by reference to the examples provided herein. These examples are for purposes of illustration only and are not intended to be limiting.

EXAMPLES

Example 1—Methods

Cells

Peripheral mononuclear cells were obtained via density gradient centrifugation (Ficoll-Paque PLUS, GE Healthcare Life Sciences, Marlborough, MA). The K562 cell line is an erythroleukemic cell line with defective HLA class I/II expression. A375 is melanoma cell lines. HEK293T cells and A375 cells were grown in DMEM supplemented with 10% FBS and 50 µg/ml gentamicin (Thermo Fisher Scientific, Waltham, MA). The K562 and Jurkat 76 cell lines were cultured in RPMI 1640 supplemented with 10% FBS and 50 µg/ml gentamicin.

Peptides

Synthetic peptides were purchased from Genscript (Piscataway, NJ) and dissolved at 50 µg/ml in DMSO.

Antibodies

The following antibodies were used for flow cytometry analysis: PE-conjugated anti-class II (9-49 (I3), Beckman Coulter, Brea, CA; T039), APC-Cy7-conjugated anti-CD4 (RPA-T4, Biolegend, San Diego, CA) and PE-conjugated anti-His tag (AD1.1.10, Abcam, Cambridge, MA). Dead cells were distinguished with the LIVE/DEAD Fixable Near-IR Dead Cell Stain Kit 465 (Thermo Fisher Scientific, Waltham, MA). Stained cells were analyzed with Canto II or LSRFortessa X-20 (BD Biosciences, Franklin Lakes, NJ). Cell sorting was conducted using a FACS Aria II (BD Biosciences, Franklin Lakes, NJ). Data analysis was performed using FlowJo software (Tree Star, Ashland, OR).

TCR Transduction into Primary T Cells

CD3$^+$ and CD4$^+$ T cells were purified using the Pan T Cell Isolation Kit (Miltenyi Biotec, Bergisch Gladbach, Germany) and CD4$^+$ T Cell Isolation Kit (Miltenyi Biotec, Bergisch Gladbach, Germany), respectively. Purified T cells were stimulated with aAPC/mOKT3 irradiated with 200 Gy at an E:T ratio of 20:1. Starting the following day, activated T cells were retrovirally transduced with the cloned TCR genes via centrifugation for 1 hour at 1,000×g at 32° C. for 3 consecutive days or using a Retronectin-coated plate (Takara Bio, Shiga, Japan). On the following day, 100 IU/ml IL-2 and 10 ng/ml IL-15 were added to the TCR-transduced T cells. The culture medium was replenished every 2-3 days.

Staining with Soluble CD4

The soluble CD4 (sCD4) gene was generated by fusing the human CD4 extracellular domain with a 6×His tag via a GS linker. HEK293T cells were retrovirally transduced with the sCD4 gene, and the culture supernatant containing the sCD4 monomer was harvested. sCD4 was dimerized with a PE-labeled anti-6×His tag mAb (AD1.1.10, Abcam, Cambridge, MA) and used. HLA class II-expressing K562 cells were stained with dimerized sCD4 in the presence of goat serum for 30 min at room temperature. The surface HLA class II expression in K562-derived cells individually expressing various class II genes was as demonstrated in FIGS. 3A-3Q.

Generation of the HLA Class H Monomer and Dimer

The extracellular domain of the wild-type class II a gene was fused with an acidic leucine zipper via a GGGS linker followed by a 6×His tag via a GS linker (see SEQ ID NO: 8). The ectodomain of the class II β gene carrying mutations (see SEQ ID NO: 3) was similarly linked with a basic leucine zipper via a GGGS linker (see SEQ ID NO: 4). HEK293T cells and A375 cells were transfected with the α and p genes using the 293GPG cell-based retrovirus system and cultured in DMEM supplemented with 10% FBS and 50 g/ml gentamicin. For DQ5 dimer staining, HEK293T cells and A375 cells stably secreting soluble DQ5$^{L114W/V143M+4reps}$ (which possesses the N110Q/I116V/S118H/P146N replacements (4reps) in addition to L114W/V143M) protein were grown until confluent, and after forty-eight hours, the medium was harvested. The soluble HLA class II-containing supernatant was then mixed with 100 µg/ml peptide of interest for 20-24 hours at 37° C. for in vitro peptide exchange. Monomer that was not subjected to peptide exchange was used as a control. The concentration of the monomer was measured by specific ELISA using a nickel-coated plate (XPressBio, Frederick, MD) and an anti-His tag biotinylated mAb (AD1.1.10, R&D Systems, Minneapolis, MN). Soluble HLA class II monomer was dimerized using PE-conjugated anti-His mAb (AD1.1.10, Abcam, Cambridge, MA) at a 2:1 molar ratio for 1.5 hours at 4° C. for staining.

HLA Class H Dimer Staining

Primary T cells transduced with exogenous TCR gene were pretreated with 50 nM dasatinib (LC Laboratories, Woburn, MA) for 30 min at 37° C.[46] and stained with 5-15 µg/ml class II dimer for 4-5 hours at room temperature. After washing, cell surface molecules were counterstained with an APC-Cy7-conjugated anti-CD4 mAb.

Statistical Analysis

Statistical analysis was performed using GraphPad Prism 6.0 software (GraphPad Software, San Diego, CA). Unpaired two-tailed Student's t-tests were used for two-sample comparisons. No statistical method was used to predetermine sample size. The investigators were not blinded to allocation during the experiments or outcome assessment. The experiments were not randomized.

Example 2—DQ Molecules with Enhanced CD4 Binding Capacities

Figure 1B:
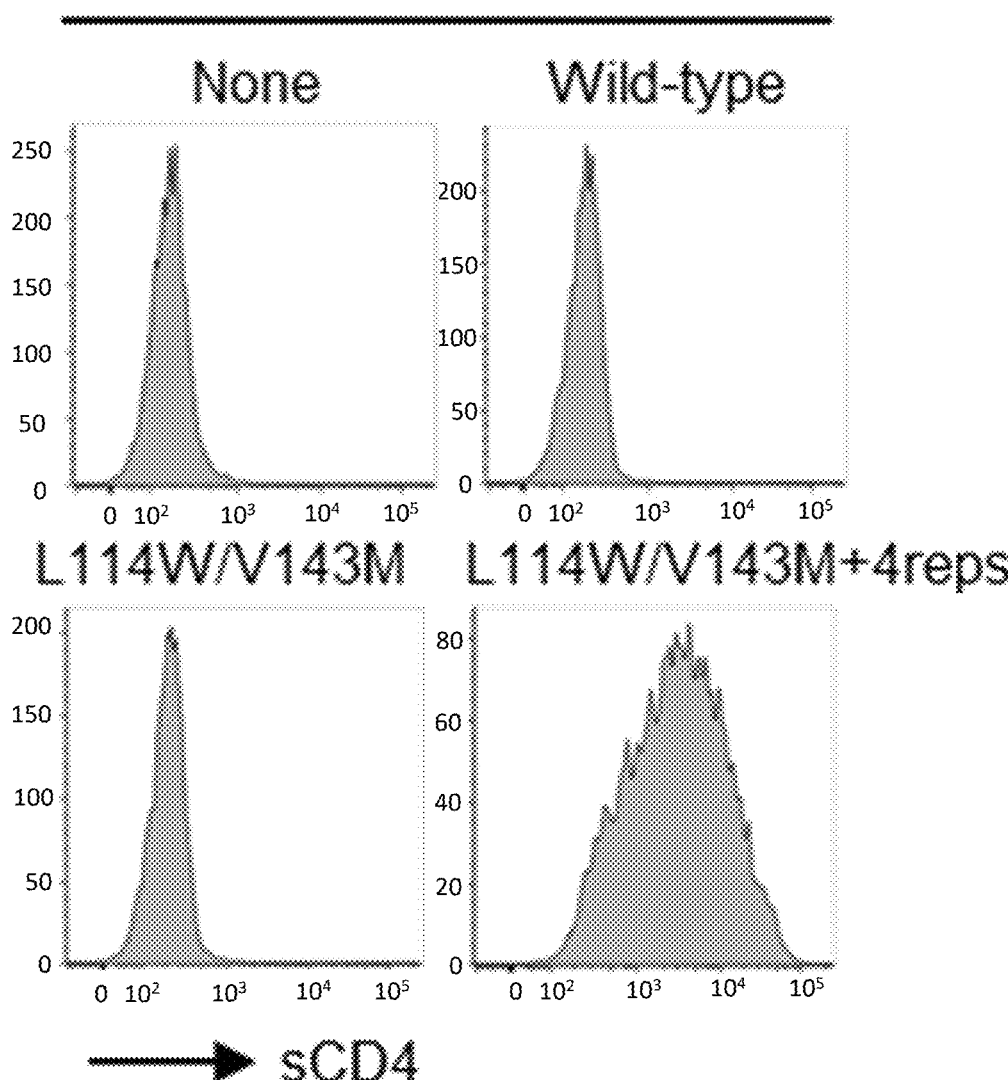
Figure 1C:
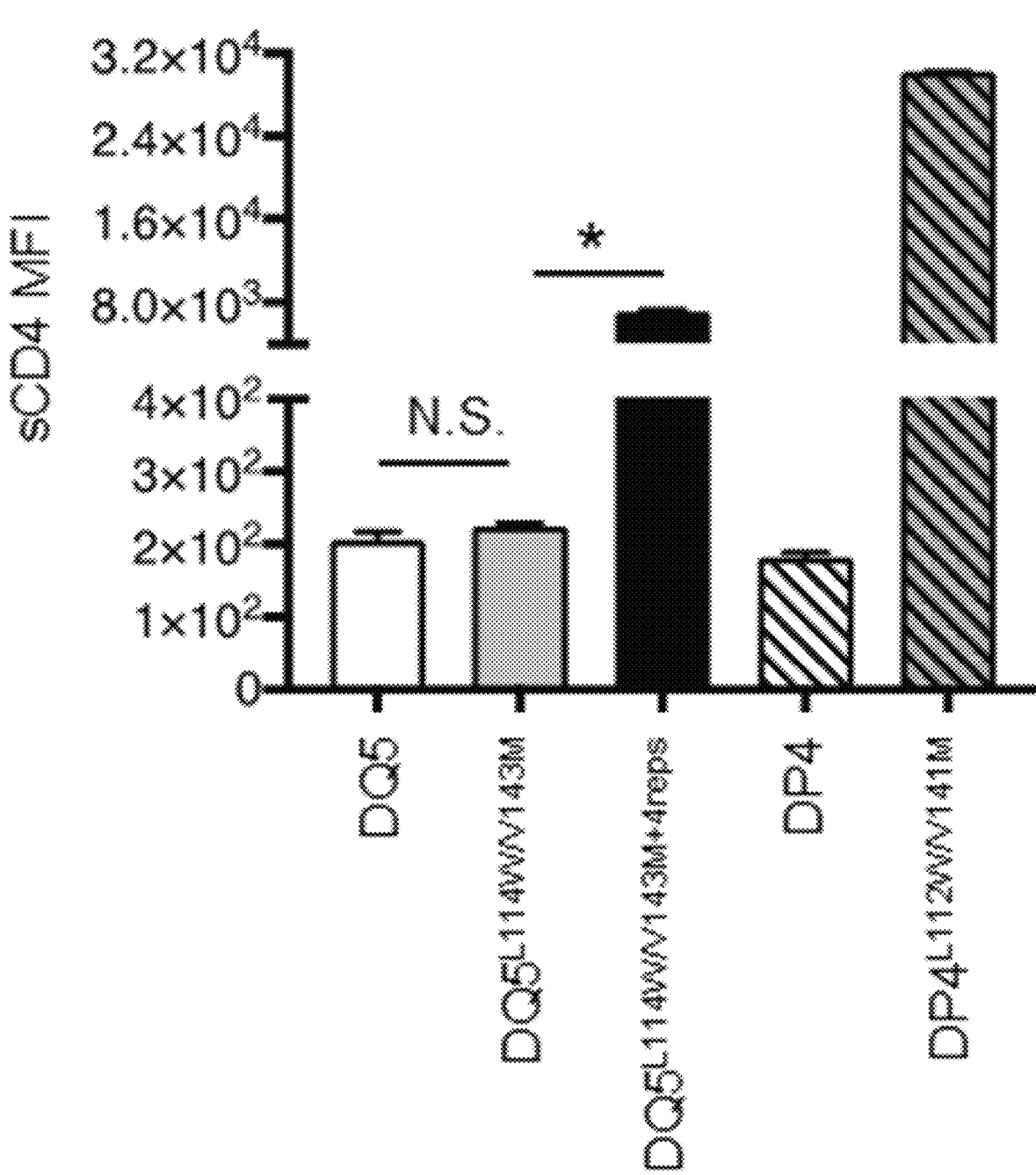
Figure 1D:
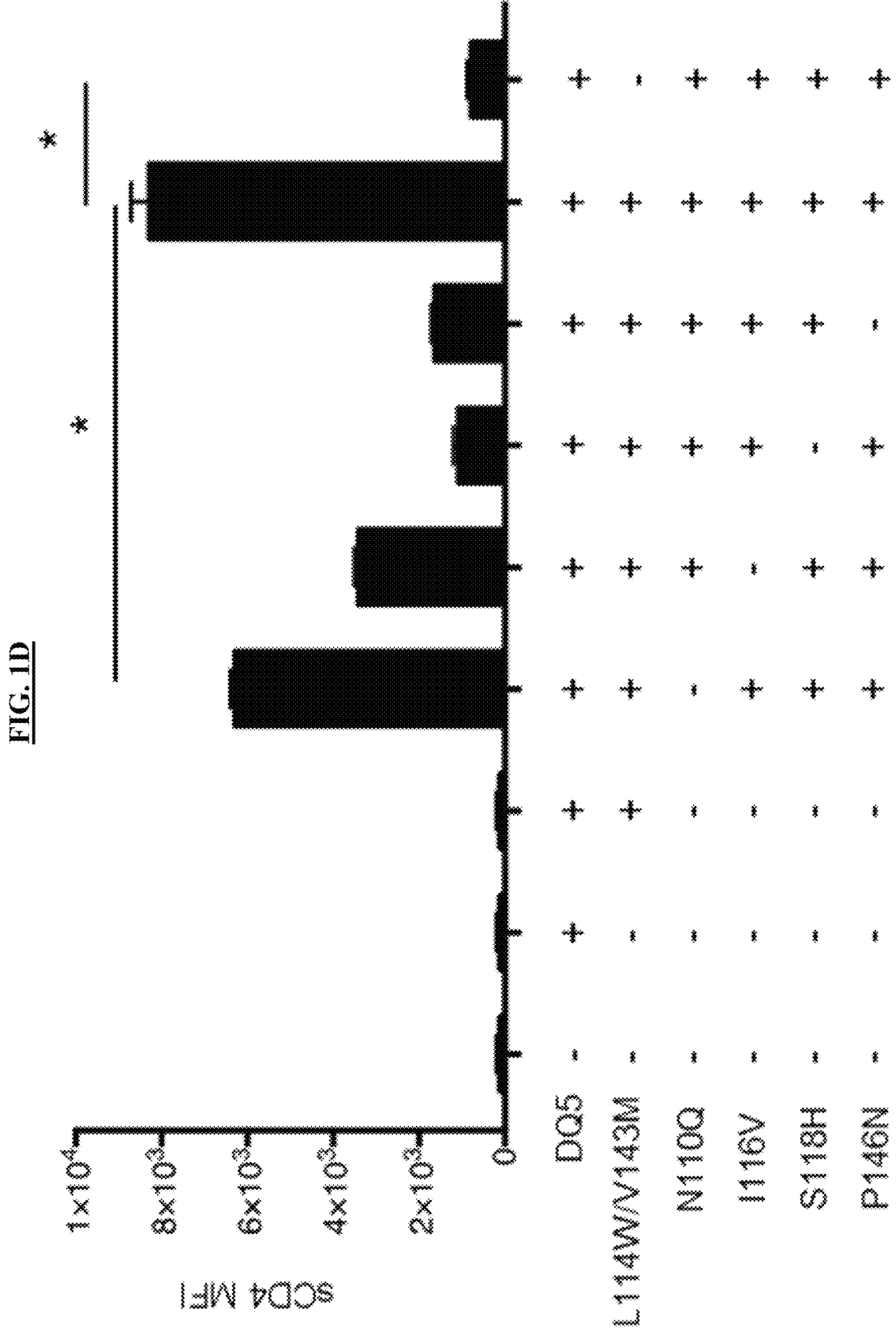

Affinity enhanced DQ molecules were generated by introducing L114W/V143M mutations, to determine if these substitutions could improve the binding of HLA-DQ molecules such as DQ5 (DQA1*01:01-DQB1*05:01) to CD4. DQB1*05:01 encodes four different amino acids at positions 110, 116, 118, and 146 in addition to 114 and 143. We therefore generated K562 cells expressing DQ5$^{L114W/V143M+4reps}$ which possesses the N110Q/I116V/S118H/P146N replacements (4reps) in addition to L114W/V143M (FIG. 1A), and stained the cells with sCD4. K562 cells expressing DQ5$^{L114W/V143M+4reps}$ but not DQ5$^{L114W/V143M}$, DQ5$^{4reps}$, or wild-type DQ5 demonstrated enhanced CD4 binding (FIGS. 1B-1C). Importantly, a series of K562 cells individually expressing various DQ5$^{L114W/V143M+4reps}$ mutants with a single amino acid reversal at one of the four positions lacked the enhanced CD4 binding capability (FIG. 1D). These results suggest that the four additional replacements at N110Q, I116V, S118H, and P146N are critical for the effectiveness of the L114W/V143M mutations in the observed enhanced DQ5:CD4 binding.

Figure 1F:
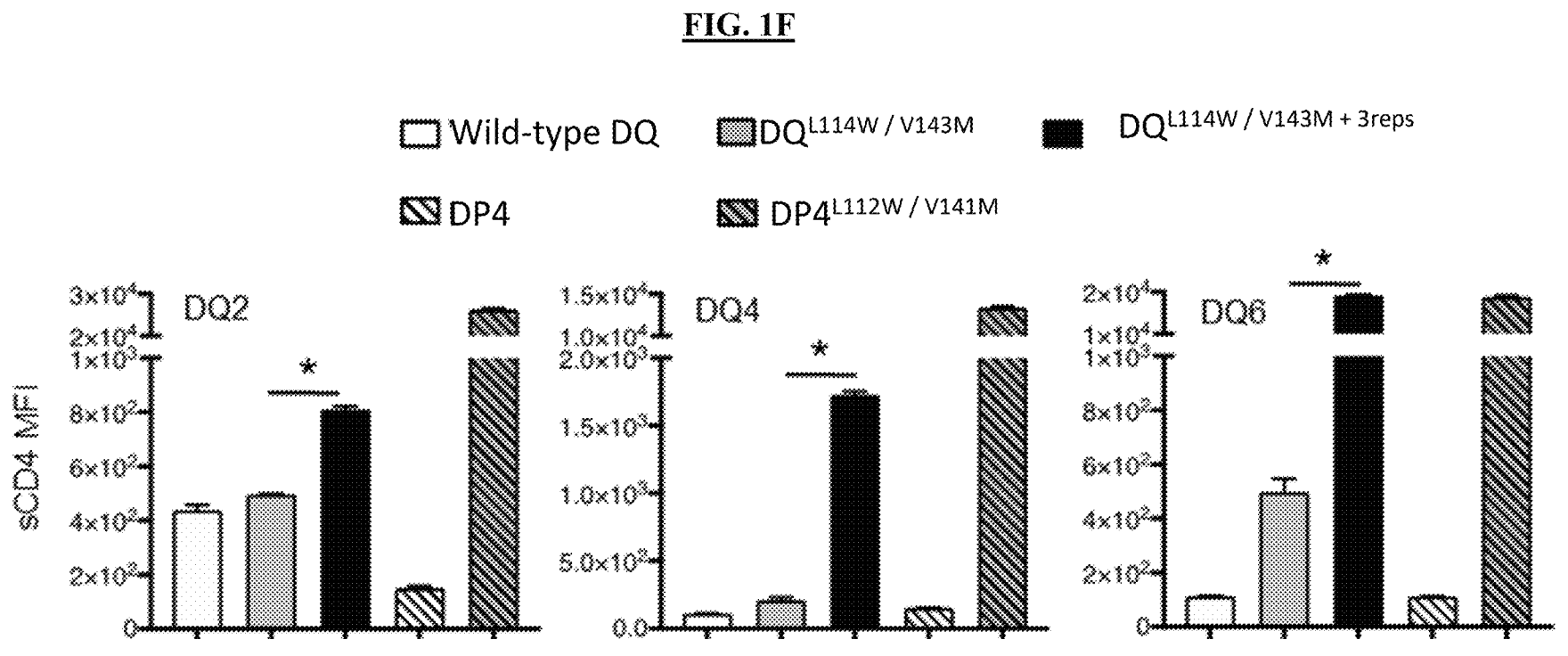

DQβ chains such as DQB1*02:01, 04:02, and 06:01 encode distinct amino acids at positions 110, 118, and 146 but not at 116 (FIG. 1E). Unlike DQB1*05:01, DQB1*02:01, 04:02, and 06:01 encode Val at position 116, similar to DPB1*04:01, which codes for Val at position 114. All the DQ2$^{L114W/V143M+3reps}$, DQ4$^{L114W/V143M+3reps}$, and DQ6$^{L114W/V143M+3reps}$ mutants, the β chains of which carry the N110Q, S118H, and P146N replacements (3reps) along with L114W/V143M, showed enhanced CD4 binding activity (FIG. 1F).

Figure 2A:
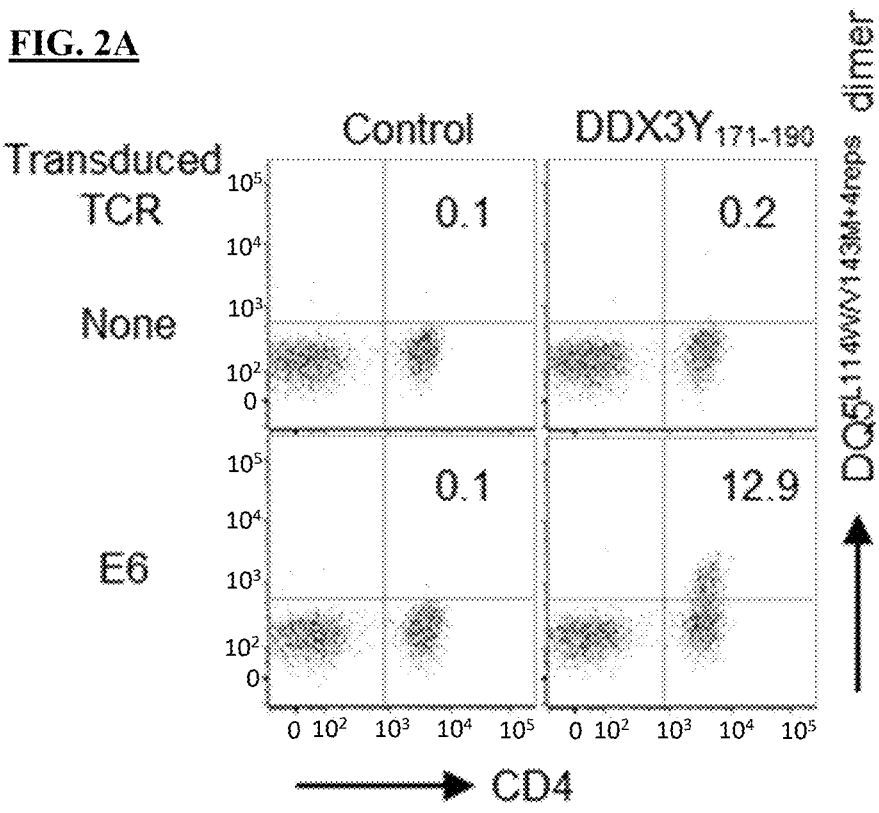
FIGS. 2A-2B are graphical representations illustrating that affinity-matured DQ dimers detected cognate TCRs expressed in human primary CD4+ T cells. DQ5 (DQA1*01:01-DQB1*05:01)-restricted DDX3Y-specific TCR (E6) (FIG. 2A) and DQ6 (DQA1*01:02-DQB1*06:02)-restricted influenza virus HA-specific TCR (DM2) (FIG. 2B) were reconstituted in human primary CD4+ T cells and stained by $DQ5^{L114W/V143M+4reps}$ and $DQ6^{L114W/V143M+3reps}$ dimers, respectively. At least 2 independent experiments were performed.
Figure 2B:
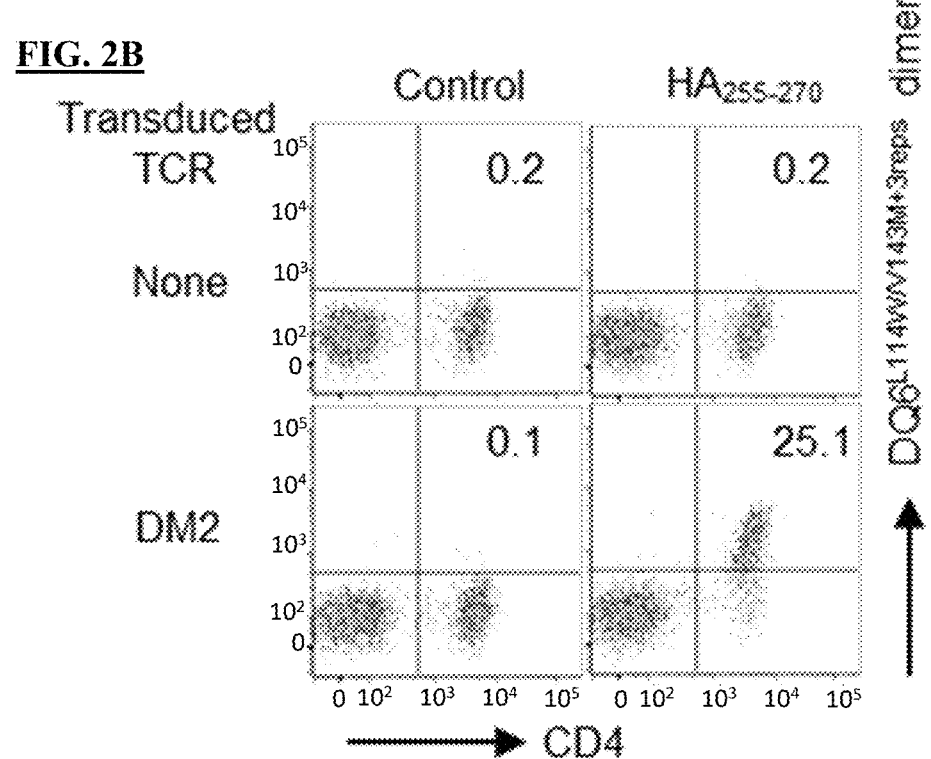

Example 3—Affinity-Matured DQ Dimers Specifically and Robustly Stained Cognate TCRs The ability of the affinity-matured DQ dimers carrying the mutations described in example 2 were evaluated for the ability to identify antigen-specific CD4$^+$ T cells. The DQ5$^{L114W/V143M+4reps}$ and DQ6$^{L114W/V143M+3reps}$ dimers successfully stained the DQ5-restricted DDX3Y-specific TCR (E6) and DQ6-restricted influenza virus-specific TCR (DM2), respectively (FIGS. 2A-2B).

To identify affinity-matured class II molecules, the present examples detail multiple mutations in the j-chain but not the α-chain because the j-chain has a more direct interaction with CD4 than the α chain. It is possible that additional mutations of the α- and/or β-chains can further enhance the binding between class II and CD4. However, the use of such soluble class II molecules with excessive CD4 binding capabilities may cause nonspecific staining of CD4⁺ T cells, thereby having a detrimental effect.

In conclusion, CD4⁺ T cells play a critical role in the development of autoimmune diseases and protection against pathogenic infections and cancers. The novel HLA class II multimer technology described herein may better facilitate the study of HLA class II-restricted CD4⁺ T cell responses across HLA-DQ alleles.

Example 4

Wild-type DQ5 and DQ5$^{L114W/V143M}$ dimers (Table 3) and DQ5$^{L114W/V143M+4reps}$ dimers were produced and their staining of TCR-transduced CD4⁺ T cells was compared. The wild-type DQ5 dimers could not detect E6-transduced CD4⁺ T cells. The DQ5$^{L114W/V143M}$ dimers showed only weak staining of the E6-transduced CD4⁺ T cells compared to the DQ5$^{L114W/V143M+4reps}$ dimers, which instead showed robust staining (FIGS. 4A-4L). To validate DQ5$^{L114W/V143M+4reps}$ dimer staining, we cloned a DQ5-restricted TCR gene specific to GPC3$_{138-157}$ from dimer⁺ CD4⁺ T cells in vitro expanded in a peptide-specific manner. When clonotypically reconstituted in human CD4⁺ TCR-deficient T cells, the TCR was successfully stained by the cognate DQ5$^{L114W/V143M+4reps}$ dimer and were functional in a DQ5-restricted and antigen-specific manner (FIGS. 5A-5G).

Methods

Cells

Peripheral mononuclear cells were obtained via density gradient centrifugation. K562-based artificial antigen presenting cells (aAPCs) individually expressing various HLA class II genes as a single HLA allele in conjunction with CD80 and CD83 have been reported previously (Butler, M. O. et al., *PLoS One* 7, e30229 (2012)). The Jurkat 76 cell line is a T cell leukemic cell line lacking endogenous TCR, CD4, and CD8 expression (see. Heemskerk, M. H. et al., *Blood* 102, 3530-3540 (2003)). Jurkat 76/CD4 cells were generated by retrovirally transducing the human CD4 gene. A375 cells are a melanoma cell line. HEK293T cells and A375 cells were grown in DMEM supplemented with 10% FBS and 50 µg/ml gentamicin. The Jurkat 76 cell line was cultured in RPMI 1640 supplemented with 10% FBS and 50 µg/ml gentamicin.

Peptides

Synthetic peptides were dissolved at 50 mg/ml in DMSO.

Genes

Novel TCR genes were cloned via 5'-rapid amplification of cDNA ends (RACE) PCR and sequenced as previously described (see, e.g., Nakatsugawa, M. et al., *Sci Rep* 6, 23821 (2016); Nakatsugawa, M. et al., *J Immunol* 194, 3487-3500 (2015); and Ochi, T. et al., *Cancer Immunol Res* 3, 1070-1081 (2015); each of which is incorporated by reference herein in its entirety). All genes were cloned into the pMX retroviral vector and transduced into cell lines using the 293GPG and PG13 cell-based retrovirus system (see, e.g., Hirano, N. et al., *Blood* 107, 1528-1536 (2006); Butler, M. O. et al., *Clin Cancer Res* 13, 1857-1867 (2007); Hirano, N. et al., *Clin Cancer Res* 12, 2967-2975 (2006); each of which is incorporated by reference herein in its entirety).

Antibodies

The following antibodies were used for flow cytometry analysis: APC-Cy7-conjugated anti-CD4 (RPA-T4, BIOLEGEND, San Diego, CA; see Wooldridge, L. et al., *Eur J Immunol* 36, 1847-1855 (2006)) and PE-conjugated anti-His tag (AD1.1.10, ABCAM, Cambridge, MA). Dead cells were distinguished with the LIVE/DEAD Fixable Aqua Dead Cell Stain Kit. Stained cells were analyzed with FACSCanto II or LSRFortessa X-20. Cell sorting was conducted using a FACSAria II. Data analysis was performed using FlowJo software (version 9.9.6).

Generation of the HLA Class II Monomer and Dimer

A375 cells were transfected with the α and p genes using the 293GPG cell-based retrovirus system (see, e.g., Hirano, N. et al., *Blood* 107, 1528-1536 (2006); Butler, M. O. et al. *Clin Cancer Res* 13, 1857-1867 (2007); and Hirano, N. et al., *Blood* 108, 2662-2668 (2006); each of which is incorporated by reference herein in its entirety) and cultured in DMEM supplemented with 10% FBS and 50 µg/ml gentamicin. After forty-eight hours, the conditioned medium was harvested and concentrated by filtration (molecular weight cut-off (MWCO) 10 kDa). The soluble HLA class II-containing supernatant was then mixed with 100 µg/ml peptide of interest for 20-24 hours at 37° C. for in vitro peptide exchange. The concentration of the monomer was measured by specific ELISA using a nickel-coated plate and an anti-His tag biotinylated mAb. Soluble HLA class II monomer was dimerized using PE-conjugated anti-His mAb at a 2:1 molar ratio for 1.5 hours at 4° C. for staining.

Stimulation of DQ5-Restricted Antigen-Specific CD4⁺ T Cells

CD4⁺ T cells were purified and then stimulated with DQ5-expressing aAPCs pulsed with GPC3$_{138-157}$ at 10 µg/ml and irradiated at 200 Gy at an E:T ratio of 20:1. After forty-eight hours, 10 IU/ml IL-2 and 10 ng/ml IL-15 were added to the CD4⁺ T cells. The culture medium supplemented with TL-2 (10 IU/ml) and IL-15 (10 ng/ml) was replenished every 2-3 days. Two weeks later, the T cells were subjected to DQ5$^{L114W/V143M+4reps}$ dimer staining.

HLA Class II Dimer Staining

Primary CD4⁺ T cells and Jurkat 76/CD4 T cells transduced with antigen-specific TCR genes were pretreated with 50 nM dasatinib for 30 min at 37° C. and stained with 5-15 µg/ml class II dimers for 4-5 hours at room temperature. After washing, cell surface molecules were counterstained with an APC-Cy7-conjugated anti-CD4 mAb.

TABLE 3

| | | | | | | | |
|---|---|---|---|---|---|---|---|
| | | | | TCR Sequences | | | |
| No. | Peptide | TRAV | TRAJ | TCRα CDR3 | TRBV | TRBJ | TCRβ CDR3 |
| 06 | GPC3$_{138-157}$ | 9-2*02 | 27*01 | CALYTNAGKSTF (SEQ ID NO: 14) | 15*02 | 2-3*01 | CATSRDVSSTDTQYF (SEQ ID NO: 15) |

ELISPOT Assay

Cytokine ELISPOT assays were performed as previously reported (see, e.g., Yamashita, Y. et al., *Nat Commun* 8, 15244 (2017); and Anczurowski, M. et al., *Sci Rep* 8, 4804 (2018); each of which is incorporated by reference herein in its entirety).

---

The invention claimed is:

1. A DQ beta chain comprising an amino acid sequence with:

at least 80% identity to the amino acid sequence of SEQ ID NO: 3 and
(i) a tryptophan at the position corresponding to amino acid residue 114 of SEQ ID NO: 3;
(ii) a methionine at the position corresponding to amino acid residue 143 of SEQ ID NO: 3;
(iii) a glutamine at the position corresponding to amino acid residue 110 of SEQ ID NO: 3;
(iv) a valine at the position corresponding to amino acid residue 116 of SEQ ID NO: 3;
(v) a histidine at the position corresponding to amino acid residue 118 of SEQ ID NO: 3; and
(vi) an asparagine at the position corresponding to amino acid residue 146 of SEQ ID NO: 3.

2. The DQ beta chain of claim 1, comprising the amino acid sequence set forth in SEQ ID NO: 3.

3. An HLA class II molecule comprising a DQ beta chain of claim 1 and a DQ alpha chain.

4. The HLA class II molecule of claim 3, wherein the DQ alpha chain comprises an amino acid sequence having at least 80% sequence identity to SEQ ID NO: 6 or 8.

5. The HLA class II molecule of claim 4, wherein the DQ alpha chain comprises the amino acid sequence set forth in SEQ ID NO: 6 or 8.

6. A nucleic acid molecule encoding the HLA class II molecule of claim 3.

7. A cell comprising the HLA class II molecule of claim 3.

8. A complex comprising the HLA class II molecule of claim 3 and a peptide, wherein the peptide comprises $DDX3Y_{171-190}$, $HA_{255-270}$, $GPC3_{138-157}$, or any combination thereof.

9. The DQ beta chain of claim 1 comprising the amino acid sequence set forth in SEQ ID NO: 4.

10. The cell of claim 7, which is a mammalian cell or an insect cell.

11. The cell of claim 7, which is a K562 cell, T2, HEK293, HEK293T, A375, SK-MEL-28, Me275, COS, a fibroblast cell, or a tumor cell.

12. The cell of claim 7, which (i) lacks endogenous MHC class II DQ beta chain expression, (ii) lacks endogenous MHC class II DQ alpha chain expression, (iii) or both (i) and (ii).

13. The HLA class II molecule of claim 3, wherein the DQ beta chain comprises the amino acid sequence set forth in SEQ ID NO: 3.

14. The HLA class II molecule of claim 13, wherein the DQ beta chain comprises the amino acid sequence set forth in SEQ ID NO: 4.

* * * * *